US007319386B2

(12) United States Patent
Collins, Jr. et al.

(10) Patent No.: US 7,319,386 B2
(45) Date of Patent: Jan. 15, 2008

(54) CONFIGURABLE SYSTEM FOR ALERTING CAREGIVERS

(75) Inventors: Williams F. Collins, Jr., Columbus, IN (US); James Maurice Allen, Batesville, IN (US); Keith A. Huster, Sunman, IN (US); Carl W. Riley, Milan, IN (US); Patricia Anne Glidewell, Apex, NC (US); Irvin J. Vanderpohl, Greensburg, IN (US); Richard J. Schuman, Cary, NC (US); Christopher A. Mathura, Cary, NC (US)

(73) Assignee: Hill-Rom Services, Inc., Wilmington, DE (US)

( * ) Notice: Subject to any disclaimer, the term of this patent is extended or adjusted under 35 U.S.C. 154(b) by 259 days.

(21) Appl. No.: 11/189,781

(22) Filed: Jul. 27, 2005

(65) Prior Publication Data
US 2006/0049936 A1 Mar. 9, 2006

Related U.S. Application Data

(60) Provisional application No. 60/652,699, filed on Feb. 14, 2005, provisional application No. 60/642,692, filed on Jan. 10, 2005, provisional application No. 60/598,045, filed on Aug. 2, 2004.

(51) Int. Cl.
G08B 1/08 (2006.01)
(52) U.S. Cl. .............................. 340/539.12; 340/573.1; 340/506; 340/517; 340/521; 340/524; 340/525; 340/539.11; 340/286.07; 340/825.19

(58) Field of Classification Search ............. 340/573.1, 340/506, 517, 521, 524, 525, 539.1, 539.11, 340/539.12, 286.02, 286.07, 825.19
See application file for complete search history.

(56) References Cited

U.S. PATENT DOCUMENTS

| 2,330,356 A | 9/1943 | Belliveau |
| 2,335,524 A | 11/1943 | Lomax |
| 2,736,888 A | 2/1956 | McLain |
| 2,896,021 A | 7/1959 | Philipps |
| 3,098,220 A | 7/1963 | De Graaf |
| 3,439,320 A | 4/1969 | Ward |
| 3,478,344 A | 11/1969 | Schwitzgebel et al. |
| 3,553,383 A | 1/1971 | Rochtus |

(Continued)

FOREIGN PATENT DOCUMENTS

WO WO 02/091297 A1 11/2002

(Continued)

*Primary Examiner*—Daryl C Pope
(74) *Attorney, Agent, or Firm*—Barnes & Thornburg LLP

(57) ABSTRACT

A system that monitors various conditions of a plurality of hospital beds located in different rooms of a healthcare facility is provided. Alternatively or additionally, other types of equipment may be monitored by the system. Various configurations of network interface units that are coupleable to or integrated into a hospital bed are also disclosed. The system receives data from the hospital beds and/or other equipment and initiates a communication to a wireless communication device of at least one designated caregiver in response to the received data being indicative of an alarm condition.

46 Claims, 23 Drawing Sheets

U.S. PATENT DOCUMENTS

| | | |
|---|---|---|
| 3,599,199 A | 8/1971 | Bunting |
| 3,599,200 A | 8/1971 | Bunting |
| 3,696,384 A | 10/1972 | Lester |
| 3,739,329 A | 6/1973 | Lester |
| 3,767,859 A | 10/1973 | Doering et al. |
| 3,805,265 A | 4/1974 | Lester |
| 3,913,153 A | 10/1975 | Adams et al. |
| 3,973,200 A | 8/1976 | Akerberg |
| 4,067,005 A | 1/1978 | Levy et al. |
| 4,150,284 A | 4/1979 | Trenkler et al. |
| 4,151,407 A | 4/1979 | McBride et al. |
| 4,183,015 A | 1/1980 | Drew et al. |
| 4,216,462 A | 8/1980 | McGrath et al. |
| 4,225,953 A | 9/1980 | Simon et al. |
| 4,228,426 A | 10/1980 | Roberts |
| 4,237,344 A * | 12/1980 | Moore .......................... 379/38 |
| 4,264,982 A | 4/1981 | Sakarya |
| 4,275,385 A | 6/1981 | White |
| 4,279,433 A | 7/1981 | Petaja |
| 4,298,863 A | 11/1981 | Natitus et al. |
| 4,331,953 A | 5/1982 | Blevins et al. |
| 4,356,475 A | 10/1982 | Neumann et al. |
| 4,418,334 A | 11/1983 | Burnett |
| 4,455,548 A | 6/1984 | Burnett |
| 4,489,387 A | 12/1984 | Lamb et al. |
| 4,495,495 A | 1/1985 | Ormanns et al. |
| 4,495,496 A | 1/1985 | Miller, III |
| 4,539,560 A | 9/1985 | Fleck et al. |
| 4,577,185 A | 3/1986 | Andersen |
| 4,578,671 A | 3/1986 | Flowers |
| 4,593,273 A | 6/1986 | Narcisse |
| 4,598,275 A | 7/1986 | Ross et al. |
| 4,601,064 A | 7/1986 | Shipley |
| 4,649,385 A | 3/1987 | Aires et al. |
| 4,680,790 A | 7/1987 | Packard et al. |
| 4,709,330 A | 11/1987 | Yokoi et al. |
| 4,740,788 A | 4/1988 | Konneker |
| 4,752,951 A | 6/1988 | Konneker |
| 4,792,798 A | 12/1988 | Wilowski |
| 4,795,905 A | 1/1989 | Zierhut |
| 4,814,751 A | 3/1989 | Hawkins et al. |
| 4,833,452 A | 5/1989 | Currier |
| 4,833,467 A | 5/1989 | Kobayashi et al. |
| 4,837,568 A | 6/1989 | Snaper |
| 4,853,692 A | 8/1989 | Wolk et al. |
| 4,899,135 A | 2/1990 | Chahariiran |
| 4,947,152 A | 8/1990 | Hodges |
| 4,955,000 A | 9/1990 | Nastrom |
| 4,967,195 A | 10/1990 | Shipley |
| 4,990,892 A | 2/1991 | Guest et al. |
| 4,998,095 A | 3/1991 | Shields |
| 4,998,939 A | 3/1991 | Potthast et al. |
| 5,006,830 A | 4/1991 | Merritt |
| 5,027,314 A | 6/1991 | Linwood et al. |
| 5,041,086 A | 8/1991 | Koenig et al. |
| 5,062,151 A | 10/1991 | Shipley |
| 5,065,154 A | 11/1991 | Kaiser |
| 5,086,290 A | 2/1992 | Murray et al. |
| 5,103,108 A | 4/1992 | Crimmins |
| 5,124,991 A | 6/1992 | Allen |
| 5,137,033 A | 8/1992 | Norton |
| 5,153,584 A | 10/1992 | Engira |
| 5,266,944 A | 11/1993 | Carroll et al. |
| 5,291,399 A | 3/1994 | Chaco |
| 5,319,355 A | 6/1994 | Russek |
| 5,319,363 A * | 6/1994 | Welch et al. .......... 340/825.36 |
| 5,357,254 A | 10/1994 | Kah, Jr. |
| 5,375,604 A | 12/1994 | Kelly et al. |
| 5,396,224 A | 3/1995 | Dukes et al. |
| 5,396,227 A | 3/1995 | Carroll et al. |
| 5,416,695 A | 5/1995 | Stutman et al. |
| 5,434,775 A | 7/1995 | Sims et al. |
| 5,446,678 A | 8/1995 | Saltzstein et al. |
| 5,455,560 A | 10/1995 | Owen |
| 5,458,123 A | 10/1995 | Unger |
| 5,461,390 A | 10/1995 | Hoshen |
| 5,475,367 A | 12/1995 | Prevost |
| 5,534,851 A | 7/1996 | Russek |
| 5,537,459 A * | 7/1996 | Price et al. ............... 455/435.1 |
| 5,548,637 A | 8/1996 | Heller et al. |
| 5,549,113 A | 8/1996 | Halleck et al. |
| 5,561,412 A | 10/1996 | Novak et al. |
| 5,568,119 A | 10/1996 | Schipper et al. |
| 5,576,452 A * | 11/1996 | Dever et al. ................. 556/130 |
| 5,576,952 A | 11/1996 | Stutman et al. |
| 5,579,001 A | 11/1996 | Dempsey et al. |
| 5,588,005 A | 12/1996 | Ali et al. |
| 5,594,786 A | 1/1997 | Chaco et al. |
| 5,621,388 A | 4/1997 | Sherburne et al. |
| 5,635,907 A | 6/1997 | Bernard et al. |
| 5,636,245 A | 6/1997 | Ernst et al. |
| 5,640,953 A | 6/1997 | Bishop et al. |
| 5,650,769 A | 7/1997 | Campana, Jr. |
| 5,650,770 A | 7/1997 | Schlager et al. |
| 5,664,270 A | 9/1997 | Bell et al. |
| 5,682,139 A | 10/1997 | Pradeep et al. |
| 5,686,888 A | 11/1997 | Welles, II |
| 5,686,902 A | 11/1997 | Reis et al. |
| 5,687,734 A | 11/1997 | Dempsey et al. |
| 5,689,229 A * | 11/1997 | Chaco et al. .......... 340/286.07 |
| 5,691,980 A | 11/1997 | Welles, II et al. |
| 5,699,038 A | 12/1997 | Ulrich et al. |
| 5,705,980 A | 1/1998 | Shapiro |
| 5,708,421 A | 1/1998 | Boyd |
| 5,713,856 A | 2/1998 | Eggers et al. |
| 5,719,761 A | 2/1998 | Gatti et al. |
| 5,731,757 A | 3/1998 | Layson, Jr. |
| 5,742,237 A | 4/1998 | Bledsoe |
| 5,751,246 A | 5/1998 | Hertel |
| 5,752,917 A | 5/1998 | Fuchs |
| 5,760,704 A | 6/1998 | Barton et al. |
| 5,767,791 A | 6/1998 | Stoop et al. |
| 5,781,442 A | 7/1998 | Engleson et al. |
| 5,793,290 A | 8/1998 | Eagleson et al. |
| 5,808,564 A | 9/1998 | Simms et al. |
| 5,812,056 A | 9/1998 | Law |
| 5,822,418 A | 10/1998 | Yacenda et al. |
| 5,822,544 A | 10/1998 | Chaco et al. |
| 5,838,223 A | 11/1998 | Gallant et al. |
| 5,844,488 A | 12/1998 | Musick |
| 5,867,821 A | 2/1999 | Ballantyne et al. |
| 5,877,675 A | 3/1999 | Rebstock et al. |
| 5,933,488 A | 8/1999 | Marcus et al. |
| 5,936,539 A | 8/1999 | Fuchs |
| 5,942,986 A | 8/1999 | Shabot et al. |
| 5,944,659 A | 8/1999 | Flach et al. |
| 5,963,137 A | 10/1999 | Waters, Sr. |
| 5,974,389 A | 10/1999 | Clark et al. |
| 5,991,728 A | 11/1999 | DeBusk et al. |
| 5,995,937 A | 11/1999 | DeBusk et al. |
| 6,014,633 A | 1/2000 | DeBusk et al. |
| 6,057,758 A | 5/2000 | Dempsey et al. |
| 6,057,782 A | 5/2000 | Koenig |
| 6,067,019 A | 5/2000 | Scott |
| 6,076,166 A | 6/2000 | Moshfeghi et al. |
| 6,085,493 A | 7/2000 | DeBusk et al. |
| 6,088,362 A | 7/2000 | Turnbull et al. |
| 6,093,146 A | 7/2000 | Filangeri |
| 6,097,308 A | 8/2000 | Albert et al. |
| 6,125,350 A * | 9/2000 | Dirbas .......................... 705/2 |
| 6,133,837 A | 10/2000 | Riley |
| 6,147,592 A | 11/2000 | Ulrich et al. |
| 6,183,417 B1 | 2/2001 | Geheb et al. |
| 6,208,250 B1 | 3/2001 | Dixon et al. |

| | | |
|---|---|---|
| 6,241,668 B1 | 6/2001 | Herzog |
| 6,259,355 B1 | 7/2001 | Chaco et al. |
| 6,264,614 B1 | 7/2001 | Albert et al. |
| 6,279,183 B1 | 8/2001 | Kummer et al. |
| 6,287,253 B1 | 9/2001 | Ortega et al. |
| 6,302,844 B1 | 10/2001 | Walker et al. |
| 6,314,556 B1 | 11/2001 | DeBusk et al. |
| 6,320,510 B2 | 11/2001 | Menkedick et al. |
| 6,344,794 B1 | 2/2002 | Ulrich et al. |
| 6,348,777 B1 | 2/2002 | Brown et al. |
| 6,362,725 B1 | 3/2002 | Ulrich et al. |
| 6,364,834 B1 | 4/2002 | Reuss et al. |
| 6,398,727 B1 | 6/2002 | Bui et al. |
| 6,406,426 B1 | 6/2002 | Reuss et al. |
| 6,407,335 B1 | 6/2002 | Franklin-Lees et al. |
| 6,412,980 B1 | 7/2002 | Lounsberry et al. |
| 6,416,471 B1 | 7/2002 | Kumar et al. |
| 6,421,649 B1 | 7/2002 | Rattner |
| 6,439,769 B1 | 8/2002 | Polkus et al. |
| 6,441,742 B1 | 8/2002 | Lovely et al. |
| 6,442,290 B1 | 8/2002 | Ellis et al. |
| 6,445,299 B1 | 9/2002 | Rojas, Jr. |
| 6,450,956 B1 | 9/2002 | Rappaport et al. |
| 6,462,656 B2 | 10/2002 | Ulrich et al. |
| 6,486,792 B1 | 11/2002 | Moster et al. |
| 6,493,568 B1 | 12/2002 | Bell et al. |
| 6,494,831 B1 | 12/2002 | Koritzinsky |
| 6,510,344 B1 | 1/2003 | Halpern |
| 6,516,324 B1 | 2/2003 | Jones et al. |
| 6,526,310 B1 | 2/2003 | Carter et al. |
| 6,529,164 B1 | 3/2003 | Carter |
| 6,533,453 B1 | 3/2003 | Heidsieck et al. |
| 6,535,576 B2 | 3/2003 | Vafi et al. |
| 6,539,393 B1 | 3/2003 | Kabala |
| 6,544,173 B2 | 4/2003 | West et al. |
| 6,544,174 B2 | 4/2003 | West et al. |
| 6,551,243 B2 | 4/2003 | Bocionek et al. |
| 6,553,106 B1 | 4/2003 | Gould et al. |
| 6,554,174 B1 | 4/2003 | Aceves |
| 6,556,630 B1 | 4/2003 | Brinsfield et al. |
| 6,560,274 B1 | 5/2003 | Leitgeb et al. |
| 6,572,556 B2 | 6/2003 | Stoycos et al. |
| 6,575,901 B2 | 6/2003 | Stoycos et al. |
| 6,581,204 B2 | 6/2003 | DeBusk et al. |
| 6,584,182 B2 | 6/2003 | Brodnick |
| 6,584,454 B1 | 6/2003 | Hummel, Jr. et al. |
| 6,585,645 B2 | 7/2003 | Hutchinson |
| 6,589,170 B1 | 7/2003 | Flach et al. |
| 6,593,528 B2 | 7/2003 | Franklin-Lees et al. |
| 6,594,146 B2 | 7/2003 | Frangesch et al. |
| 6,594,519 B2 | 7/2003 | Stoycos et al. |
| 6,600,421 B2 | 7/2003 | Freeman |
| 6,603,494 B1 | 8/2003 | Banks et al. |
| 6,609,115 B1 | 8/2003 | Mehring et al. |
| 6,616,606 B1 | 9/2003 | Petersen et al. |
| 6,622,088 B2 | 9/2003 | Hood |
| 6,640,246 B1 | 10/2003 | Gary, Jr. et al. |
| 6,643,238 B2 | 11/2003 | Nakajima |
| 6,650,346 B1 | 11/2003 | Jaeger et al. |
| 6,659,947 B1 | 12/2003 | Carter et al. |
| 6,665,385 B2 | 12/2003 | Rogers et al. |
| 6,665,820 B1 | 12/2003 | Frowein et al. |
| 6,669,630 B1 | 12/2003 | Joliat et al. |
| 6,671,547 B2 | 12/2003 | Lyster et al. |
| 6,671,563 B1 | 12/2003 | Engelson et al. |
| 6,685,633 B2 | 2/2004 | Albert et al. |
| 6,689,091 B2 | 2/2004 | Bui et al. |
| 6,694,367 B1 | 2/2004 | Miesbauer et al. |
| 6,694,509 B1 | 2/2004 | Stoval et al. |
| 6,697,765 B2 | 2/2004 | Kuth |
| 6,707,476 B1 | 3/2004 | Hochstedler |
| 6,714,913 B2 | 3/2004 | Brandt et al. |
| 6,721,818 B1 | 4/2004 | Nakamura |
| 6,726,634 B2 | 4/2004 | Freeman |
| 6,727,818 B1 | 4/2004 | Wildman et al. |
| 6,731,311 B2 | 5/2004 | Bufe et al. |
| 6,731,989 B2 | 5/2004 | Engleson et al. |
| 6,740,033 B1 | 5/2004 | Olejniczak et al. |
| 6,749,566 B2 | 6/2004 | Russ |
| 6,751,630 B1 | 6/2004 | Franks et al. |
| 6,754,545 B2 | 6/2004 | Haeuser et al. |
| 6,754,883 B2 | 6/2004 | DeBusk et al. |
| 6,759,959 B2 | 7/2004 | Wildman |
| 6,763,541 B2 | 7/2004 | Mahoney et al. |
| 6,771,172 B1 | 8/2004 | Robinson et al. |
| 6,773,396 B2 | 8/2004 | Flach et al. |
| 6,778,225 B2 | 8/2004 | David |
| 6,781,517 B2 | 8/2004 | Moster et al. |
| 6,784,797 B2 | 8/2004 | Smith et al. |
| 6,791,460 B2 | 9/2004 | Dixon et al. |
| 6,792,396 B2 | 9/2004 | Inda et al. |
| 6,801,227 B2 | 10/2004 | Bocionek et al. |
| 6,807,543 B2 | 10/2004 | Muthya |
| 6,825,763 B2 | 11/2004 | Ulrich et al. |
| 6,826,578 B2 | 11/2004 | Brackett et al. |
| 6,828,992 B1 | 12/2004 | Freeman et al. |
| 6,829,796 B2 | 12/2004 | Salvatini et al. |
| 6,830,549 B2 | 12/2004 | Bui et al. |
| 6,832,199 B1 | 12/2004 | Kucek et al. |
| 6,840,117 B2 | 1/2005 | Hubbard, Jr. |
| 6,847,814 B1 | 1/2005 | Vogeleisen |
| 6,868,256 B2 | 3/2005 | Dooley et al. |
| 6,871,211 B2 | 3/2005 | Labounty et al. |
| 6,873,884 B2 | 3/2005 | Brackett et al. |
| 6,876,303 B2 * | 4/2005 | Reeder et al. ........... 340/573.1 |
| 6,876,985 B2 | 4/2005 | Kawanaka |
| 6,885,288 B2 | 4/2005 | Pincus |
| 6,891,909 B2 | 5/2005 | Hurley et al. |
| 6,904,161 B1 | 6/2005 | Becker et al. |
| 6,909,995 B2 | 6/2005 | Shiraishi |
| 6,912,549 B2 | 6/2005 | Rotter et al. |
| 6,915,170 B2 | 7/2005 | Engleson et al. |
| 6,925,367 B2 | 8/2005 | Fontius |
| 6,930,878 B2 | 8/2005 | Brackett et al. |
| 6,958,706 B2 * | 10/2005 | Chaco et al. ........... 340/870.11 |
| 7,068,143 B2 | 6/2006 | Doering et al. |
| 7,092,376 B2 * | 8/2006 | Schuman .................... 370/349 |
| 7,138,902 B2 * | 11/2006 | Menard ..................... 340/5.53 |
| 2001/0050610 A1 | 12/2001 | Gelston |
| 2001/0051765 A1 | 12/2001 | Walker et al. |
| 2002/0014951 A1 | 2/2002 | Kramer et al. |
| 2002/0044043 A1 | 4/2002 | Chaco et al. |
| 2002/0044059 A1 | 4/2002 | Reeder et al. |
| 2002/0067273 A1 | 6/2002 | Jaques et al. |
| 2002/0070867 A1 | 6/2002 | Conway et al. |
| 2002/0080037 A1 | 6/2002 | Dixon et al. |
| 2002/0103674 A1 | 8/2002 | Reeder et al. |
| 2002/0151990 A1 | 10/2002 | Ulrich et al. |
| 2002/0173991 A1 | 11/2002 | Avitall |
| 2002/0186136 A1 | 12/2002 | Schuman |
| 2002/0196141 A1 | 12/2002 | Boone et al. |
| 2003/0010345 A1 | 1/2003 | Koblasz et al. |
| 2003/0028449 A1 | 2/2003 | Heinen et al. |
| 2003/0030569 A1 | 2/2003 | Ulrich et al. |
| 2003/0052787 A1 | 3/2003 | Zerhusen et al. |
| 2003/0074222 A1 | 4/2003 | Rosow et al. |
| 2003/0146835 A1 | 8/2003 | Carter |
| 2003/0149598 A1 | 8/2003 | Santoso et al. |
| 2003/0176798 A1 | 9/2003 | Simon |
| 2003/0206116 A1 | 11/2003 | Weiner et al. |
| 2004/0183681 A1 | 9/2004 | Smith |
| 2004/0183684 A1 | 9/2004 | Callaway |

| | | |
|---|---|---|
| 2004/0186358 A1 | 9/2004 | Chernow et al. |
| 2004/0193449 A1 | 9/2004 | Wildman et al. |
| 2005/0035862 A1 | 2/2005 | Wildman et al. |
| 2005/0242946 A1 | 11/2005 | Hubbard, Jr. et al. |

FOREIGN PATENT DOCUMENTS

WO    WO 2004/036390 A2    4/2004

\* cited by examiner

| WHITEBOARD | Room | Patient Name | Nurse | Nurse # | Call | Page | Attending |
|---|---|---|---|---|---|---|---|
| | 101A | Da...Ma | Amy M | 4356 | ☎ | 📟 | Dr. Roark |
| | 101B | Le...Ak | Mary S | 4322 *192* | ☎ | 📟 *194* | Dr. Smith |
| | 102A | De...Se | Nancy W | 4332 | ☎ | 📟 | Dr. Liewelyn |
| | 102B | Ba...De | John S | 4553 | ☎ | 📟 | Dr. Roark |
| | 103A | Ma...Le | Lewis B | 4321 *192* | ☎ | 📟 | Dr. Smith |
| | 103B | Ty...De | Amy M | 4356 | ☎ | 📟 *194* | Dr. Liewelyn |
| | 104A | Ha...Ma | Mary S | 4322 | ☎ | 📟 | Dr. Roark |
| | 105A | Me...Sa | Nancy W | 4312 | ☎ | 📟 | Dr. Liewelyn |
| | 105B | Ta...De | Nancy W | 4312 | ☎ | 📟 | Dr. Roark |
| | 106A | Mo...Le | Amy M | 4356 | ☎ | 📟 *194* | Dr. Smith |
| | 106B | Pa...De | Mary S | 4332 | ☎ | 📟 *192* | Dr. Liewelyn |
| | 107A | Et...Ma | Mary S | 4332 | ☎ | 📟 | Dr. Roark |
| | 107B | Le...Ak | | | | | Dr. Smith |

Nurse Supervisor: Mary Smith #4332   Respiratory Therapist: John Cox, M.D. #3543
Transporter: John Doe #2335   Pharmacist: William Herring #1432

CONFIGURABLE SYSTEM FOR ALERTING CAREGIVERS

This application claims the benefit, under 35 U.S.C. § 119(e), of U.S. Provisional Patent Application Ser. No. 60/652,699 filed Feb. 14, 2005; of U.S. Provisional Patent Application Ser. No. 60/642,692 filed Jan. 10, 2005; and of U.S. Provisional Patent Application Ser. No. 60/598,045 filed Aug. 2, 2004; each of which is hereby incorporated by reference herein in its entirety.

BACKGROUND OF THE INVENTION

The present disclosure relates to systems that monitor equipment and/or patients in hospital rooms and that alert caregivers to alarm conditions. More particularly, the present disclosure relates to systems that monitor equipment, such as hospital beds, and that communicate via a network of a healthcare facility with computers at nurse call stations and with caregivers carrying one or more communication devices.

Equipment in hospitals and other healthcare facilities sometimes communicate the status of the equipment via a network to a computer located at a nurse station or other location in the facility. If an alarm condition is detected, some sort of notification of the condition causing the alarm is shown on the display screen of the computer. See, for example, the network disclosed in U.S. Pat. No. 5,319,363 in which a number of different patient care devices provide information to a workstation at a nurse's station. Hospital beds are another example of equipment that sometimes communicates information via a network to a computer at a nurse's station. See, for example, U.S. Pat. Nos. 5,561,412 and 5,699,038. Caregivers sometimes wear or carry badges that communicate wirelessly with the network of the healthcare facility. Information from the badges, and from receivers with which the badges communicate, sometimes is used to determine the location of caregivers in the healthcare facility. Some caregivers may carry other wireless communication devices, such as pagers, wireless telephone handsets, personal digital assistants (PDA's), and other types of voice communication devices.

After a nurse at the master nurse's station sees that an alarm condition exists, the nurse may contact another caregiver assigned to a patient associated with the alarm condition so that the contacted caregiver can attend to the alarm condition. Thus, such systems require one person to take action to contact another person to attend to the alarm condition. The nurse at the master nurse's station may sometimes contact caregivers about alarm conditions that are not of consequence to the care of the associated patient and about which the contacted caregiver would prefer not to have been notified. U.S. Pat. No. 5,319,355 discloses a system in which alarm conditions detected by various pieces of equipment are transmitted to a master alarm control which then automatically communicates information about all received alarm conditions to pagers carried by designated caregivers, unless an operator at the master alarm interrupts the transmission of an alarm after it is received at the master alarm control. In such a system, the pieces of equipment at disparate locations determine their own alarm conditions and when an alarm condition occurs, the assigned caregivers are notified via their pagers. Thus, the caregivers may be paged about alarm conditions that do not require the attention of the caregiver. Receiving undesired notifications of alarm conditions may reduce the productivity of caregivers.

SUMMARY OF THE INVENTION

The present invention comprises a system and/or method that has one or more of the following features and/or steps, which alone or in any combination may comprise patentable subject matter:

The system may comprise at least one computer device operable to display template screens that permit users to configure the types of alarms to which one or more caregivers are to be alerted. The template screens may include a list of the conditions of the equipment being monitored which can be selected on the template screen, via selection of a check box, radio button, or the like, so that when the condition is met, the system alerts one or more caregivers to the alarm condition. In some instances, one or more numerical quantities representing associated alarm condition thresholds may be entered on the template screen. Alarm conditions may be considered to exist when a monitored condition is equal to, not equal to, greater than, greater than or equal to, less than, or less than or equal to the associated alarm condition thresholds. The system may be configured to permit users to create new template screens in which alert conditions of the user's choosing may be included on the user-created template. The template screens may permit users to select the level of priority, such as high, normal, or low, to be assigned to one or more particular alert conditions. The system may be configured so that, when an alarm condition associated with a particular patient or piece of equipment occurs, the system automatically sends a message to notify a primary caregiver of the alarm condition.

The automatic notification may be an alphanumeric message sent to a portable wireless communication device, such as a pager, PDA, wireless communication badge, wireless phone handset, or any other portable wireless device having text messaging capability. Alternatively or additionally, the automatic notification may be a system-generated audio message to a portable wireless communication device, such as those mentioned previously, or to one or more system-selected audio stations which are located throughout a healthcare facility, typically near patient beds. The system may determine which audio station should provide the audio message to the caregiver based on information from a locating-and-tracking portion of a system which monitors the whereabouts of caregivers in a healthcare facility.

If the system is unable to locate the primary caregiver within a predetermined period of time, or if the primary caregiver does not respond to the system's attempt to notify the primary caregiver of the alarm condition within a predetermined period of time, then the system may operate to automatically notify a secondary caregiver of the alarm condition in any of the manners just described. The system may have screens on which users can indicate the manner in which the primary caregiver, secondary caregiver, and other caregivers are to be notified when the system receives data indicative that an alarm condition exists. For example, users may configure the system so that the primary caregiver is notified of an alarm condition by an audio message sent to the primary caregiver's wireless communication badge and so that the secondary caregiver is notified of the alarm condition by sending an alphanumeric message to the secondary caregiver's pager. The system may be configured such that notification of alarm conditions are not generated by the system automatically, but rather, alarm conditions are communicated to the primary and secondary caregivers by a person at the master nurse call station. One or more screens at the master nurse call station may have icons, such as a call icon or a page icon, that the user selects to send the alarm notification. Alternatively or additionally, the system may be configured such that a person at the master nurse call station is permitted a period of time to contact a primary or secondary caregiver about the alarm condition, and if the period of time elapses, then the system automatically initiates communication of the alarm notification to the primary or secondary caregiver's portable wireless communication device.

The system may monitor various conditions of a plurality of hospital beds located in different rooms of a healthcare facility. The system may comprise software that, when executed, causes any one or more of the following types of information to be displayed on a computer screen: a floor plan showing each room of at least a portion of the healthcare facility; color coding to indicate the status of each room; the color coding may, for example, show a room in green if the room is ready (or a portion thereof, for multi-occupant rooms) to receive a patient, show a room in yellow if the room (or a portion thereof needs to be cleaned), or show red if an alarm condition is occurring in the hospital room (or a portion thereof); an image of a hospital bed with portions of the bed being color coded to indicate an alarm condition associated with the colored portion of the image; information about the condition of the bed, such as head section angle, the status of a bed exit alarm (or a patient position monitoring system included in the bed), the height of an upper frame of the bed relative to a base frame, whether the siderails are up or down, the status of a therapy of a surface of the bed (such as percussion therapy, lateral rotation therapy, alternating pressure therapy), the status of a turn assist function of the mattress, the status of an inflatable vest which is inflated via components included on the bed, whether the bed is receiving power from a wall outlet, and whether certain functions of the bed are locked out or disabled; event notification information, such as the type(s) of events for which notification is to be given (for example, siderail lowered, head section raised beyond a certain angle, bed exit detected), any reminders regarding checking in on patients periodically; patient information such as a patient's name, the patient's primary caregiver, the patient's secondary caregiver, the room to which the patient is assigned, whether the patient is a fall risk, whether the patient is being restrained, and other notes about the patient or the patient's condition; and a caregiver's location in the healthcare facility.

The system may communicate via a network of the healthcare facility with any one or more of the following: an electronic medical records database, a nurse call badge, a nurse location badge, a workflow management system, a personal data assistant (PDA), a voice communication badge, a badge having text message capability, a combination badge which performs a combination of functions of the badges already listed, a wireless telephone handset, and a pager.

The system may cause an image, or a portion of an image, to flash when an alarm condition or alert condition associated with the image is occurring. The terms "alarm" and "alert" are used interchangeably herein and each of these terms is intended to cover the meanings of both. The system may cause the image or portion of the image to cease flashing when the system detects via data from a nurse locating and tracking portion of the system that a caregiver has entered the room in which the alarm condition is occurring. If the system detects that the caregiver has exited the room without rectifying the alarm condition, the system may notify the caregiver via an audio alarm (such as a voice message), a visual alarm (such as a text message), or other type of alarm (such as vibrations), which are communicated to the caregiver via a badge, PDA, pager, or other portable wireless device carried by the caregiver.

The system may be configurable such that when the location and tracking portion of the system detects that a particular caregiver (or type of caregiver) has entered a particular room, or otherwise is in close proximity to the bed, various functions of the bed will automatically be disabled and/or enabled and/or modified by the system. Thus, the bed may be configured automatically by the system for the caregiver without the caregiver having to press or otherwise manipulate any controls on the bed. Examples of functions that may be functionally modified in response to detection of caregiver presence include motor control access, confidential data access, Standard of Care Notification, therapy controls, and nurse call system access.

A system for alerting caregivers of alarm conditions in a healthcare facility may comprise a computer device that is programmable by caregivers to designate a first set of alarm conditions to which the caregiver is to be alerted during a first period of time and to designate a second set of alarm conditions to which the caregiver is to be alerted during a second period of time. The first period of time and the second period of time may partially overlap, or the second period of time may begin upon the expiration of the first time period, or the first and second time periods may be separated by an interim time period. At least one of the first and second time periods may begin or end in response to detection by the system of a predetermined condition. At least one of the first and second time periods may begin or end at a predetermined time. Some of the alarm conditions of the first set may also be included in the second set. At least one of the alarm conditions of the first set may be considered to exist when a monitored condition is equal to, not equal to, greater than, greater than or equal to, less than, or less than or equal to a first threshold and one of the alarm conditions of the second set may be considered to exist when the monitored alarm conditions is equal to, not equal to, greater than, greater than or equal, less than, or less than or equal to a second threshold that is different than the first threshold. The system may communicate a reminder to at least one caregiver a preset amount of time before or after the expiration of the first period of time. The first set of alarm conditions may be based on a first Standard of Care for a patient and the second set of alarm conditions may be based on a second Standard of Care for the patient.

A system according to this disclosure may comprise a hospital bed which has circuitry that monitors a plurality of bed parameters and at least one computer spaced from the hospital bed. The at least one computer may be operable to permit caregivers to designate alarm thresholds for a subset of the plurality of bed parameters. The at least one computer may communicate to the hospital bed the types of bed parameters of the subset for which alarm thresholds have been designated. The hospital bed may operate to communicate to the at least one computer device data associated with the subset and the hospital bed may refrain from communicating to the at least one computer data associated with other bed parameters not in the subset. The at least one computer device may communicate to the hospital bed at least some of the alarm thresholds. The bed may operate to monitor the subset of bed parameters and to communicate to the at least one computer device an alarm signal indicating that an alarm condition has been detected based on a comparison of at least one of the alarm thresholds to the associated bed parameter.

A network interface unit may be coupleable to bed communications circuitry of a hospital bed and may be configured to communicate data via a data link to a hospital Ethernet. The data link may comprise a wired data link, a wireless data link, or both. The network interface unit may be configured to convert data received from the bed in a format according to a first protocol into a format according to a second protocol, such as an Ethernet protocol. The network interface unit may be coupled to a legacy (i.e., existing) nurse call system and data formatted according to the first protocol may be fed through the network interface unit and communicated to the legacy nurse call system while remaining formatted according to the first protocol.

A hospital bed contemplated by this disclosure may comprise bed control circuitry for controlling a plurality functions of the bed and for monitoring at least some of the plurality of functions. The hospital bed may also comprise a network interface circuit that is coupleable to a hospital Ethernet via a data link. The data link may comprise a wired data link, a wireless data link, or both. The network interface circuit may be configured to format data received from the bed control circuitry into a format according to an Ethernet protocol.

A system according to this disclosure may comprise at least one nurse call computer device coupled to a hospital Ethernet which may have at least one wired access point and at least on wireless access point. The system may comprise a hospital bed having associated therewith bed identification (ID) data. The system may also comprise a network interface unit (NIU) coupled to the bed via a first data link. The NIU may have associated therewith NIU ID data. The NIU may have a communications port that is coupleable to the Ethernet via a second data link. The NIU may be configured to sense whether the communications port is coupled to the Ethernet via the second data link. If the NIU is coupled to the Ethernet via the second data link then both the bed ID data received by the NIU and the NIU ID data may be transmitted by the NIU to the Ethernet over the second data link. However, if the NIU is not coupled to the Ethernet via the second data link then the NIU ID data received by the bed may be transmitted wirelessly by the bed to one of the wireless access points of the Ethernet along with the bed ID data.

Additional features, which alone or in combination with any other feature(s), such as those listed above, may comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures, in which:

FIG. 15 is a screen shot of a Whiteboard screen showing an overview of the patients and room status of the associated unit;

DETAILED DESCRIPTION OF THE DRAWINGS

Figure 1:
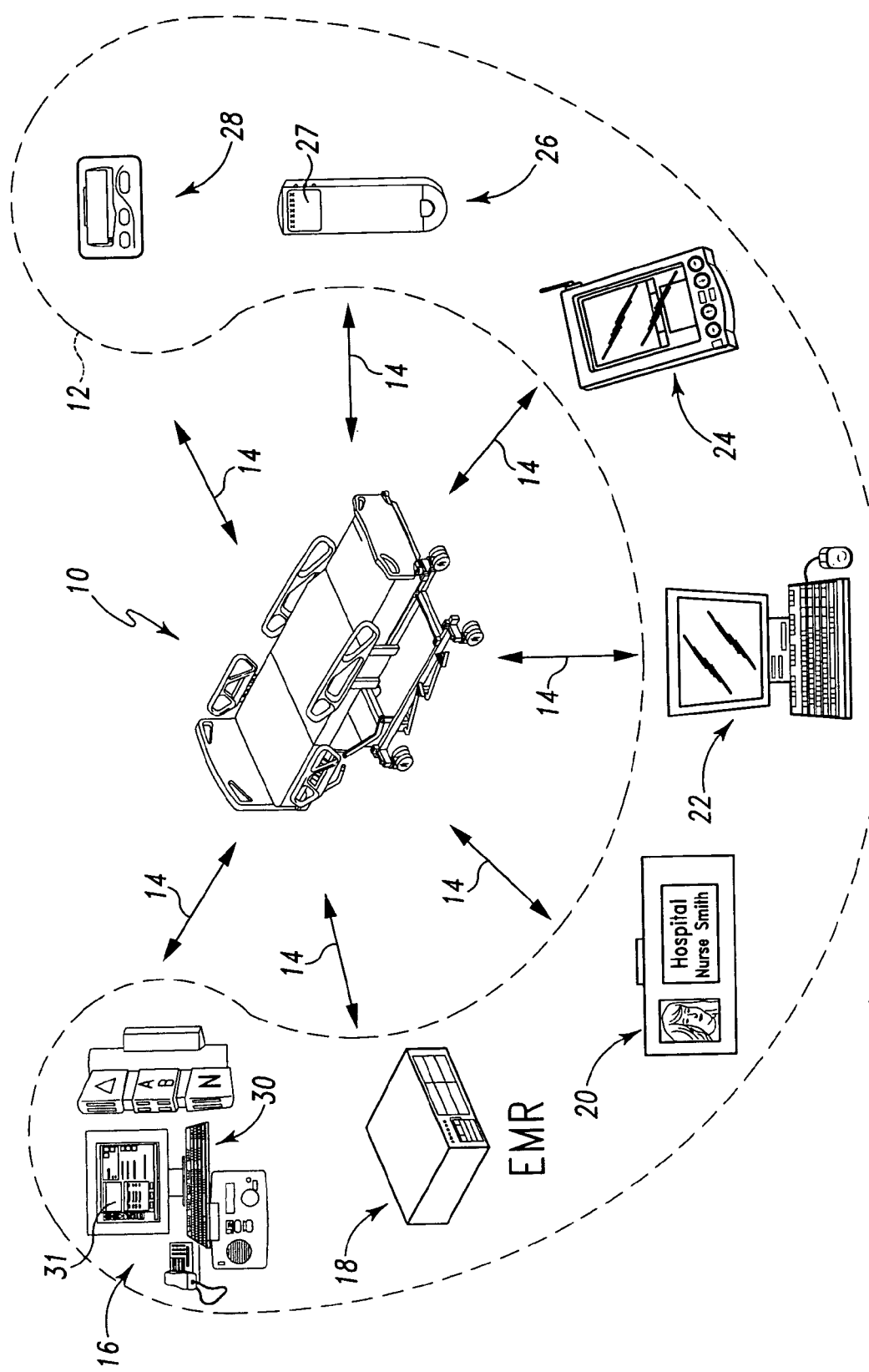
FIG. 1 is a diagrammatic view showing a hospital bed communicating with a number of devices included in a computer network of a healthcare facility.

A hospital bed 10 communicates with a computer network or system 12 of a healthcare facility as indicated diagrammatically in FIG. 1 by double-headed arrows 14. Included in network 12 is a nurse call system 16, an electronic medical record database 18, a nurse call/locating badge 20, one or more computers programmed with workflow process software 22 (such as, for example, NaviCare® software which is available from Hill-Rom Company, Inc.), one or more personal digital assistants (PDA's) 24, one or more voice communications badges 26, and one or more pagers 28. In some embodiments, nurse call system 16 and badges 20 are of the type available as part of the ComLinx™ system from Hill-Rom Company, Inc.

In some embodiments, voice communications badges 26 are of the type available from Vocera Communications, Inc. Illustratively, badge 26 has a text message screen 27 on which various text messages indicative of alarm conditions or other information are displayed. Badges 26 are also configured to audibly communicate system-generated audio messages to caregivers regarding alarm conditions or other information. The communications link 14 between bed 10 and network 12 may be a wired link, a wireless link, or a combination of wired and wireless links. The bed 10 may communicate directly with the respective hardware associated with one or more of system 16, database 18, badges 20, one or more computers operating software 22, PDA's 24, badges 26, and pagers 28, or bed 10 may communicate with each of these via other hardware included in network 12, such as servers, routers, hubs, wireless access points, transceivers, and any other hardware provided by a healthcare facility in its network (e.g., LAN, WAN, and/or Ethernet).

Figure 2:
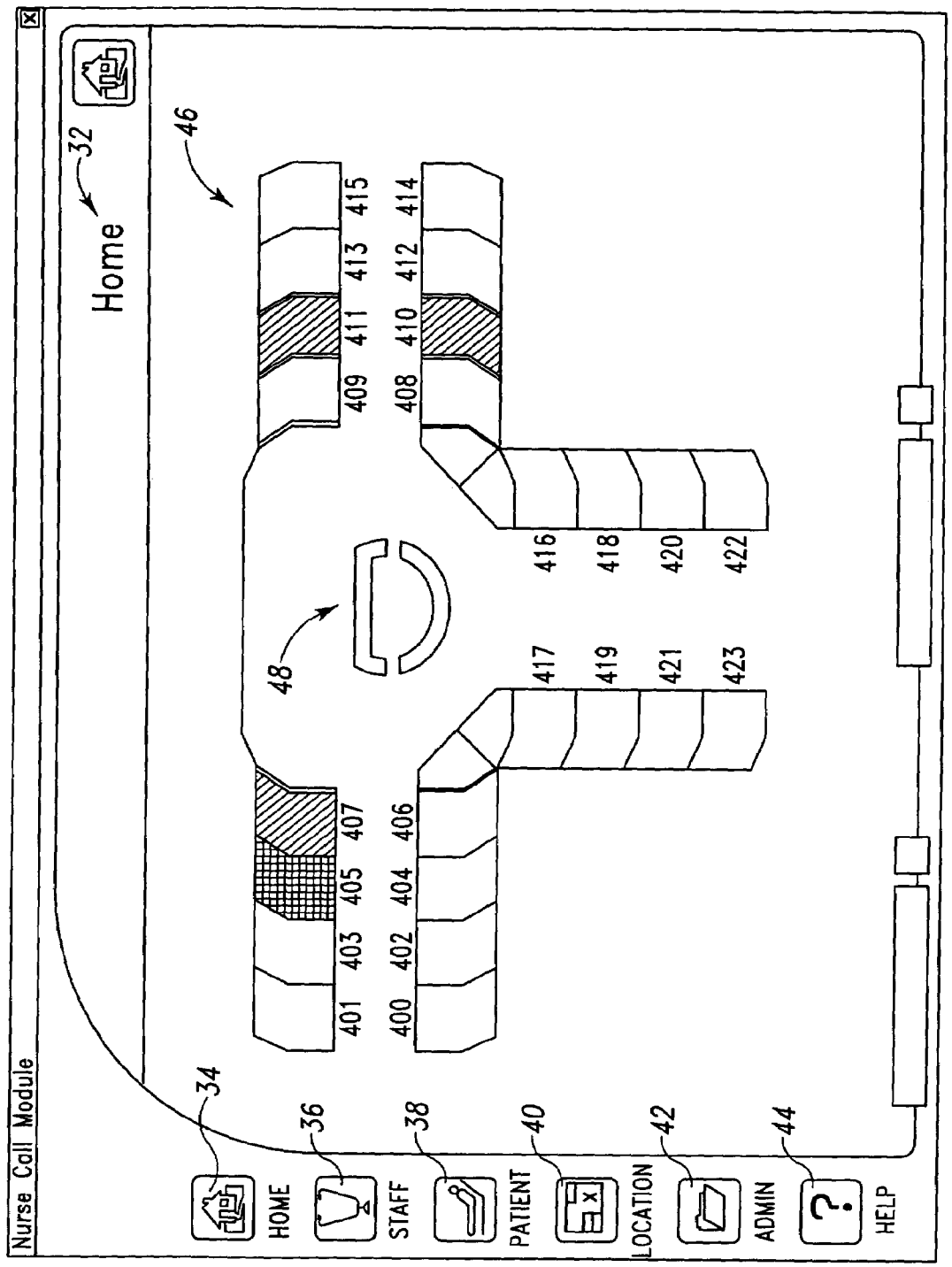
FIG. 2 is a screen shot of a Home screen that appears on a computer in accordance with software included as part of a system according to the present disclosure.

In accordance with this disclosure, one or more computers included in network 12, such as computer 30 of nurse call system 16, is programmed with system software that operates to generate the screen shots shown in FIGS. 2-11. The screen shots of FIGS. 2-11 appear on a display screen 31 associated with computer 30. FIG. 2 is a screen shot of a Home screen 32 that appears on a computer in accordance with the software included as part of a system according to the present disclosure. On the left hand side of Home screen 32 are a menu icon 34, a staff icon 36, a patient icon 38, a location icon 40, an admin icon 42, and a help icon 44. When on any of screens shown in FIGS. 2-9 a user can select any of icons 34, 36, 38, 40, 42, 44 and the system will respond with a screen corresponding to the selected icon. Screen 32 has a floor plan or layout 46 showing a plurality of patient rooms (illustratively, rooms 400 through 423) of a wing of a healthcare facility and showing a master nurse call station 48. The rooms are color coded to indicate certain room conditions. In the illustrative example of FIG. 2, rooms 407, 410, and 411 are color coded green to indicate that the rooms are ready for a patient and room 405 is color coded yellow to indicate that the room needs to be cleaned.

According to this disclosure, a caregiver manipulates an input in a hospital room to indicate to computer 30 (directly or via network 14) whether an associated hospital bed is clean or dirty. In some embodiments, the caregiver signals whether an associated bed is clean or dirty via a menu and user inputs on an audio station in the patient room. For example, the caregiver may scroll on a menu, or otherwise navigate through options on a display screen of the audio station, so that a "bed is dirty" message (or similar message) appears on the display screen of the audio station and then the caregiver presses an enter key or button or moves a switch or touches a designated portion of a touchscreen or otherwise manipulates an input on the audio station to indicate that the bed is dirty. Similarly, the caregiver may scroll or navigate on the audio station menu top a "bed is clean" message and then manipulate the input on the audio station to indicate that the bed is clean.

In other embodiments, the bed clean/dirty status is communicated to computer 30 by a switch or button mounted on a wall in the hospital room, such as a room wall or a wall of a headwall unit. In still other embodiments, a caregiver manipulates a switch or button or menu screen located on the hospital bed, such as on a siderail or a foot board of the hospital bed, for example, to signal computer 30 as to the clean/dirty status of the associated hospital bed. Alternatively or additionally, the bed clean/dirty status of an associated hospital bed may be communicated to computer 30 via wireless voice communication devices, such as badges 26. In such embodiments, a voice recognition system or an interactive voice response system receives verbal statements from the caregiver carrying one of badges 26 (e.g., "Room 103, bed 1 is clean") and converts the verbal statements into electronic data that is transmitted to computer 30 so that the clean/dirty status of the associated bed is updated in a database associated with computer 30. In some such embodiments, the interactive voice response system may prompt the caregiver to state certain words (e.g., "State 'clean' if the bed is clean, state 'dirty' if the bed is dirty, and then state the room number."). In still further embodiments, telephones or telephone handsets (wired or wireless) may have numbers which a caregiver is prompted to press by the interactive voice response system to indicate the bed clean/dirty status (e.g., "Please enter the room number." [caregiver responds by typing room number on telephone keypad] "If the bed is clean, press 1; if the bed, is dirty press 2" [caregiver responds by typing 1 or 2 on the telephone keypad]).

Referring again to FIG. 2, if a user selects icon 36, the system responds with a page that allows caregivers to be assigned to the various patient rooms, either as a primary caregiver or a secondary caregiver. If a user selects one of the rooms on screen 32, the system responds with a screen relating to certain information about the patient in the particular room selected. For example, if a caregiver selects room 413, such as by placing a cursor over the room and clicking or double-clicking a mouse, or by toggling to the room via tab or arrow keys on a computer keyboard, or by touching the screen on the desired room, then the system responds with a Patient screen 50, shown in FIG. 3, having information about hospital bed 10 in patient room 413 and other information.

Figure 3:
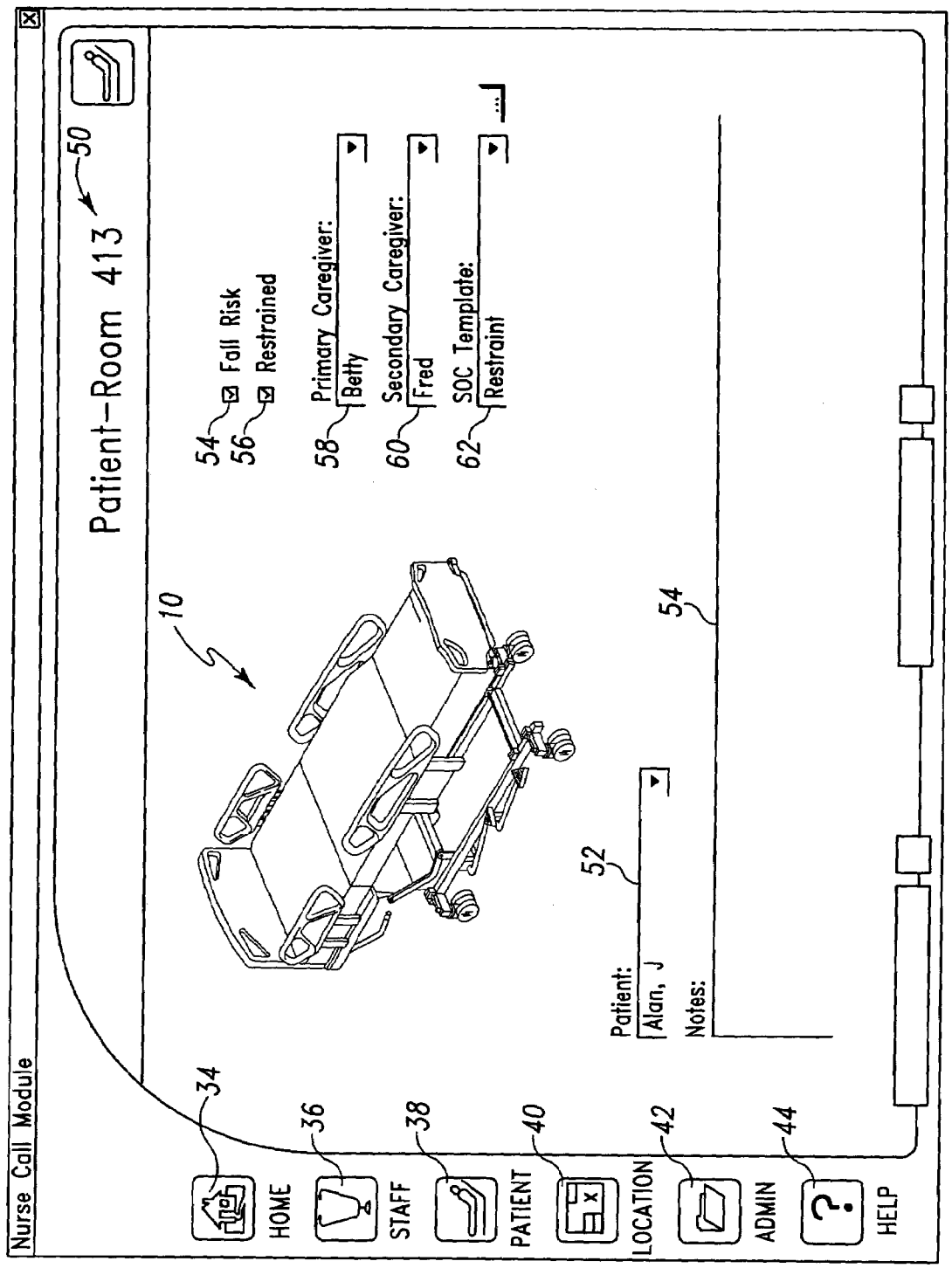
FIG. 3 is a screen shot of a Patient screen showing an image of a hospital bed in which no alarm conditions are occurring.

Screen 50 includes a name block 52 in which the patient's name is entered and a notes block in which additional notes about the patient or the patient's condition may be entered as shown in FIG. 3. Screen 50 also includes a Fall Risk check box 54 that is checked to indicate that the patient has a risk of falling and a Restrained check box 56 that is checked to indicate that the patient is restrained (i.e., that the patient is confined to bed 10 or that the patient is not to leave bed 10 without an alarm). Screen 50 further includes a Primary Caregiver text box 58, a Secondary Caregiver text box 60, and a Standard of Care (SOC) Template text box 62. In the illustrative example, box 58 indicates that Betty is the primary caregiver assigned to room 413 and box 60 indicates that Fred is the secondary caregiver assigned to room 413. Box 62 of screen 50 indicates that a Restraint Template has been configured for the patient in room 413. The system may be configured by caregivers to alarm when certain conditions of the bed and/or patient and/or other equipment included in network 12 are met. In FIG. 3, screen 50 includes an image of bed 10 when no alarm conditions are occurring on bed 10.

Figure 4:
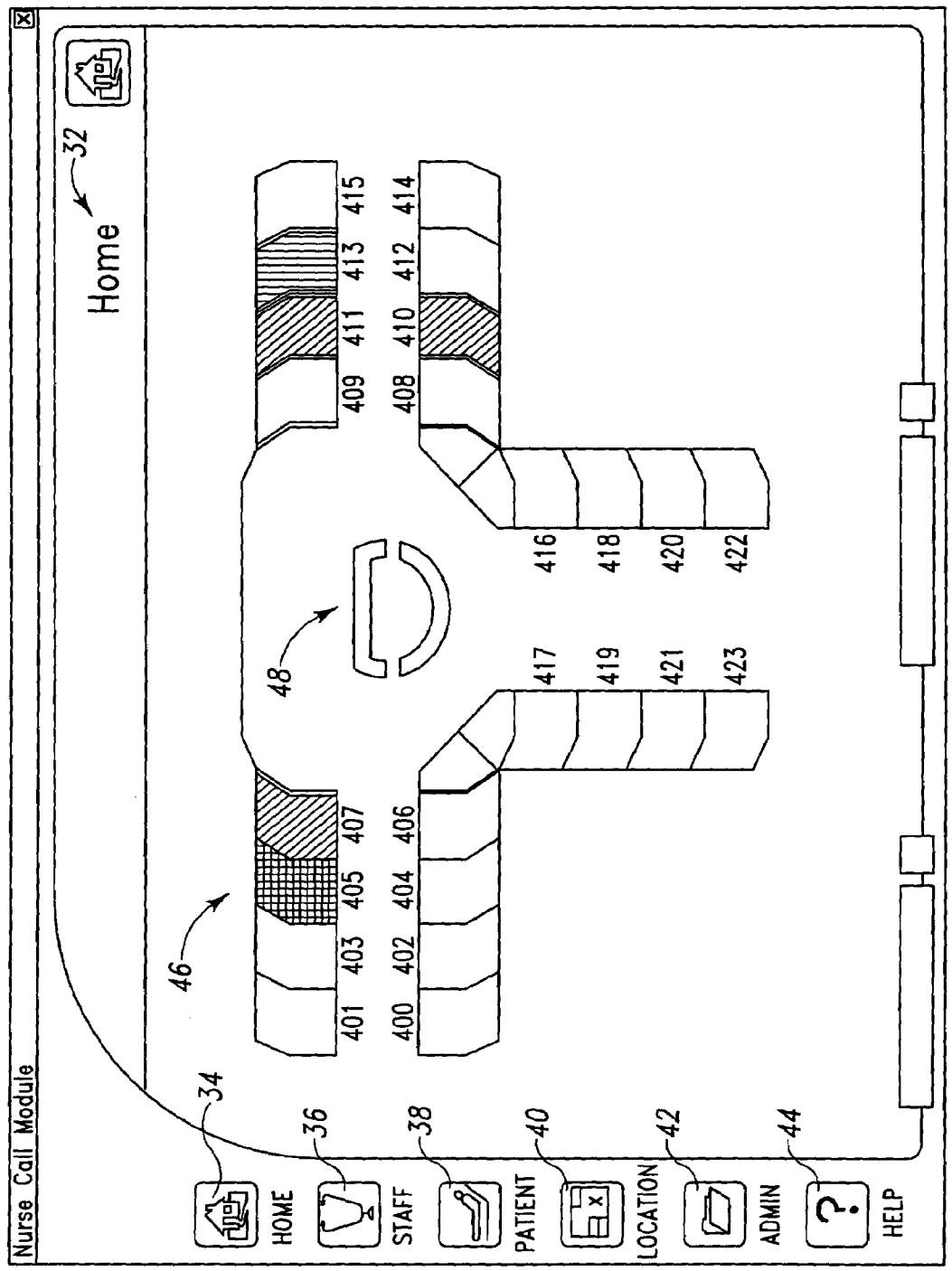
FIG. 4 is a screen shot of the Home screen showing room 413 being color coded in red to indicate that an alarm condition is occurring in room 413.
Figure 5:
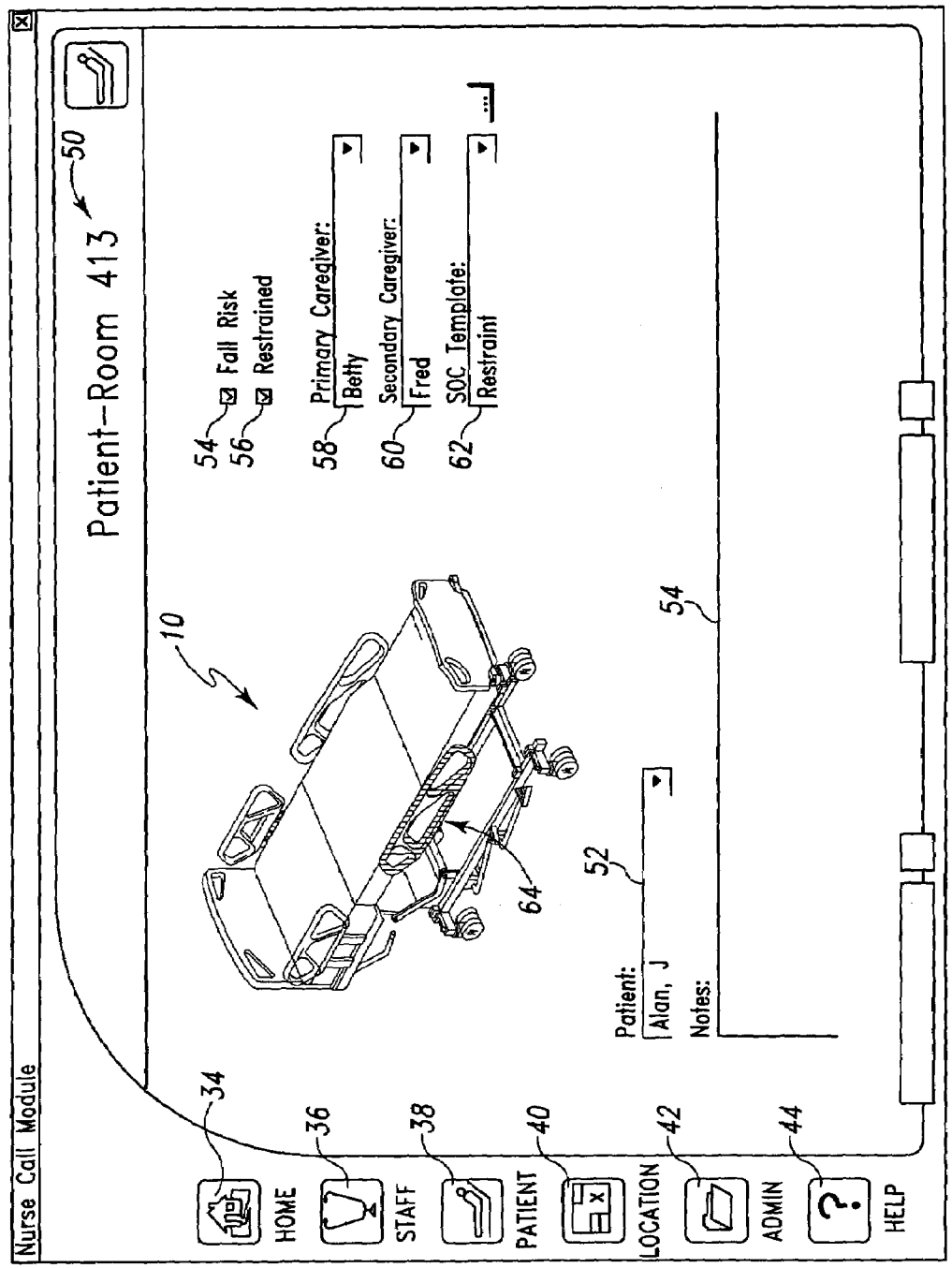
FIG. 5 is a screen shot of the Patient screen showing a siderail of the hospital bed being color coded in red and moved in the image to a lowered position to indicate the alarm condition occurring in room 413 is associated with the lowering of the siderail.

Referring now to FIG. 4, Home screen 32 has room 413 color coded in red to indicate that an alarm condition is occurring in room 413. If the user then selects room 413 on screen 32 of FIG. 4, the system responds with Patient screen 50 as shown in FIG. 5. However, due to the alarm condition in room 413, screen 50 now provides a visual indication of the condition that resulted in the alarm being generated by the system. In the illustrative example of FIG. 5, an image of a siderail 64 of bed 10 is shown in a lowered position and is color coded red to indicate that the alarm condition is that the siderail 64 of bed 10 has been lowered.

If a user selects location icon 40, the system responds with a list of caregivers that are carrying locating badges 20 and/or badges 26 and/or any other type of badges or handheld devices which communicates with the network 12 wirelessly to track the whereabouts of the caregivers. The user may then select a desired caregiver from the list and the system will respond with a location screen (not shown) which includes a layout (similar to layout 46) on which an icon is provided to indicate the location of the desired caregiver.

Figure 6:
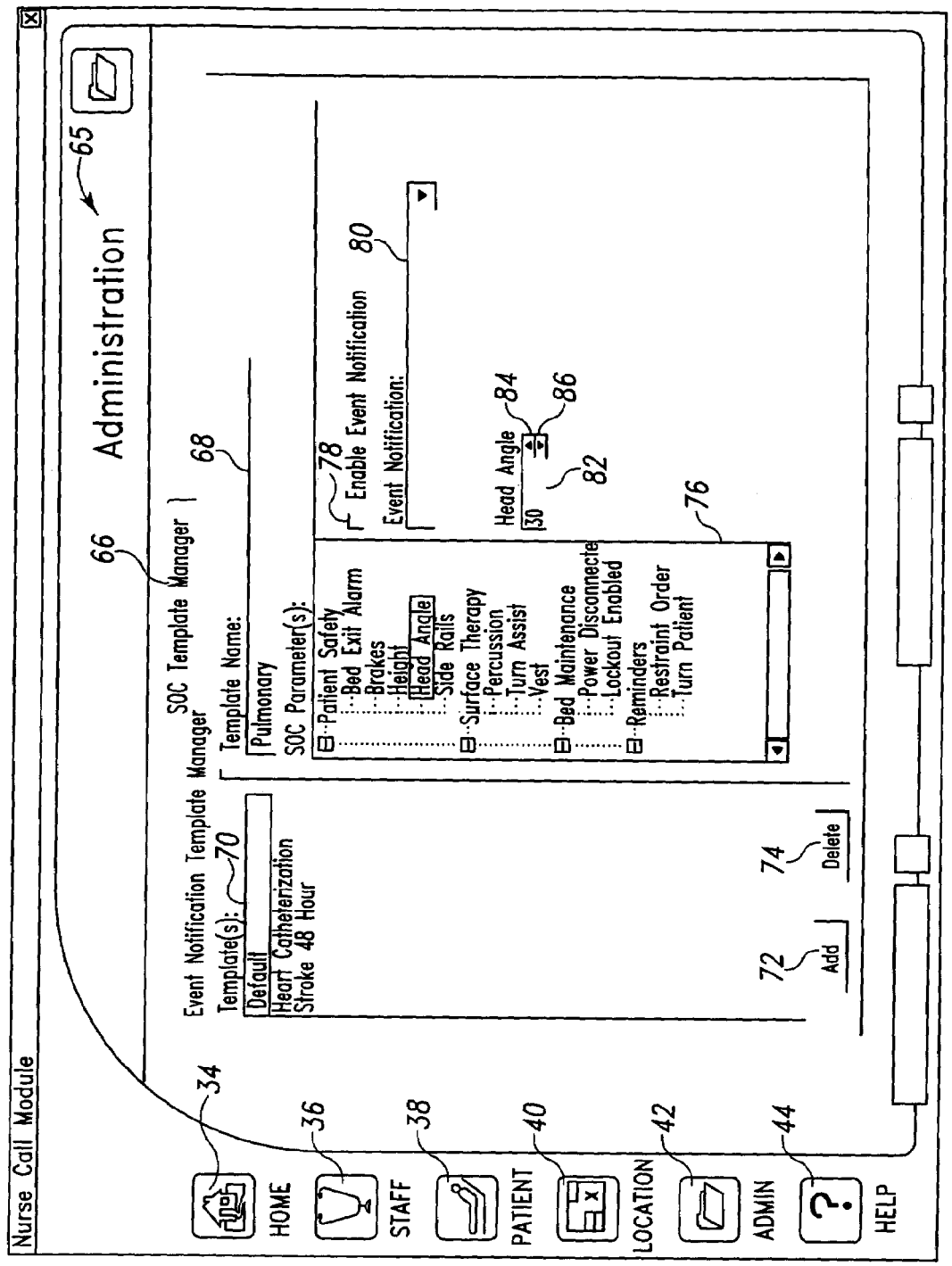
FIG. 6 is a screen shot of a Head Angle Administration screen.

If a user selects a patient room and then selects admin icon 42, the system responds with one of a number of Administration pages, such as those shown in FIGS. 6-9. In the illustrative example, when a room is selected and then icon 42 is selected, the system responds with a Head Angle Administration screen 65 as shown in FIG. 6. Screen 65 includes an SOC Template Manager Tab 66 which, when selected, shows a Template menu 70 which allows a user to select from a list of Template types and then to either add or delete the Template type for the associated patient room by selecting either an add icon 72 or a delete icon 74, respectively. Page 65 has a Template Name text box to indicate the name of the Template being shown. Page 65 also has an Event Notification Template Manager tab which may also be selected, if desired, to cause the system to respond with an Event Notification Template Manager screen (not shown).

Illustrative page 65 includes an SOC Parameter(s) table 76 on which are listed categories and subcategories of parameters that may be configured for generating an alarm or alert (e.g., an event notification) by the system. In the illustrative example, the categories are Patient Safety, Surface Therapy, Bed Maintenance, and Reminders. Under the Patient Safety category, the reminders are Bed Exit Alarm, Brakes, Height, Head Angle, and Side Rails. Under the Surface Therapy category, the subcategories are Percussion, Turn Assist, and Vest. Under the Bed Maintenance category, the subcategories are Power Disconnected and Lockout Enabled. Under the Reminders category, the subcategories are Restraint Order and Turn Patient.

In the illustrative example, the Head Angle subcategory under the Patient Safety category is selected. Screen 65 has an Enable Event Notification check box 78 that is selected (e.g., checked) if the user wants to have the system generate an alarm when a head angle (e.g., angle of articulation of a head section of bed 10) meets or exceeds a threshold value. Screen 65 also has an Event Notification text box 80 in which the message to be communicated (either via a text message on screen 27 or computer 30 or via a system-generated audible statement from badge 26, for example) to caregivers by the system. A drop down menu of such event notification messages is provided in the illustrative example and is accessed by selecting the arrow to the right of box 80. Because the Head Angle subcategory is selected, screen 65 also has a Head Angle box 82 in which the threshold angle is listed. Up arrow icon 84 and down arrow icon 86 are selectable by a user to adjust the threshold angle up or down, respectively, from the angle shown in box 82.

Figure 7:
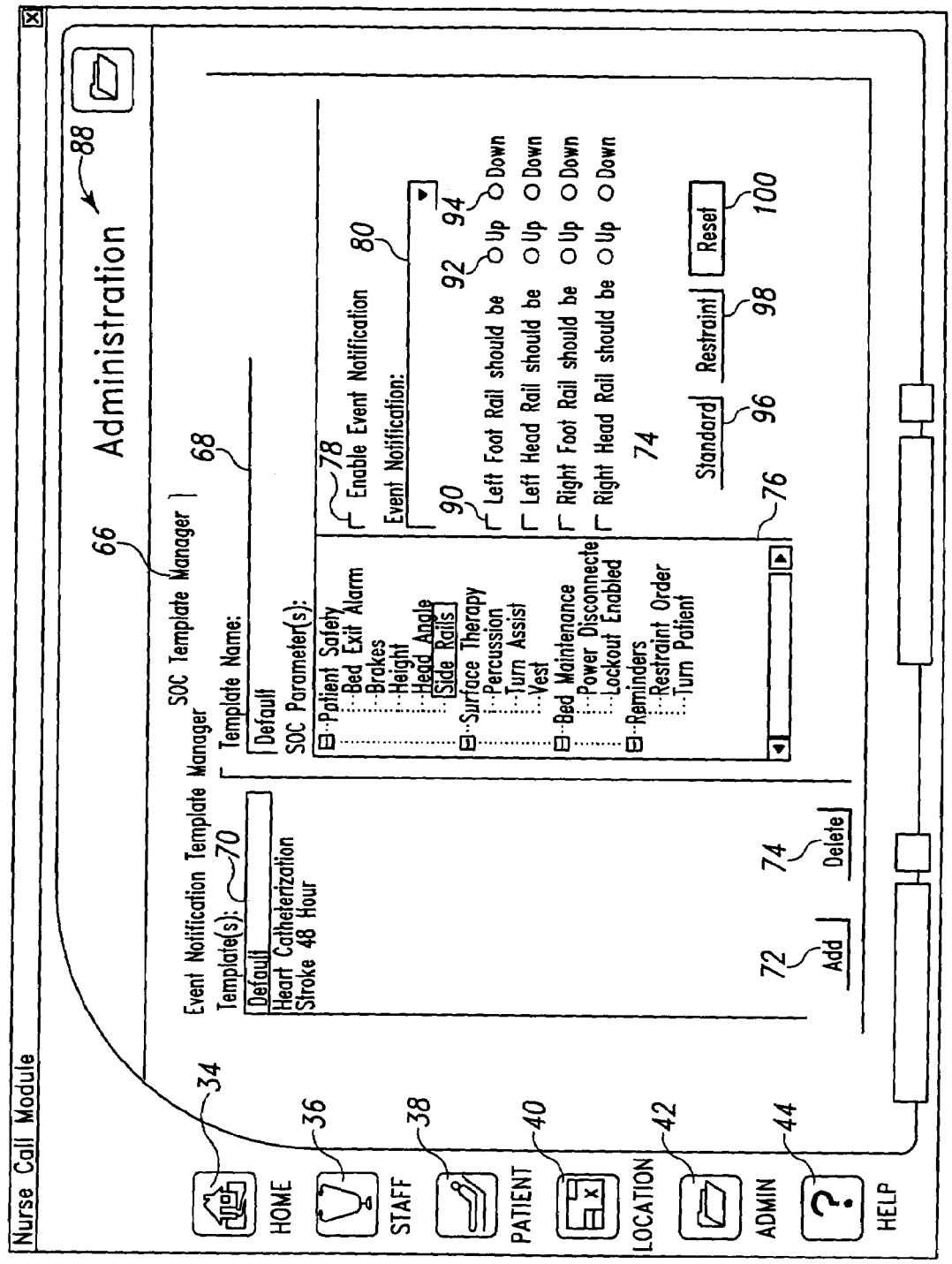
FIG. 7 is a screen shot of a Side Rails Administration screen.

The system responds with a Side Rails Administration screen 88, shown in FIG. 7, if subcategory Side Rails is selected on menu 76. Screen 88 includes some of the same menus, text boxes, check boxes, etc. that were described above in connection with screen 65 and therefore, the same references numerals are used to denote these without repeating the associated descriptions. Screen 88 includes a check box 90 adjacent the phrase "Left Foot Rail should be" and screen 88 also includes an Up radio button 92 adjacent the word "Up" and a Down radio button 94 adjacent the word "Down." If the system is to be configured such that a position of the left foot rail of bed 10 result in an event notification, then box 90 is selected or checked by a user and the desired one of buttons 92, 94 is also selected by the user. Buttons 92, 94 are mutually exclusive in that selection of one of buttons 92, 94 automatically results in the other of buttons 92, 94 being unselected. Similar provision is made on screen 88 for setting similar alarm conditions for the other three siderails of bed 10 but are not described herein for the sake of brevity.

Figure 8:
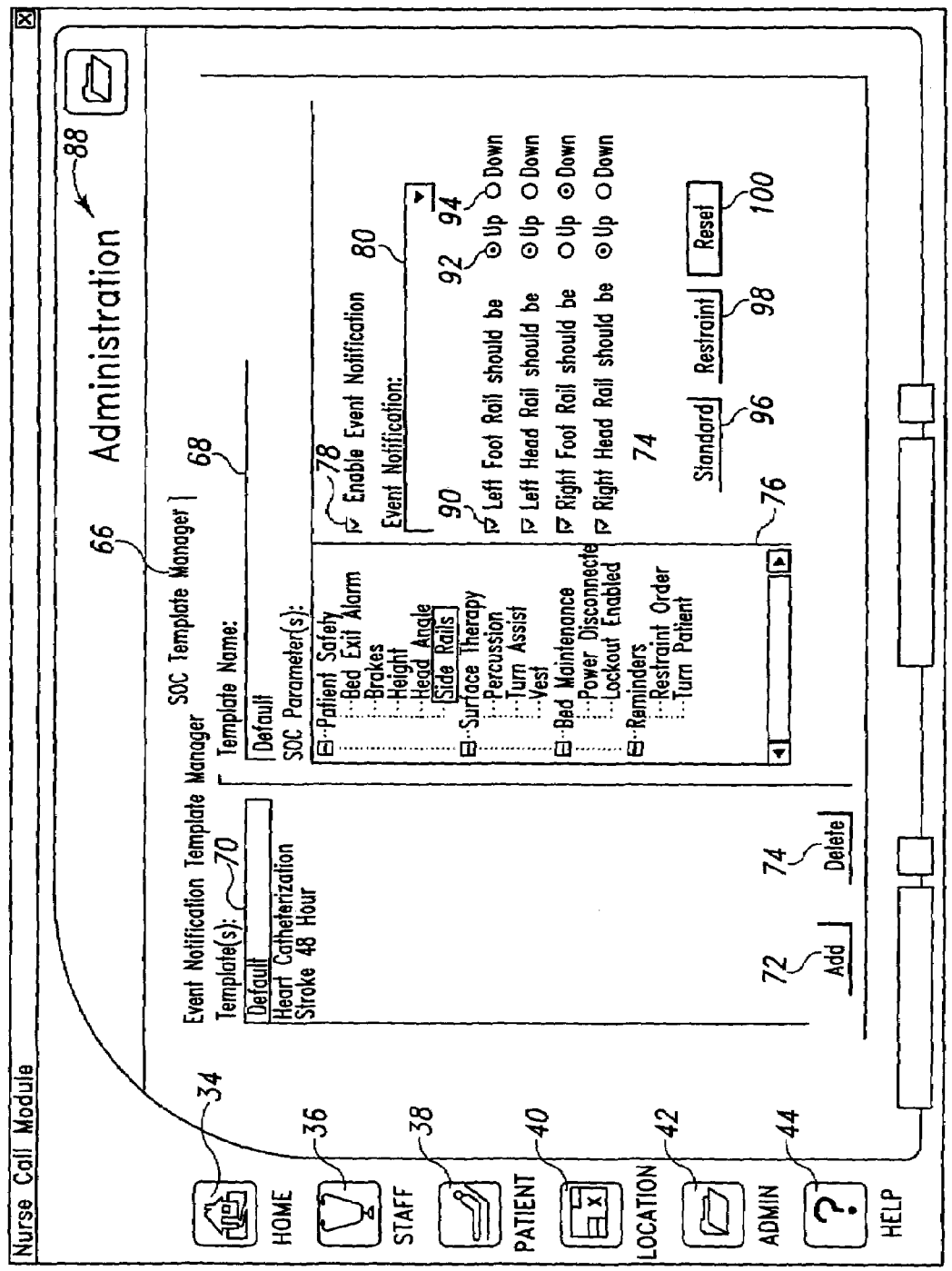
FIG. 8 is a screen shot of the Side Rails Administration screen showing various check boxes, text boxes, and radio buttons being selected to program the system with the alarm conditions to be associated with various siderail positions.

Illustrative screen 88 includes a Standard button 96, a Restraint button 98, and a Reset button 100. Selecting standard button 96 configures screen 88 automatically in one way corresponding to a standard set of alarm conditions and selecting restraint button configures screen 88 automatically in a different way corresponding to a restraint set of alarm conditions. Selecting Reset button 100 clears the selections that were made previously on screen 88. An illustrative example of how screen 88 may be configured by user is shown in FIG. 8 in which various check boxes, text boxes, and radio buttons have been selected to program the system with the alarm conditions to be associated with various siderail positions.

Figure 9:
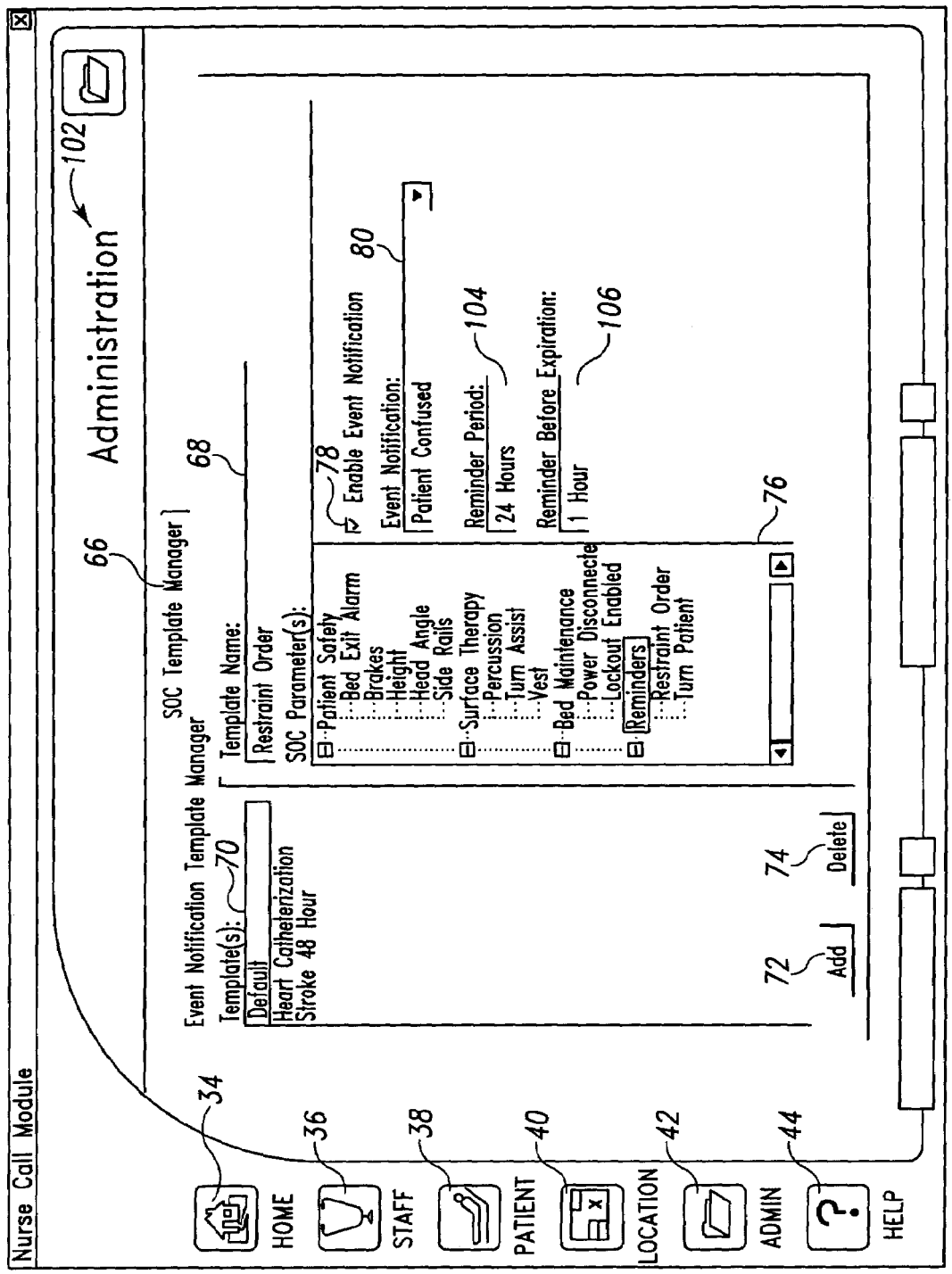
FIG. 9 is a screen shot of a Reminders Administration screen.

The system responds with a Reminders Administration screen 102, shown in FIG. 9, if subcategory Reminders is selected on menu 76. Screen 102 includes some of the same menus, text boxes, check boxes, etc. that were described above in connection with screen 65 and therefore, the same references numerals are used to denote these without repeating the associated descriptions. Screen 102 includes a Reminders Period box 104 in which a reminder period is entered to program the system how often one or more caregivers are to be reminded of a condition typed in box 80. Screen 102 also includes a Reminder Before Expiration box 106 in which is typed how long before the expiration of the reminder period the caregiver(s) is/are to be notified.

According to this disclosure, the system may be configurable such that when a locating-and-tracking portion of the system detects that a particular caregiver (or type of caregiver) has entered a particular room or otherwise is in close proximity to the bed, various functions of the bed will automatically be disabled and/or enabled and/or modified by the system. Thus, the bed may be configured automatically by the system for the caregiver without the caregiver having to press or otherwise manipulate any controls on the bed. Examples of functions that may be functionally modified in response to detection of caregiver presence include motor control access, confidential data access, Standard of Care (SOC) Notification, therapy controls, and nurse call system access.

It is contemplated by this disclosure that when a locating-and-tracking portion of the system detects that one or more caregivers, of the appropriate type, have entered a particular room, SOC Notification (e.g., alarm conditions configured on one of the Event Notification templates, which are sometimes referred to herein as Care Alert templates) is automatically disabled by computer 30 so that alerts occurring in a particular room are not transmitted to any caregivers when appropriate caregivers are already present in the room where the alert conditions are occurring. If the one or more designated caregivers leave the room without rectifying the alert condition, then an SOC Notification is initiated by computer 30 to one or more designated caregivers. The system, therefore, stores information about which caregivers are assigned to each patient and is able to discern the type of caregiver in the room, based on information received from the locating-and-tracking portion of the system, so that alert notifications are disabled only if the proper type of caregiver is present in the room. For example, it may not be desirable for the system to disable the alert notification is a food service caregiver enters the room instead of an assigned caregiver.

Figure 10:
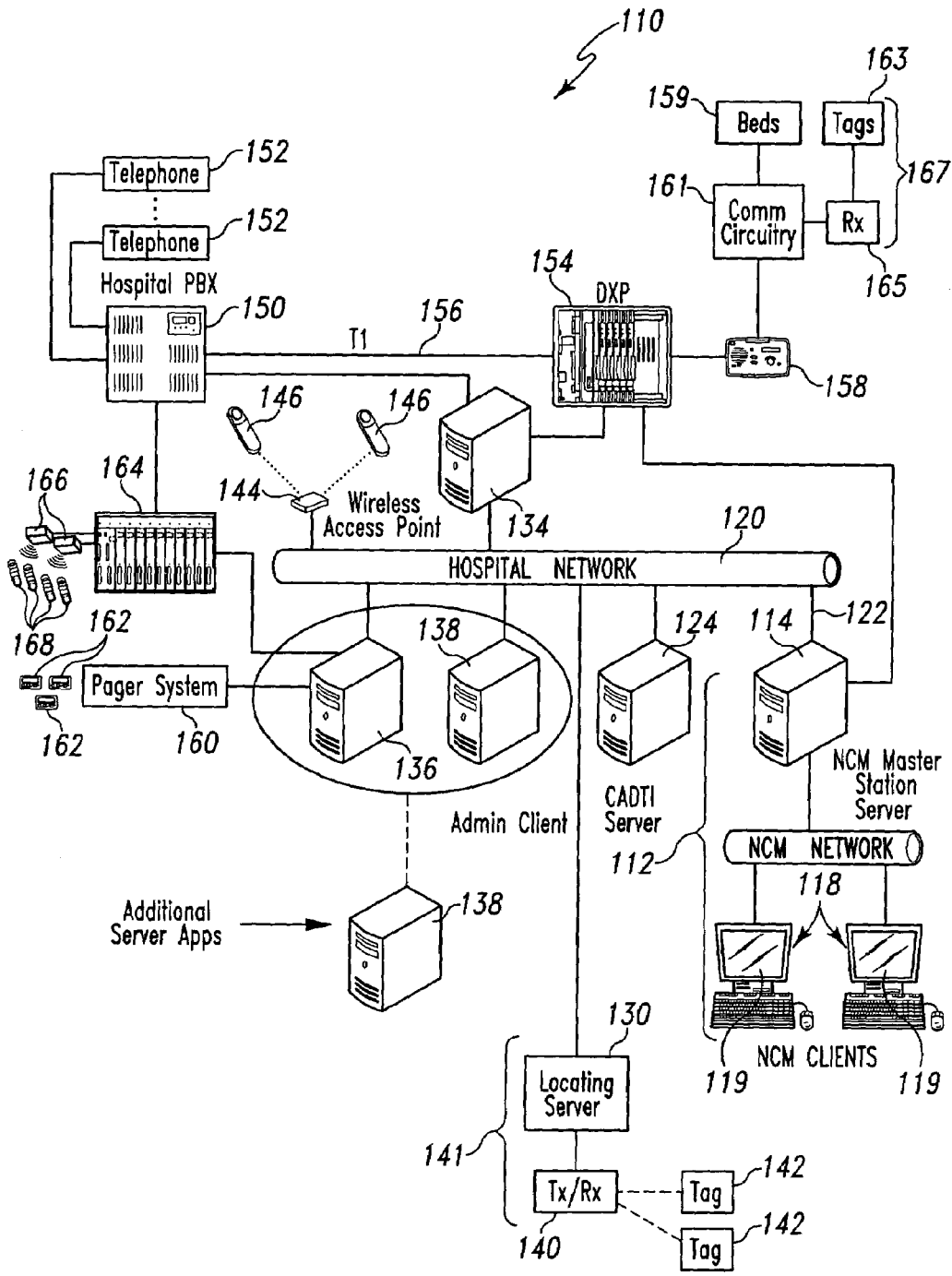
FIG. 10 is a block diagram showing various components of a network of devices in a healthcare facility, the network including a nurse call system including a nurse call server which executes nurse call application software and a number of nurse call client personal computers (PC's), and the network including a number of different types of communication devices.

Referring now to FIG. 10, a network 110 of a healthcare facility includes a nurse call system 112 that includes a nurse call module (NCM) server 114 and one or more NCM client personal computers (PC's) 118. Server 114 is coupled to hospital network infrastructure 120 via a wired or wireless communication link 122. The architecture of network 110 is generally at the discretion of information technology personnel of the healthcare facility and may include additional pieces of hardware (not shown) such as routers, backup power systems, and medical equipment, such as patient monitors, hospital beds, X-ray systems, and so on having networking capability. Devices such as servers, PC's, data storage devices, and any other pieces of hardware or equipment having processors, such as microprocessors, microcontrollers, field programmable gate arrays, programmable logic controllers, or other logic-based components for processing data, are considered to be computer devices according to this disclosure.

In the illustrative example, a CADTI server 124 of an Admission, Discharge, and Tracking (ADT) system (other components of the ADT system not shown) is also included in network 110. Network 110 further includes a locating server 130, a first communication system server 134, a second communication system server 136, and a plurality of additional servers 138. Illustratively, only two servers 138 are shown, but are intended to be representative of all of the other servers that are included in network 110. Each of the various servers 114, 124, 130, 134, 136, 138 has a processor (not shown) for executing associated application software. Of primary interest in the disclosure of the present embodiment is the nurse call software of server 114 and PC's 118. Associated with PC's 118 and server 114 are display screens 119.

It is contemplated by this disclosure that each of servers 114, 124, 130, 134, 136, 138 may transmit data to, and receive data from, each of the other servers 114, 124, 130, 134, 136, 138 so that the application software on each of servers 114, 124, 130, 134, 136, 138 has access to data on each of the other servers 114, 124, 130, 134, 136, 138. For example, locating server 130 is coupled to a plurality of transmitter and/or receiver units 140 which transmit and/or receive wireless signals to/from locating-and-tracking tags 142 that are mounted to pieces of equipment or carried by caregivers. One way that caregivers often carry tags 142 is by clipping or otherwise attaching the tags 142 to their clothing or by wearing the tags 142 on chains or cords around their necks. Tags 142 are sometimes referred to as "badges" by those in the art.

Locating server 130 executes software to track the whereabouts of equipment and caregivers throughout the associated healthcare facility based on wireless signals received by units 140 from tags 142. Thus, server 130, units 140, and tags 142 operate as a locating-and-tracking system 141 of network 110. In some embodiments, units 140 periodically transmit a wireless query within a limited area of the healthcare facility and any tags 142 within the limited area respond by transmitting unique identification (ID) data which is received by an associated unit 140 and forwarded to server 130. In other embodiments, tags 142 periodically transmit to any units 140 within range, their unique ID's without being queried. Server 130 associates the unique ID data from the tags 142 with ID data, such as a serial number, of the corresponding unit 140 which receives the wireless transmission from the tags 142. During execution of the nurse call software by server 114, if there is a need for data relating to the location of any equipment or persons being tracked by the locating-and-tracking software being executed by server 130, then server 114 sends a query to server 130 and server 130 responds with the requested information, if it is available. Alternatively, server 130 may periodically update server 114 with some or all of the data corresponding to the whereabouts of the equipment and caregivers being tracked and server 114 may store such data in the server's memory for possible future use.

Communication server 134 executes application software to send and receive communication data to/from one or more communication units 144 which, in turn, communicate wirelessly with portable wireless communication devices 146 carried by caregivers. In the illustrative example, server 134, units 144, and devices 146 are configured to support voice communications between users of devices 146 and the other portions of the network 110. Server 134 determines what other portion of network 110 users of devices 146 are intending to communicate with and transmits data representative of the voice communications to that portion of network 110. For example, the healthcare system's standard telephone system includes one or more private branch exchanges (PBX's) 150 and a plurality of telephones 152. Server 134 is coupled to the one or more PBX's 150 to communicate therewith. Network 110 also includes one or more Digital Phone Switch (DXP) units 154 that are coupled to the PBX's 150 via associated T1 lines 156. A plurality of Audio Stations 158 of nurse call system 112 are located throughout the healthcare facility, typically in patient rooms, and are also coupled to the DXP units 154. Thus, users of portable wireless communication devices 146 can speak to and hear from users of telephones 152 and users of audio stations 158. In some embodiments, audio stations 158 are substantially similar to those described in U.S. Pat. Nos. 5,561,412 and 5,699,038 which are hereby expressly incorporated by reference herein.

In one embodiment, devices 146 and units 144 are the type marketed by Vocera Communications, Inc. of Cupertino, Calif. and sold under the Vocera™ brand name. Such Vocera™ devices 146 (referred to sometimes as badges) may be worn by users in the same manner as tags 142 described above. The Vocera™ badges 146 and Vocera™ units 144 communicate over an 802.11b LAN infrastructure and also with the PBX's 150 via server 134 which executes associated Vocera™ server software. Devices 146 and units 144 which communicate according to wireless communications protocols other than 802.11b, such as the Bluetooth protocol, for example, are contemplated by this disclosure. In some embodiments, server 134 comprises multiple servers, one server operating software provided by Vocera Communications, Inc. (the "Vocera server") and another server operating software provided Emergin, Inc. of Boca Raton, Fla. (the "Emergin server"). The Emergin server converts messages received from the Vocera server from the 802.11b protocol into the appropriate protocol for the hardware for which the message is destined and converts messages destined for the Vocera server into the 802.11b protocol from the protocol in which it was received by the Emergin server.

Illustrative network 110 also includes a pager system 160 which is coupled to server 136 and which includes a plurality of pagers 162 carried by some of the caregivers. Also coupled to server 136 and to PBX's 150 are one or more master control units 164 of a dedicated wireless telephone system of the health care facility. The dedicated wireless telephone system further includes a number of base stations 166 and number of wireless telephone handsets 168. As was the case with Vocera™ badges 146, handsets 168 are considered to be portable wireless communication devices according to this disclosure. While it is within the scope of this disclosure for network 110 to have any type of dedicated wireless telephone system, or none at all, in some embodiments, units 164, base stations 166, and handsets 168 are of the type marketed by Spectralink Corporation of Boulder, Colo. and/or ASCOM Ltd. of Berne, Switzerland. The Spectralink™ base stations 166 and handsets 168 communicate wirelessly via a scheme of frequency hopping spread spectrum over four TDMA channels in the 902-928 MHz radio frequency range. The Spectralink™ master control units 164 communicate with the PBX's 150 of system 110 either via a digital and/or an analog interface.

Each audio station 158 is coupled to one or more beds 159 via associated communications circuitry 161 as shown diagrammatically in FIG. 10 (only one audio station 158 is illustrated to represent a plurality of such stations 158). In some embodiments, caregivers wear or carry tags 163 which transmit signals received by receivers 165 which are also coupled to circuitry 161 as also shown diagrammatically in FIG. 10. Thus, tags 163, receivers 165, circuitry 161, and audio stations 161, when present, operate as a locating-and-tracking system 167 of network 110 that is separate from system 141. In some embodiments, tags 142 may communicate via radio frequency (RF) signals, whereas tags 163 may communicate via infrared (IR) signals. Because IR signals require line of sight between tags 163 and receivers 165, receivers 165 are less apt to receive a signal from tags 163 unless the caregiver is actually present in the room in which the associated receiver is located, whereas RF tags 142 have a tendency to transmit signals through walls, floors, and ceilings such that signals form tags 142 may be picked up by multiple units 140 located in different rooms or hallways in a healthcare facility. In some embodiments, tags 142 and/or tags 163 may use other types of wireless transmission (e.g., ultraviolet or ultrasonic) and in some embodiments, tags 142 and/or tags 163 may use multiple types of wireless transmission (e.g. IR and RF). Locating-and-tracking information from system 167 is used by server 114 to determine the whereabouts of caregivers in a manner substantially similar to that described above in connection with system 141 and therefore, is not repeated herein for the sake of brevity.

Figure 11:
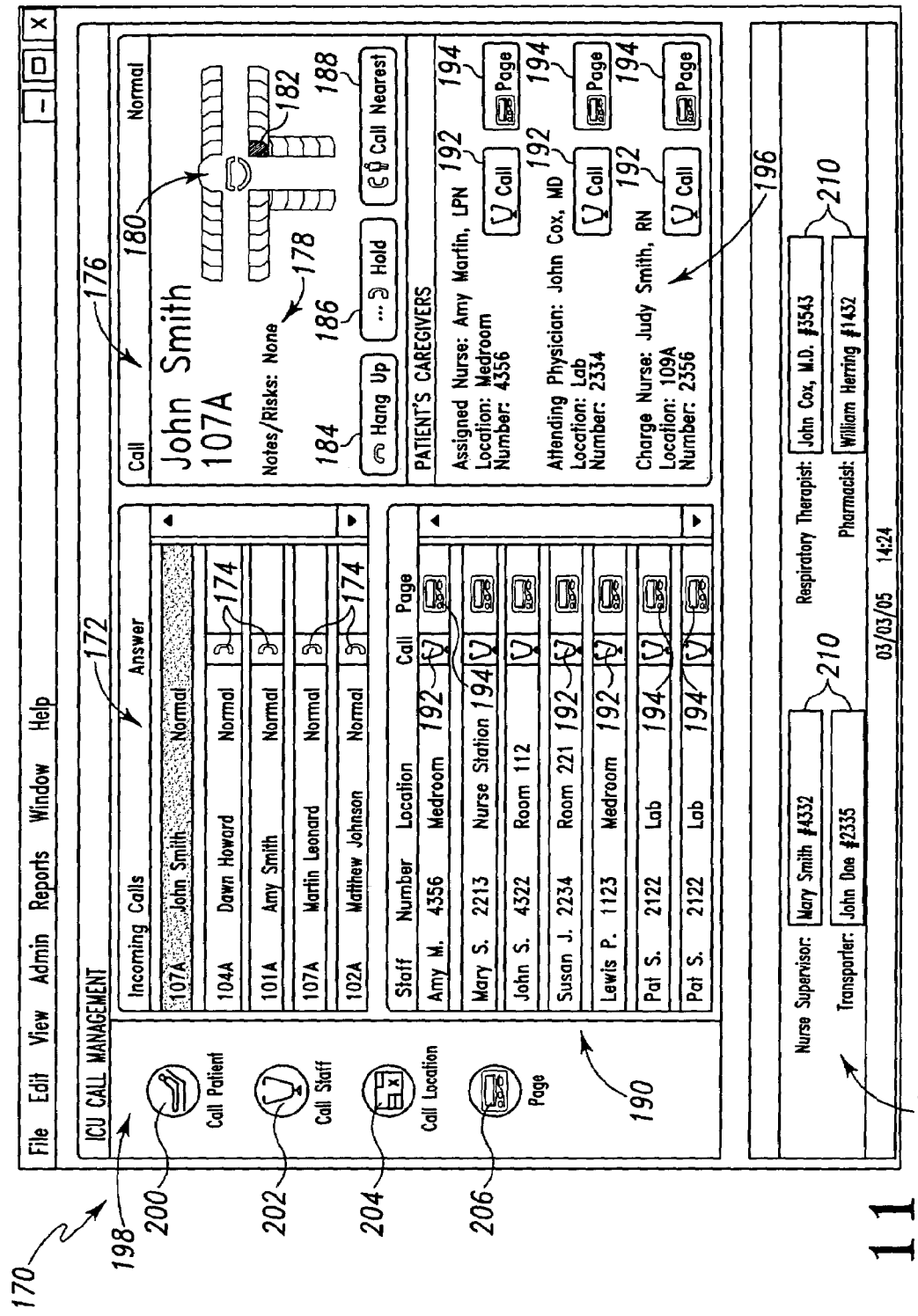
FIG. 11 is a screen shot of a Call Management screen showing an Incoming Calls Window that lists the nurse calls received by a Master Nurse Call station, a Staff Window beneath the Incoming Calls window, a set of Call/Page buttons to the left of the Incoming Calls and Staff Windows, a Call Window to the right of the Incoming Calls Window, and a Patient's Caregivers Window beneath the Call Window.

Referring now to FIG. 11, a Call Management screen 170 of system 112 has an Incoming Calls Window 172 that lists the nurse calls coming in to a Master Nurse Call station at which one of PC's 118 is located. In one embodiment, up to 5 incoming calls may be shown in window 172. The application software of system 112 may be configured to permit more or less than 5 incoming calls to be displayed in window 112. Window 172 shows the room number, patient's name, and alarm condition of the monitored equipment for each patient placing a nurse call. On the first line of the illustrative example of window 172, John Smith is the name of the patient, room 107A is the room in which John Smith is located, and the word "Normal" indicates that one or more normal alarm conditions are occurring in connection with the equipment that is being monitored by the system and that is associated with John Smith.

Screen 170 has the highest priority of all of the screens displayed at the Master Nurse Call Station. If the PC 118 at the Master Nurse Call Station has remained idle for a predetermined amount of time, then system 112 will operate to automatically display screen 170 on the monitor or display of PC 118. The predetermined amount of time at which system 112 defaults back to screen 170 can be set by the user by accessing a menu which appears after an Admin icon 171 is selected and then after System Control and System Timeout options are selected within the associated drop down menus. In one embodiment, the menu that allows the system timeout to be selected by the user includes options for selection of either 30 seconds, 1 minute, 3 minutes, or never.

An answer button 174 is shown on each line in window 172 for which a call is being placed. The calls to system 112 are displayed in window 172 in order of priority, which is normally in the order (i.e., date and time) received by system 112. However, depending upon whether system 112 detects an alarm condition, then calls placed from rooms in which an alarm condition are detected are prioritized ahead of calls from rooms where no alarm condition exists. Alarms may be designated as having either high, normal, or low priority. Thus, high priority alarms are listed in window 172 ahead of those having normal or low priority. If a caregiver at the Master Nurse Call Station wants to answer the call from a particular patient, the caregiver selects the answer button 174 next to the patient's name, such as by moving a computer mouse to place a cursor over the button icon and then clicking a button on the mouse. Other methods of selecting buttons 174 are within in the scope of this disclosure and include using the tab or arrow keys on a computer keyboard to highlight the desired icon 174 and then pressing the enter key of the keyboard or by touching the screen, such as with a finger, stylus, or light pen, on the area of the screen on which the desired button 174 is displayed.

When an answer button 174 is selected, system 112 and the associated equipment of network 110 respond by establishing a voice communications link between the Master Nurse Call Station and either the Audio Station 158 associated with the patient or with a microphone and speaker system provided on the patient's bed. When one call is answered, the other calls appearing in window 172 are grayed out. When the caregiver selects one of buttons 174 to answer a call from a particular patient, system 112 operates to display information about the particular patient in a Call Window 176 of screen 170. Window 176 lists the patient's name and room numbers in a larger font than other text on screen 170 and includes a Notes/Risks text area 178 in which any comments entered into system 112 about the patient are displayed. A layout image or floor plan 180 of the wing of the hospital in which the associated patient is located is also shown in window 176. The room in which the particular patient is located is highlighted on image 180 with color coding. In the illustrative example, a room 182 is highlighted green to indicate the "normal" alarm status of the monitored equipment in room 107A in which John Smith (the patient's whose call has been answered) is located.

Window 176 also includes a Hang Up button 184, a Hold button 186, and a Call Nearest button 188. Button 184 is selected by the caregiver at the Master Nurse Call Station when the caregiver wants to end the call with the patient. Button 186 is selected by the caregiver at the Master Nurse Call Station when the caregiver wants to place the current call on hold, possibly so that the caregiver can answer another call. If a patient is placed on hold, then a corresponding icon image (i.e., a set of ellipses and a phone, in the illustrative example) is placed in the associated row in the Incoming Calls window 172 of screen 170 so that the caregiver knows which patients have been placed on hold. Button 188 is selected if the caregiver at the Master Nurse Call station wants to call the nearest staff member, possibly to direct that caregiver to the room of the patient making the call. If the patient making the call has not been placed on hold, then network 110 operates to establish a 3-way telecommunications conference when the nearest caregiver who is contacted as a result of button 188 being selected answers the call.

Screen 170 further includes a Staff Window 190 beneath the Incoming Calls window 172 as shown in FIG. 11. Window 190 lists the names of medical staff, the numbers of the medical staff, and the location of the medical staff for those persons on the medical staff who are being tracked by the locating-and-tracking system 141 and/or system 167. Window 190 also includes a Call button 192 and a Page button 194 which are selected to direct system 112 to initiate a call or page, respectively, to the associated caregiver. Optionally, the last time that persons on the staff were located may appear in window 190 for those caregivers having tags 142 of system 141, or whose locations are otherwise tracked, such as, for example, via badges 146 having locating-and-tracking capability or via system 167.

If a call to a caregiver is initiated by selection of one of buttons 192, then the appropriate commands are sent by server 114 to the other portions of network 110 to make the call. For example, if the caregiver is carrying a badge 146, then server 114 communicates with server 134 in connection with making the call, but if the caregiver is carrying a handset 168, then server 114 communicates with server 136 in connection with making the call. If the caregiver is not carrying one of badges 146 or one of handsets 168, then call buttons 192 will be usable on screen 170 only if system 112 is notified of the caregivers whereabouts by system 141 in which case selection of the associated button 192 results in a call to the audio station 158 where the caregiver is located. Buttons 192 are grayed out for those caregivers who are not located by system 141 or system 167 (as the case may be), who do not have one badges 146, who do not have one of handsets 168, and who do not have any other type of device which allow wireless voice communications with the caregiver as part of network 110. If a page to a caregiver is initiated by selection of button 194, then server 114 communicates with server 136 resulting in a page being sent through system 160 to the selected caregiver's pager 162. For those caregivers do not have one of pagers 162, the associated button 194 is either grayed out on, or absent from, window 190.

Screen 170 also has a Patient's Caregivers Window 196 which appears beneath window 176 when the caregiver at the Master Nurse Call Station answers a call from a patient by selecting the associated answer button 174. Window 196 shows the names of any caregivers that are assigned to the particular patient, the number of the caregiver, and the caregiver's location if the caregiver is being tracked by system 141 or system 167. In the illustrative example, window 196 shows that Amy Martin, LPN is the nurse assigned to the patient John Smith whose call has been answered; John Cox, M.D. is John Smith's attending physician; and Judy Smith, RN is the charge nurse assigned to John Smith. Window 196 also shows that Nurse Martin is in the Medroom, Dr. Cox is in the Lab, and Nurse Smith is in room 109A. If button 188 is selected on window 176, then system 112 responds by calling the audio station 158 in room 109A because that is where the closest caregiver assigned to the calling patient is located. Window 196 also includes call buttons 192 and page buttons 194 which operate the same as these same-numbered icons operate in connection with window 190 as described above.

Screen 170 further includes a set of Call/Page buttons to the left of windows 172, 190. The set of Call/Page buttons include a Call Patient button 200, a Call Staff Button 202, a Call Location button 204, and a Page button 206. Button 200 may be selected if the caregiver at the Master Nurse Call Station wishes to place a call to a particular patient. If button 200 is selected, system 112 responds with a window that either allows selection of the patient to be called from a list of patients or that allows the appropriate patient information, such as the patient's location (such as room number) or names, to be entered into an appropriate field. Button 202 may be selected if the caregiver at the Master Nurse Call Station wishes to place a call to a particular caregiver. If button 202 is selected, system 112 responds with a window either that allows selection of the caregiver to be called from a list of caregivers or that allows the appropriate caregiver information, such as the number of the caregiver's badge 146 or handset 168, to be entered into an appropriate field.

Button 204 may be selected to place a call to a particular audio station 158 at a particular location in the healthcare facility. Such a call may be placed, for example, to reach either a patient or a caregiver that is in the same location with the particular audio station 158. If button 204 is selected, system 112 responds with a window either that allows selection of the particular location to which the call is to be made from a list of locations or that allows the appropriate location information, such as a room number or room name, to be entered into an appropriate field. Button 206 may be selected to initiate a page to a particular caregiver. If button 206 is selected, system 112 responds with a window either that allows selection of a particular caregiver to be paged from a list of caregivers who are carrying pagers or that allows a pager number to be entered into an appropriate field.

Screen 170 also has a Unit Information Window 208 which includes general information about the unit or units associated with the Master Nurse Call Station. In the illustrative example, a number of name boxes 210 in which the names of various persons on the medical staff appear. The roles of the persons on the medical staff which appear in boxes 210 of window 208 are at the discretion of the user who configures screen 170 and generally will vary depending upon the type of unit associated with the Master Nurse Call Station. In the illustrative example, boxes 210 include the names of the Nurse Supervisor, the Transporter, the Respiratory Therapist, and the Pharmacist of the associated unit.

According to the present disclosure, users of system 112 with administration rights may create Care Alert templates to setup customized screens on which other users select the types of events or conditions to which caregivers are to be alerted. Such users may also modify the default alarm conditions for existing templates. For example, selection by such users of an Edit icon on a main menu results in display of a drop down menu including a Template icon. Selection of the Template icon then results in another drop down menu which lists all of the available Care Alert templates, by name, along with a New icon. Selection of one of the available Care Alert templates results in the associated Template being displayed with all of its default settings. The user having administration rights is then able to select, deselect, enter numerical alarm thresholds, and otherwise modify the alarm conditions associated with the selected existing Care Alert template. Selection of the New icon on the menu results in a menu of Parameter Titles that may be selected. Selection of an appropriate Parameter Title then allows the user to select particular parameters, options, and control elements as outlined in the following table:

| Parameter Title | Parameters | Options | Control Element |
|---|---|---|---|
| Bed Status | Bed Status Alert Priority | High<br>Medium<br>Low | Radio buttons |
| | Patient Safety | Bed should be in lowest position<br>Bed brakes should be set<br>Patient should remain in bed | Check boxes |
| | Side Rails | Left Head Rail<br>Up    Down<br>Left Foot Rail<br>Up    Down<br>Right Head Rail<br>Up    Down<br>Right Foot Rail<br>Up    Down | Check boxes and Radio buttons |
| | Motor Lockout | All controls should be locked out (except emergency)<br>Hi-Lo controls should be locked out<br>Head position controls should be locked out<br>Knee position controls should be locked out | Check boxes |
| Surface Therapy | Surface Therapy Alert Priority | High<br>Medium<br>Low | Radio buttons |
| | Modes | Prevention<br>Pressure Relief<br>Opti-Rest<br>Comfort | Check boxes |
| | Percussion | Therapy 1<br>Therapy 2<br>Therapy 3 | Radio buttons |
| | Turn Assist | Patient should be turned every ____ ____ | Drop down lists and Spin buttons |
| | Vest | Therapy 1<br>Therapy 2<br>Therapy 3 | Radio buttons |
| Bed Maintenance | Bed Maintenance Alert Priority | High<br>Medium<br>Low | Radio buttons |
| | Power Disconnect | Bed is disconnected from the wall<br>Bed failure occurs<br>Bed is moved to another location | Check boxes |
| Patient Care | Patient Care Alert Priority | High<br>Medium<br>Low | Radio buttons |
| | Patient Positioning | Head angle between ____ and ____ degrees<br>Always No more than____ ____ at a time.<br>Trendelenburg<br>Reverse Trendelenburg | Drop down lists, Spin buttons, and Radio buttons |

-continued

| Parameter Title | Parameters | Options | Control Element |
|---|---|---|---|
| | Up in Chair Orders | Flat<br>Patient should be up in chair every ____ ____<br>For ____ ____<br>Between ____ ____ and ____ ____ | Drop down lists and Spin buttons |
| Reminders | Reminders Alert Priority | High<br>Medium<br>Low | Radio buttons |
| | Restraints | Notify when patient movement is detected<br>Patient is restrained<br>Reminder to renew restraint orders ____ ____<br>Reminder to check on patient every ____ ____ | Check boxes, Drop down lists, and Spin buttons |

The parameters listed in the above table are related to the status of hospital beds and mattresses. It is within the scope of this disclosure, however, for parameters of other patient care equipment to be monitored by system 112. Thus, the teachings of this disclosure regarding creating and using Care Alert templates is applicable to all types of equipment used in connection with patient care, not just hospital beds and mattresses. Such other types of patient care equipment may include IV pumps, ventilators, and patient monitors of all types including EKG's, EEG's, and pulse oximeters.

System 112 also includes one or more default templates which are preprogrammed and which are automatically assigned to all patients who are admitted to the hospital. In some embodiments, the default templates names are passed to the ADT system and an admissions officer of a healthcare facility may, if desired, assign a Care Alert template to a patient using the ADT system during the admissions process and the assigned Care Alert template is communicated from the ADT system to system 112. A user of system 112 may verify or change the Care Alert template selected by the admissions officer using system 112. In some embodiments, if the admissions officer does not assign a Care Alert template to a patient, then a pre-selected default template may be assigned by system 112 to the patient automatically for subsequent verification or modification by users of system 112.

Figure 12:
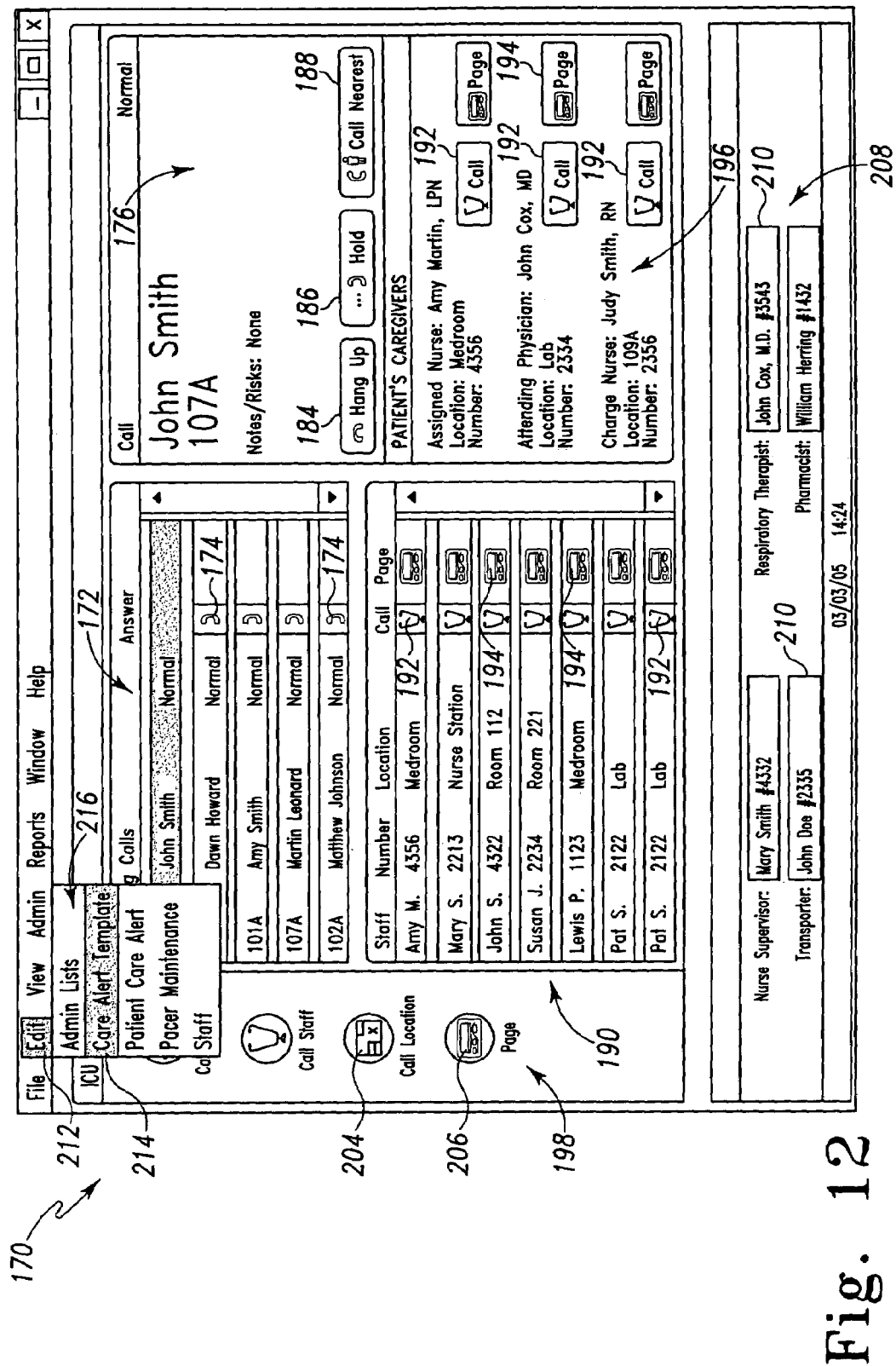
FIG. 12 is a screen shot, similar to FIG. 11, showing an Edit drop down menu on which a Care Alert Template option is highlighted.
Figure 13:
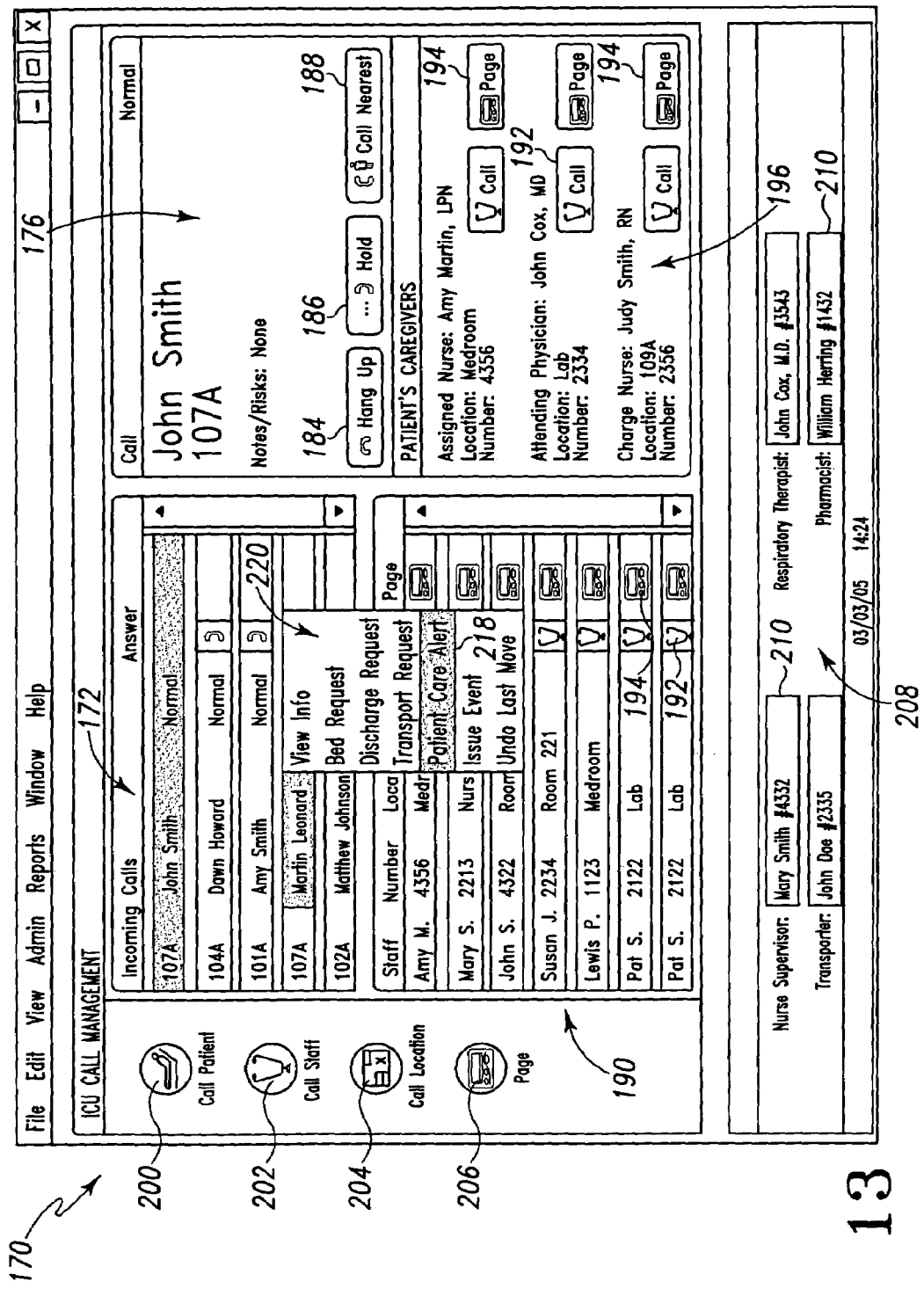
FIG. 13 is a screen shot, similar to FIG. 11, showing a patient-specific drop down on which a Patient Care Alert option is highlighted.

The default templates and custom-created templates are accessible by users by either selecting an Edit button 212 and then a Care Alert Template button 214 which appears in an associated drop down menu 216, shown in FIG. 12, or by right clicking on a patient's name and then selecting a Patient Care Alert button 218 in an associated drop down menu 220, shown in FIG. 13. A particular patient's Care Alert template can also be accessed in manner similar to that illustrated in FIG. 13 by performing similar steps in connection with a Whiteboard screen shown in FIG. 15.

Figure 14:
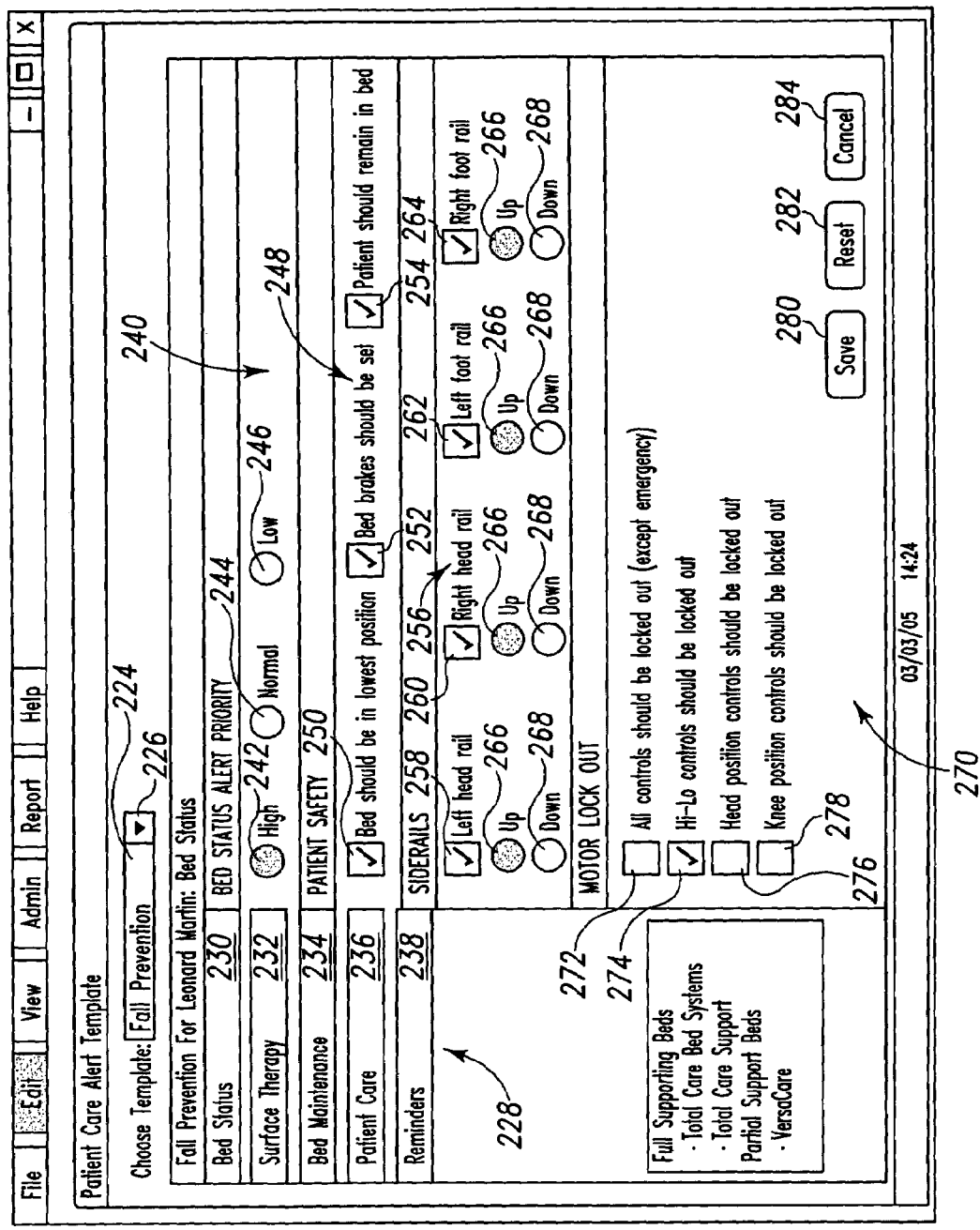
FIG. 14 is a screen shot of a Patient Care Alert Template showing various check boxes and radio buttons selected to program the system with the alarm conditions to be associated with bed status.

FIG. 14 is a screen shot of an example of a Patient Care Alert Template screen 222 having configurable alarm conditions associated with the "bed status" portion of the above table. Screen 222 has a Chose Template box 224 with an arrow icon 226 which, when selected, causes a drop down menu (not shown) to appear with options for pre-selected configurations of screen 222. In the present example, a Fall Prevention template configuration option has been selected in box 224 resulting in various check boxes and radio buttons being selected in screen 222 to configure system 112 with the alarm conditions to be associated with bed status for fall prevention. Screen 222 also has a menu 228 of other Care Alert Template screens which the user can access if desired. In the illustrative example, menu 228 includes a Bed Status button 230, a Surface Therapy button 232, a Bed Maintenance button 234, a Patient Care button 236, and a Reminders button 238. Button 230 is highlighted in FIG. 14 because the template associate with bed status is being displayed. Selection of any of the other buttons 232, 234, 236, 238 causes system 112 to respond with the associated template being shown on the monitor of the associated PC 118. Buttons 230, 232, 234, 236, 238 correspond to the parameter titles listed in the above table.

Screen 222 includes a Bed Status Alert Priority window 240 which has therein a High radio button 242, a Normal (referred to sometimes in Appendix 2 as "Medium") radio button 244, and a Low radio button 246. One of buttons 242, 244, 246 is selected to configure the priority level to be assigned to the alarms associated with screen 222. In the illustrative example in which the Fall Prevention template configuration is selected, button 242 has been selected. If button 242, which corresponds to a High Priority Level, is selected, then when an alarm condition occurs, system 112 responds by initiating a wireless communication to all medical staff who are associated with the unit and who have wireless communication devices; causing an audible alert tone at the Master Nurse Call Station; causing red, blinking indicators on the monitor at the Master Nurse Call Station; and causing the dome lights outside the patient's room to flash. If button 244, which corresponds to a Normal or Medium Priority Level, is selected, then when an alarm condition occurs, system 112 responds by initiating a wireless communication to the particular patient's assigned caregiver; causing an audible alert tone at the Master Nurse Call Station; causing yellow, blinking indicators on the monitor at the Master Nurse Call Station; and causing the dome lights outside the patient's room to flash. If button 246, which corresponds to a Low Priority Level, is selected, then when an alarm condition occurs, system 112 responds by initiating a wireless communication to the particular patient's assigned caregiver; causing an audible alert tone at the Master Nurse Call Station; causing a yellow, non-blinking indicator on the monitor at the Master Nurse Call Station; and causing the dome lights outside the patient's room to flash.

Screen 222 also has a Patient Safety window 248 which includes therein a "Bed should be in lowest position" check box 250, a "Bed brakes should be set" check box 252, and a "Patient should remain in bed" check box 254. In the illustrative example in which the Fall Prevention template configuration is selected, all of boxes 250, 252, 254 are checked. Screen 222 further includes a Siderails window 256 which includes therein a "Left head rail" check box 258, a "Right head rail" check box 260, a "Left foot rail" check box 262, and a "Right foot rail" check box 264. Beneath each check box 258, 260, 262, 264 is an associated Up radio button 266 and an associated Down radio button 268. In the illustrative example in which the Fall Prevention template configuration is selected, check boxes 258, 260, 262, 264 are each checked and Up radio buttons 266 are each selected to indicate that each of the siderails on both sides of the patient's bed should be in the up position. The bed periodically sends a signal to system 112 to indicate the position of the siderails and if system 112 detects that any of the siderails have been lowered, then an alarm condition is considered to exist and system 112 reacts to notify the appropriate caregiver or caregivers.

Screen 222 has a Motor Lock Out window 270 which includes therein an "All controls should be locked out (except emergency)" check box 272, a "Hi-Lo controls should be locked out" check box 274, a "Head position controls should be locked out" check box 276, and a "Knee position controls should be locked out" check box 278. Selection of check box 272 locks out the associated bed's patient controls associated with the motors of the bed that raise and lower the upper frame, which carries the bed mattress, relative to a base frame of the bed. Selection of box 276 or box 278 locks out the associated bed's patient controls associated with the motors of the bed that raise and lower the bed's head section or thigh section, respectively. Selection of box 272 locks out all of the patients controls associated with all of the bed's motors.

Window 270 also includes a Save button 280, a Reset button 282, and a Cancel button 284. Selection of button 280 saves the settings that have been made to screen 222 and system 112 responds with a pop-up window requesting confirmation to verify that the changes made to the template are for the associated patient only and not for all patients to which a Fall Prevention template configuration has been applied. Selection of Reset button 282 returns page 222 to the default condition that exists for the Fall Prevention template configuration, but page 222 continues to be displayed. Selection of Cancel button 284 returns the user back to the previous screen (i.e., the screen seen by the user prior to screen 222) and any changes made by the user to screen 222 are not applied. On some of the available template configuration screens of system 112, one or more numerical quantities representing associated threshold values above which or below which an alarm is to be generated can be entered on the associated template configuration screen. For example, a number indicating a maximum permissible head section angle may be entered on some template configuration screens.

The following are exemplary of the types of wireless communications initiated by system 112 in response to data received by system 112 matching one or more of the alarm conditions selected on one or more Care Alert templates: paging a pager (with or without an associated text message indicating the alarm condition and patient room number); sending a selected preprogrammed audio message to caregivers who are carrying one of badges 146 or one of handsets 168; sending a text message to badges 146, handsets 168, or other wireless communication devices (PDA's, cell phones, etc.) having text messaging capability; and sending a preprogrammed audio message to an audio station 158 at the location where an assigned caregiver is determined to be by one of locating-and-tracking systems 141, 167. Thus, when an alarm condition occurs, regardless of its priority level, system 112 operates to notify one or more caregivers of the alarm condition automatically via a page and/or text message and/or audio message. Thus, no one at the Master Nurse Station needs to take any further action to notify assigned caregivers of alarm conditions. If desired, however, the caregiver at the Master Nurse Call Station may follow up with one or more assigned caregivers by contacting them directly from Call Management screen 170 as described above. A database of system 112 stores information about the types of wireless communication devices carried by each of the caregivers and system 112 operates to initiate the appropriate type of wireless communication based on the particular type of wireless communication device carried by the associated caregiver.

With regard to a nurse call placed by a patient, or occurrence of an alarm condition, which is to be communicated to an assigned caregiver carrying one of badges 146 or handsets 168 having voice communication capability, a dialing string is generated and transmitted by system 112 in some embodiments so that, if the caregiver chooses to speak with the patient (or other caregivers in the room) via the associated audio station 158, the associated communication server 134, 136 is able to determine which audio station 158 is to be contacted. For example, the dialing string may be in the format of PBX trunking card number, room number (e.g., 81, 104). The dialing string appears on the associated display screen of badge 146 or handset 168, as the case may be, and the caregiver may select the dialing string to establish the communication link with the designated audio station 158.

As indicated in the table provided above, system 112 also has Care Alert templates related to surface therapy, bed maintenance, patient care, and reminders. With regard to the each of these other templates, each associated alarm condition may be assigned high, medium, or low priority. The description above of these priority levels in connection with the bed status template of FIG. 14 is applicable as well to the other Care Alert templates. In connection with surface therapy templates, surface therapy modes named prevention, pressure relief, opti-rest, and comfort are listed in the exemplary table. Each of these modes relate to the manner in which an air surface, such as an air mattress, is controlled. Such air surfaces have inflatable bladders but may also include other types of patient-support elements, such as foam, gel materials, engineered mesh fabric (such as Spacenet™ material), and the like.

The Prevention mode refers to therapy modes associated with various types of therapy surfaces, such as low-air-loss therapy, continuous lateral rotation therapy, and alternating pressure therapy. These sorts of therapies are generally intended to prevent patients from developing decubitus ulcers, also known as pressure sores, and other complications associated with long term immobility. The pressure relief mode refers to situations where a surface, such as a mattress, is controlled so as to reduce interface pressure by inflating or deflating one or more bladders or zones of bladders so as to maintain a predetermined target pressure (within a tolerance range). The opti-rest mode refers to a mode in which zones are sequentially deflated to a lower target pressure for a period of time and then re-inflated back to the original target pressure. For example, in a mattress having head, seat, and leg zones, the opti-rest mode comprises deflating and re-inflating the head zone, then deflating and re-inflating the seat zone, then deflating and re-inflating the leg zone, and then repeating the sequence. The comfort mode refers to situations where an air surface is simply controlled to a target pressure which the patient or caregiver has selected.

A wide variety of alarm conditions to which caregivers are to be alerted and that are associated with each of the modes of the surface therapy template screens may be configured using system 112. The type of alarm conditions to include on a template screen depends upon the functionality of the surface on which a particular patient rests. Alarm conditions may be configured on a template for situations where a therapy is terminated prematurely, where a therapy continues after it should have terminated, where pressure in a bladder or zone of bladders exceeds a threshold entered into system 112 by a user, and where pressure in a bladder or zone of bladders falls below a threshold entered into system 112 by a user. Other alarm conditions on the surface therapy template may be based on siderail position (e.g., a siderail is lowered during rotation therapy) or bed frame position (e.g., the head section is raised during a therapy).

The surface therapy portion of the above table also lists percussion, turn assist, and vest as parameters for which alarm conditions may be configured using a surface therapy template. Percussion therapy refers to pulsing one or more bladders of an air mattress situated beneath a chest region of a patient at a fairly high frequency so as to prevent build up of fluid in the patient's lungs. As indicated in the above table, different percussion therapies are provided (listed as Therapy 1, Therapy 2, and Therapy 3 in the table). Each therapy may have a pulse frequency, a pulse amplitude (e.g. peak pressure), and therapy duration, for example. Thus, alarm conditions associated with percussion therapy may include detection of a frequency that is too high or too low, a pressure in one or more of the percussion bladders that is too high or too low, the therapy is terminated prematurely, and the therapy continues after it should have terminated.

With regard to turn assist (which is not an ongoing therapy, but rather is used to turn the patient on their side in order to change bed sheets, change a wound dressing, or remove/insert a bed pan, for example), the frequency with which the patient should be turned may be entered in the appropriate field of the template as indicated in the above table. It should be noted that the turning frequency indicates, for example, how often a bed pan should be changed or how often a wound dressing should be changed. A caregiver initiates the turn assist function of the surface by manipulating controls on the bed, usually on one or more of the bed siderails. Thus, system 112 periodically alerts caregivers that it is time to go to a patient's room to turn the patient for the associated reason (dressing change, bedpan change, etc.). The time period between such alerts may be entered on the associated template screen in the hours, minutes format, for example.

The vest parameter of the surface therapy template refers to high frequency chest wall oscillation (HFCWO) therapy which is delivered by a vest worn by a patient. The vest includes one or more bladders that are oscillated pneumatically at very high frequency (e.g., about 5 Hertz to about 25 Hertz) above ambient pressure to induce the patient to cough to expel sputum. As indicated in the above table, different HFCWO therapies are provided (listed as Therapy 1, Therapy 2, and Therapy 3 in the table). Each HFCWO therapy may have an oscillation frequency, a baseline pressure (i.e., a pressure about which the pressure in the vest bladder oscillates), and a therapy duration. Thus, alarm conditions associated with HFCWO therapy may include detection of an oscillation frequency that is too high or too low, a baseline pressure that is too high or too low, the therapy is terminated prematurely, and the therapy continues after it should have terminated.

In connection with the bed maintenance templates, exemplary alarm conditions to which caregivers may be alerted include disconnection of a bed from a wall (such as unplugging the AC power plug or unplugging a nurse call cable), notification that a component of the bed (motor, circuitry, or sensors, for example) has failed (e.g., no longer operates or is not operating properly or is too hot), and notification of movement of the bed to a new location (as indicated by a locating-and-tracking system or based on other wireless transmissions from the bed, for example). In connection with the patient care templates, exemplary alarm conditions to which caregivers may be alerted include notification to if a head section of a bed is not within minimum and maximum angles (min and max thresholds entered by caregiver on template screen), notification that a head section of the bed has been moved by more than a threshold amount of degrees, notification that the bed has moved into or out of a Trendelenburg position or reverse Trendelenburg position or flat position, notification that the patient should be moved up in chair periodically for a selected period of time and at a head section angle between minimum and maximum thresholds. In connection with the reminders template, exemplary alert conditions to which caregivers may be alerted include notification that a patient has moved (as detected by a load cell based patient movement detection system included in the bed, for example), notification that a patient's restraint orders need to be renewed, and notification that it is time (or will soon be time) to check on the patient.

According to this disclosure, equipment other than hospital beds 159 may couple to ports in hospital rooms and send alarm signals to system 112 via the ports when the equipment detects its own alarm condition. Such equipment may include any equipment used in the care of a patient, including patient vital signs monitors, equipment that monitors other patient physiologic conditions, ventilators, and IV pumps, just to name a few. In some embodiments, system 112 does not evaluate data received from other equipment via the ports to determine whether or not an alarm condition exists. In such embodiments, if a signal is received by system 112 from such equipment via the ports, then an alarm condition is, in fact, occurring. In one embodiments, system 112 does evaluate the data received from the ports to determine if alarm conditions are occurring by comparing the data received from the ports to the alarm conditions programmed using the associated template screens. In still other embodiments, system 112 does not evaluate data from some ports and does evaluate the data from others. In the one embodiment, three ports (named Port 1, Port 2, and Port 3 by system 112) are included in each patient room, although any number of ports are contemplated by this disclosure. When a piece of equipment is coupled to one of the ports, system 112 receives data indicating the capabilities of the piece of equipment, either after querying the piece of equipment for such data or as a result of the piece of equipment transmitting the data automatically in response to being connected to the associated port. Such data includes data indicative of the type of equipment coupled to the port, the capabilities of the equipment, and the status of the equipment.

One of the Care Alert templates according to this disclosure permits users to type in the name of each alarm being received at each of the ports and to designate whether or not automatic notification to the wireless communication devices carried by designated caregivers is to be initiated by system 112 in response to receipt of an alarm signal from one or more of the ports in the rooms. These generalized equipment alarm templates may be set up differently for different patients, or not at all, as desired. When a generalized equipment template has been set up for a patient, system 112 assigns the name "Equipment Template for [Patient Name]." The customized equipment templates can be accessed from the Whiteboard screen (discussed below in connection with FIG. 15) or via the Edit Menu on the Menu Toolbar. On the generalized equipment templates, alarm priority (high, medium, or low) may be assigned for the alarms received via each of the ports in the room. The communication initiated to the wireless communication devices carried by designated caregivers in response to a generalized equipment alarm may include a text message including the name of the alarm for the associated port as typed in by the user when setting up the generalized equipment Care Alert template.

Referring now to FIG. 15, a Whiteboard screen 286 provides an overview of the patients and room status of the associated unit. Screen 286 includes a list of room numbers, patient names, the names of the primary caregiver assigned to the patient, the caregiver number, each patient's attending physician, and location of any caregivers tracked by system 141. In the illustrative example, the patient's names are presented on screen 286 in an encrypted format in which the first two letters of the patient's last name appear first with the first letter capitalized, then followed by a set of ellipses, then followed by the last letter of the patient's last name capitalized, then followed by the first letter of the patient's first name in a lower case letter. Call buttons 192 and page buttons 194 are provided next to each assigned caregiver's name and number. Buttons 192, 194 operate the same on screen 286 as was described above in connection with screen 170. An alert icon 288 appears in window 286 next to the patient's name in any rooms in which an alarm condition is detected by system 112. If the alarm condition has a High priority level, icon 288 is red and white (i.e., a red button with a white image of a bed therein) and flashes. If the alarm condition has a Medium priority, icon 288 is yellow and black and flashes. If the alarm condition has a Low priority, icon 288 is yellow and black and is static. If multiple alarms associated with a particular patient occur, then multiple icons 288 appear next to the patients name on screen 286.

Figure 16:
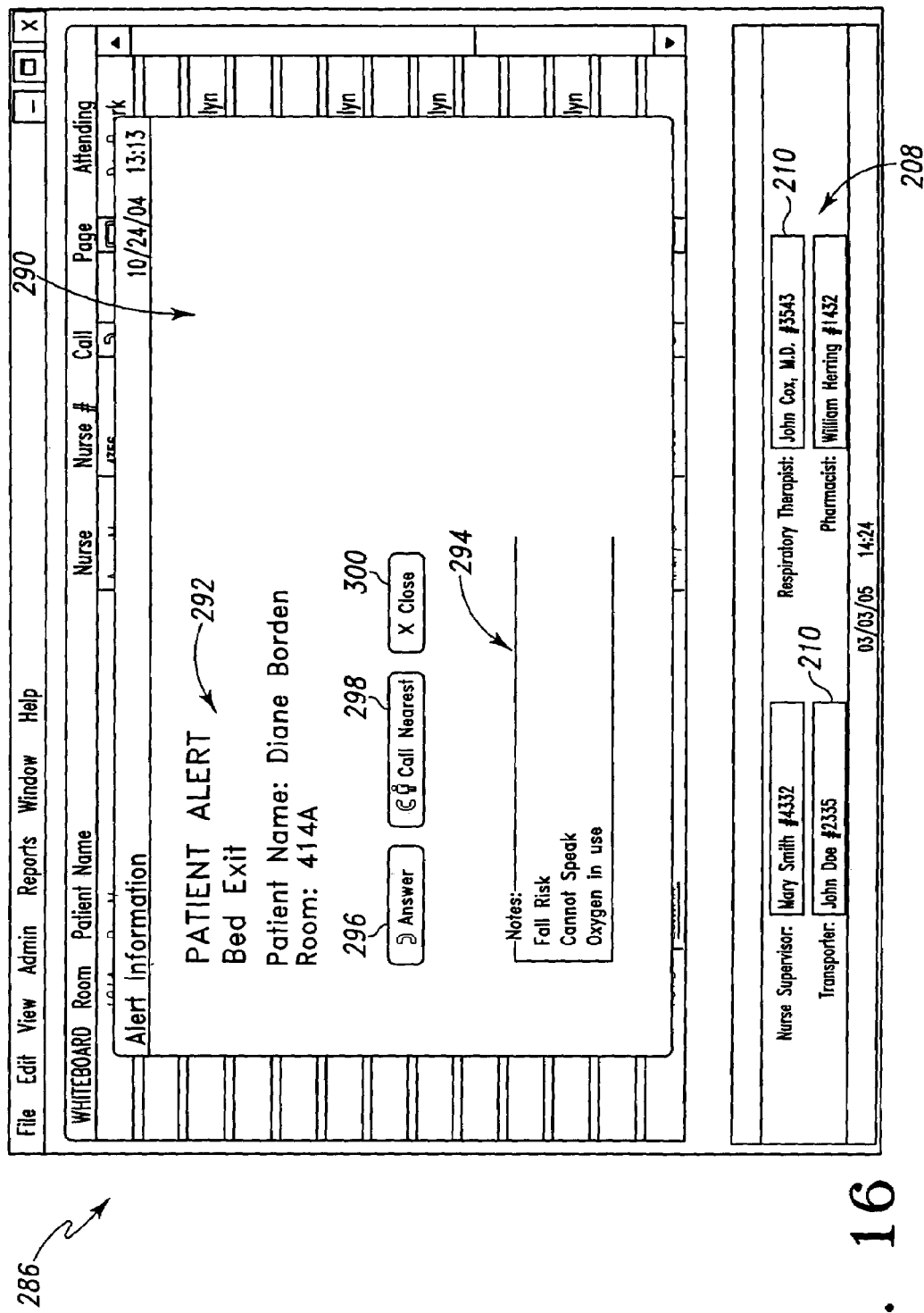
FIG. 16 is a screen shot showing an Alert Information pop-up window appearing as a result of an alert icon of the Whiteboard screen being selected.

If the caregiver at the Master Nurse Call Station selects icon 288, system 112 responds with an Alert Information pop-up window 290, an example of which is shown in FIG. 16. Window 290 includes a text block 292 which indicates the type of alarm that is occurring. Also shown in window 290 is the name of the patient in a non-encrypted format and the patient's room number. Illustratively, the patient's name and room number appear beneath text block 292. Window 290 also has a Notes text block 294 in which notes about the particular patient are shown. In the illustrative example, the notes indicate that the patient is a fall risk, cannot speak, and is using oxygen.

Window 290 also has therein an Answer button 296, a Call Nearest button 298, and a Close button 300. If button 296 is selected, system 112 responds by establishing a communications link between the Master Nurse Call Station and the Audio Station 158 at the location of the patient associated with the alarm condition. If button 298 is selected, system 112 responds by establishing a communication link between the Master Nurse Call Station and the Audio Station 158 at the location where the nearest caregiver assigned to the patient associated with the alarm condition is located or with one of devices 146, 168 if the nearest caregivers is carrying one of devices 146, 168. If button 300 is selected, system 112 responds by closing window 290.

As discussed above, the alarm conditions which result in alarm notifications being sent to the Master Nurse Call Station and to assigned caregivers are programmable using various Care Alert Template screens. Some of the Care Alert Template screens are configured in accordance with Standard of Care (SOC) parameters which are routinely followed to provide different levels of care to patients with different medical conditions. Different alarm conditions are associated with the different SOC's. For example, it may desirable for patients coming out of surgery to lie flat for one hour and then recline at a bed head section elevation of fifteen degrees for two hours and then remain in bed for an additional four to six hours.

With the foregoing in mind, it is contemplated by this disclosure that Care Alert Template screens are configurable so that as SOC's change or progress at selected time intervals, system 112 automatically switches at the appropriate times from one SOC Care Alert configuration to the next SOC Care Alert configuration having different alarm parameters. Referring back to the above-described example, a first Care Alert configuration will result in an alarm being detected by system 112 if the head section angle and/or other bed deck sections are not in positions allowing the patient to lie flat; a second Care Alert configuration will result in an alarm being detected by system 112 if the head section of the bed is not at fifteen degrees of elevation (plus and/or minus a tolerance range in some embodiments); and a third Care Alert configuration will result in an alarm being detected by system 112 if the bed's scale system detects that a patient is about to exit the bed or has exited the bed.

After the progressive SOC sequence is initiated, such as by the hospital bed detecting via its scale system that the patient has moved onto the bed (i.e., the patient has returned to the bed after surgery) or by one or more user inputs made by a caregiver at the Master Nurse Call Station or by a signal received by system 112 which originates from a wireless communication device carried by a caregiver or from an audio station 158, system 112 will apply the first Care Alert configuration for a first time interval (one hour in the example) and thereafter automatically switch to the second Care Alert configuration for a second time interval (two hours in the example) and thereafter switch to the third Care Alert configuration for a third time interval (four to six hours in the example). When system 112 switches from the first Care Alert configuration to the second Care Alert configuration, a transition period may be programmed during which a reminder is sent to the patient's assigned caregiver to notify the caregiver that the head section of the bed should be raised to fifteen degrees. If, after the transition period, the head section has not been raised, then system 112 will detect the alarm condition and respond accordingly. If desired, system 112 may be programmed so that a message or reminder is communicated to the patient's assigned caregiver a programmed period of time before a Care Alert configuration is scheduled to end and/or before another Care Alert configuration is scheduled to begin.

While the time intervals in the given example are different time intervals, it is within the scope of the disclosure for two or more of the time intervals to be the same amount of time. Furthermore, although in the given example, the time intervals are measured after system 112 is triggered to initiate the SOC sequence, it is within the scope of this disclosure for particular starting and ending times (for example, 2:30 p.m. as the starting time and 3:47 a.m. as the ending time) to be entered into appropriate fields when configuring the associated Care Alert templates. Thus, it is possible for two or more Care Alert configurations to be active for a particular patient at the same time when the time intervals for the two or more Care Alert configurations overlap. Two or more Care Alert configurations may be separated by an interim period of time. It is within the scope of this disclosure for users to program system 112 via the Care Alert screens so that the priority level to be assigned to a particular detected alarm varies over time. It will be appreciated that the number, type, and duration of Care Alert configurations in the SOC sequence are practically limitless in accordance with this disclosure and are at the discretion of the caregivers operating system 112.

In accordance with one embodiment of system 112, the alarm parameters entered and/or selected on the Care Alert screens are stored in memory of server 114 and/or PC's 118 of system 112. Thereafter, system 112 operates in accordance with application software to compare the data received from the multiple beds by system 112 to the alarm parameters stored in memory to determine whether any alarm conditions exist in connection with any of the beds being monitored by system 112. In this embodiment, therefore, the beds transmit to system 112 all available bed data for monitoring by system 112. Depending upon how the Care Alert screens have been configured, some of the bed data transmitted by the beds may not be associated with any of the conditions that system 112 is monitoring. Thus, in some embodiments, one or more of the beds are programmable to avoid sending extraneous bed status data to system 112. In such embodiments potential bandwidth issues in system 112 and network 110 are reduced since less data is transmitted to system 112 from the associated beds.

In some embodiments of system 112 in which beds are programmable, once the Care Alert screens are configured with the alarm parameters for a particular bed, system 112 notifies the bed as to the type of bed parameters system 112 has been programmed to monitor (hereinafter referred to as "monitored parameter types"). The bed stores the monitored parameter types in memory associated with the bed and thereafter, the bed operates to transmit to system 112 data associated only with the monitored parameter types and does not transmit any data associated with parameters not being monitored by system 112. It is understood that some types of bed data may always be transmitted to system 112, such as bed identification (ID) data, regardless of the types of parameters that system 112 has been programmed to monitor via the configuration of the Care Alert screens. After system 112 receives the data associated with the monitored parameter types, system 112 compares the received data to the alarm parameters stored in memory of system 112 to determine whether any alarm conditions exist. Thus, in these embodiments, system 112 determines whether or not alarm conditions exist based on periodic data transmitted by the bed, but the bed will only transmit the bed data that system 112 has programmed the bed to transmit (i.e., the bed will periodically transmit only a subset of the available bed data based on commands received from system 112).

In other embodiments of system 112 in which beds are programmable, once the Care Alert screens are configured with the alarm parameters for a particular bed, system 112 notifies the bed of the alarm parameters and the bed stores the alarm parameters in its memory and operates to monitor itself by comparing the appropriate bed data to the alarm parameters to determine whether an alarm condition exists. If an alarm condition is detected by the bed, then the bed sends an alarm signal to system 112 to notify system 112 of the alarm condition, otherwise the bed does not transmit to system 112 the data associated with the parameters which the bed has been programmed by system 112 to monitor. Thus, until the bed determines that an alarm condition exists, the associated bed data is not sent to system 112 which reduces the amount of data being communicated to system 112 thereby reducing the potential for bandwidth problems.

In still other embodiments, a first subset of bed data is transmitted to system 112 and system 112 operates to determine whether an alarm conditions exists for the parameters associated with the first subset of bed data and the bed operates to determine whether an alarm condition exists for parameters associated with a second subset of bed data in which case, the bed notifies system 112 of the alarm condition. Regardless of how system 112 detects that an alarm condition exists, system 112 responds in accordance with its programming to alert the appropriate caregiver(s) of the alarm condition as described above.

Figure 17:
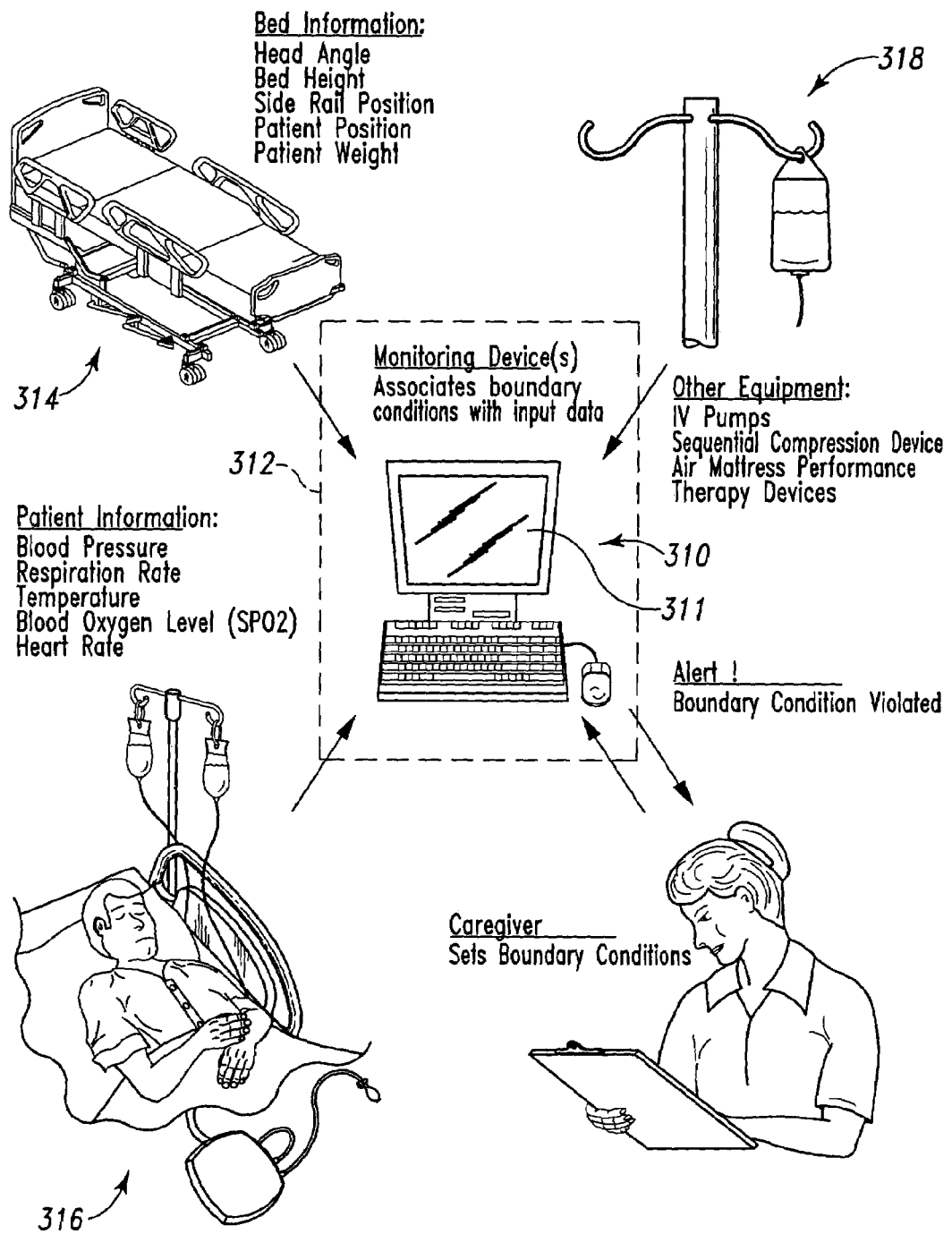
FIG. 17 is a diagrammatic view showing a hospital network having one or more computer devices that receive data from one or more beds, one or more other pieces of equipment, and one or more patient monitoring devices and that communicate alarm conditions to one or more caregivers based on alarm condition thresholds set by the one or more caregivers.

Referring now to FIG. 17, one or more computer devices 310, such as PC's or servers or any other devices capable of executing software, are included as part of a computer network 312 and receive data from one or more hospital beds 314, patient monitoring equipment 316 that senses one or more patient physiological parameters, and one or more other pieces of medical equipment 318. One or more of computer devices 310 have a respective display screen 311 associated therewith. As indicated in FIG. 17, types of data received from beds 314 include data relating to the following: head angle (i.e., the angle that a head section of the bed is elevated relative to some other portion of the bed), bed height, side rail position, patient movement or position, and patient weight. This list is not exhaustive and it is within the scope of this disclosure for all types of data monitored by or accessible to circuitry of a hospital bed to be communicated to devices 310 of network 312.

Examples of monitoring equipment 316 which communicate data to devices 310 include, for example, blood pressure measuring devices, respiration rate measuring devices, temperature measuring devices, pulse oximeters, electrocardiograms (EKG's), and electroencephalograms (EEG's). As contemplated by this disclosure, equipment 316 includes equipment of all types that measure patient physiological conditions. Examples of other pieces of medical equipment 318 which communicate data to devices 310 include, for example, IV pumps, sequential compression devices such as those having inflatable sleeves worn on limbs (usually, the legs) of patients and that are inflated and deflated sequentially to treat or prevent Deep Vein Thrombosis (DVT), air mattresses including those that perform therapies (alternating pressure, continuous lateral rotation therapy, pulsation, vibration, low air loss), and other therapy devices such as passive motion devices, ventilators, and the like. As contemplated by this disclosure, equipment 318 includes equipment of all types that are used in connection with the care and/or treatment of patients.

One or more of devices 310 includes software that permits caregivers to program alarm conditions (sometimes referred to herein as "boundary conditions") for not only beds 314 but also for one or more of the pieces of equipment 316, 318 coupled to network 312. Such programming of the alarm conditions using devices 310 is substantially similar to the programming that occurs using Care Alert templates as described above. In some embodiments, the alarm conditions for beds 314 and equipment 316, 318 are programmable using a single PC 310 which may be located at a Master Nurse Call Station as part of a nurse call system of network 312. Care Alert templates for equipment 316, 318 may be configured in accordance with Standards of Care (SOC's) in a manner similar to the manner in which Care Alert templates for beds are configured as described above. Therefore, the above discussion regarding progressive SOC's (i.e., progressing from one SOC to another SOC on a time basis) is applicable to equipment 316, 318 as well as to beds 314. Accordingly, various alarm conditions for beds 314 and one or more pieces of equipment 316, 318 may be preconfigured in Care Alert templates associated with patient status or acuity level (i.e., the medical condition of the patient). To set all of the boundary conditions for a particular bed 314 and associated equipment 316, 318, a caregiver may simply input into one of devices 310 the patient status or acuity level. In addition, the above discussion regarding programming monitored parameter types so that not all available is transmitted to the network or programming a bed to monitor itself and only transmit certain data in response to the bed detecting an alarm condition is applicable to equipment 316, 318 as well.

Figure 18:
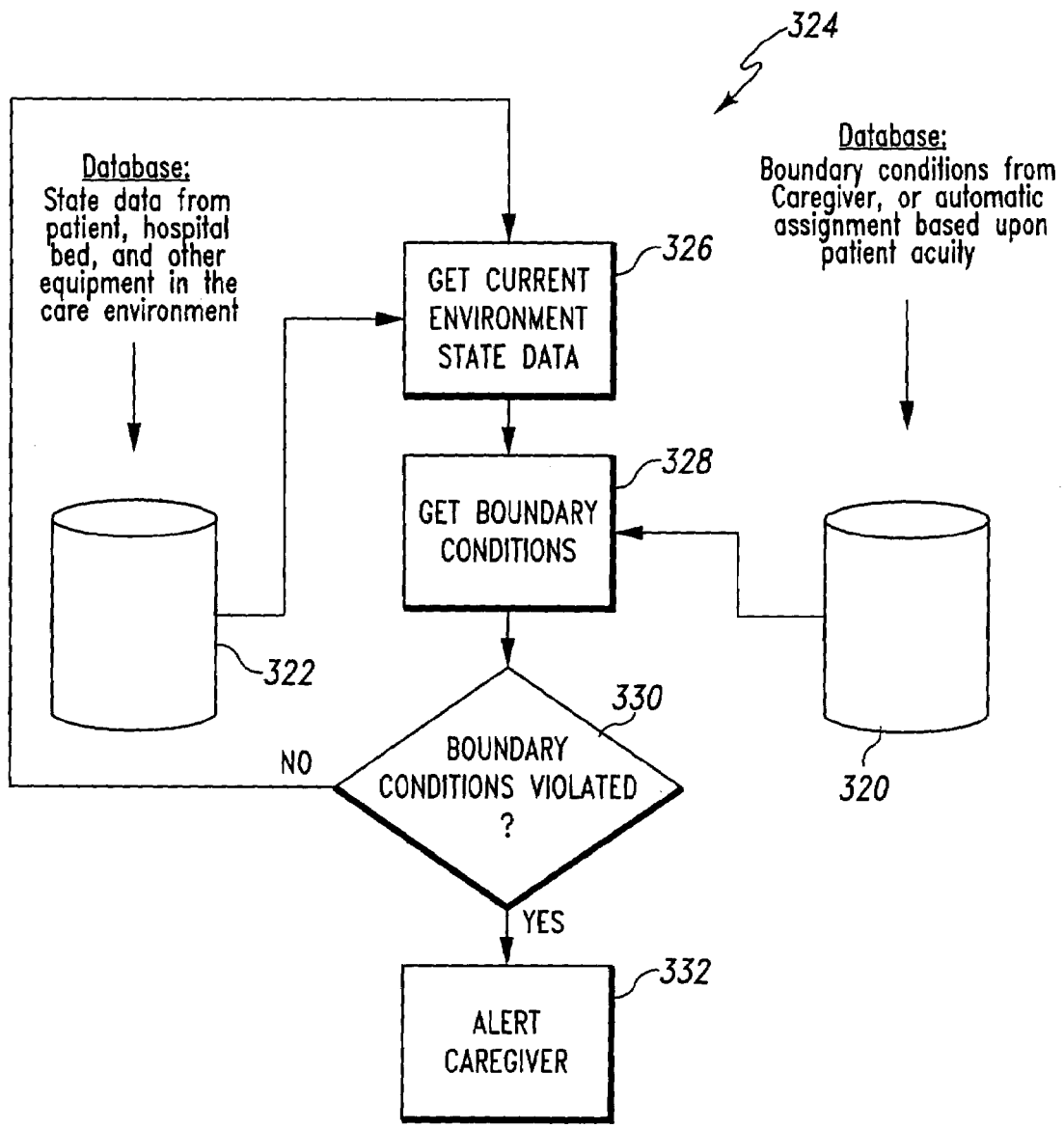
FIG. 18 is a flow chart showing an algorithm that is executed by the computer device(s) of FIG. 17 to determine whether an alarm condition exists based on a comparison of data from a current state database to data in a boundary condition database.

The boundary conditions programmed by caregivers for beds 314 and equipment 316, 318 are stored in one or more databases 320, shown diagrammatically in FIG. 18, which may be resident on the same device 310 that a caregiver uses to program the boundary conditions or on one or more other devices 310 of network 312. The data to be monitored, which is transmitted to network 312 by beds 314 and equipment 316, 318, is stored in one or more databases 322, also shown diagrammatically in FIG. 18, which is resident on one or more of devices 310 of network 312.

An algorithm 324 which is included in software that is executed by one or more of devices 310 is shown in FIG. 18. According to algorithm 324 state data associated with one of the conditions being monitored is retrieved from database 322 as indicated at block 326 and boundary condition data associated with the monitored conditions is retrieved from database 320 as indicated at block 328. A comparison is then made to determine whether the state data violates the boundary condition (e.g., alarm threshold) as indicated at block 330. Depending upon the type of condition associated with the retrieved state data, a boundary condition violation may be considered to exist if state data is greater than, greater than or equal to, less than, less than or equal to, equal to, or not equal to the boundary condition. Thus, the logic of algorithm 324 in connection with the comparison made at block 330 is at the discretion of the software programmer and will likely vary for different types of state data and associated boundary conditions.

If at block 330 it is determined that an alarm condition exists (i.e., the state data violates the boundary condition), then one or more assigned caregivers are alerted of the alarm condition as indicated at block 332. Devices 310 or network 312 operate to alert caregivers of alarm conditions in any of the manners described above. If at block 330 it is determined that an alarm condition does not exist (i.e., the state data does not violate the boundary condition), then algorithm 324 proceeds back to block 326 to retrieve the next state data for comparison to its associated boundary condition.

Figure 19:
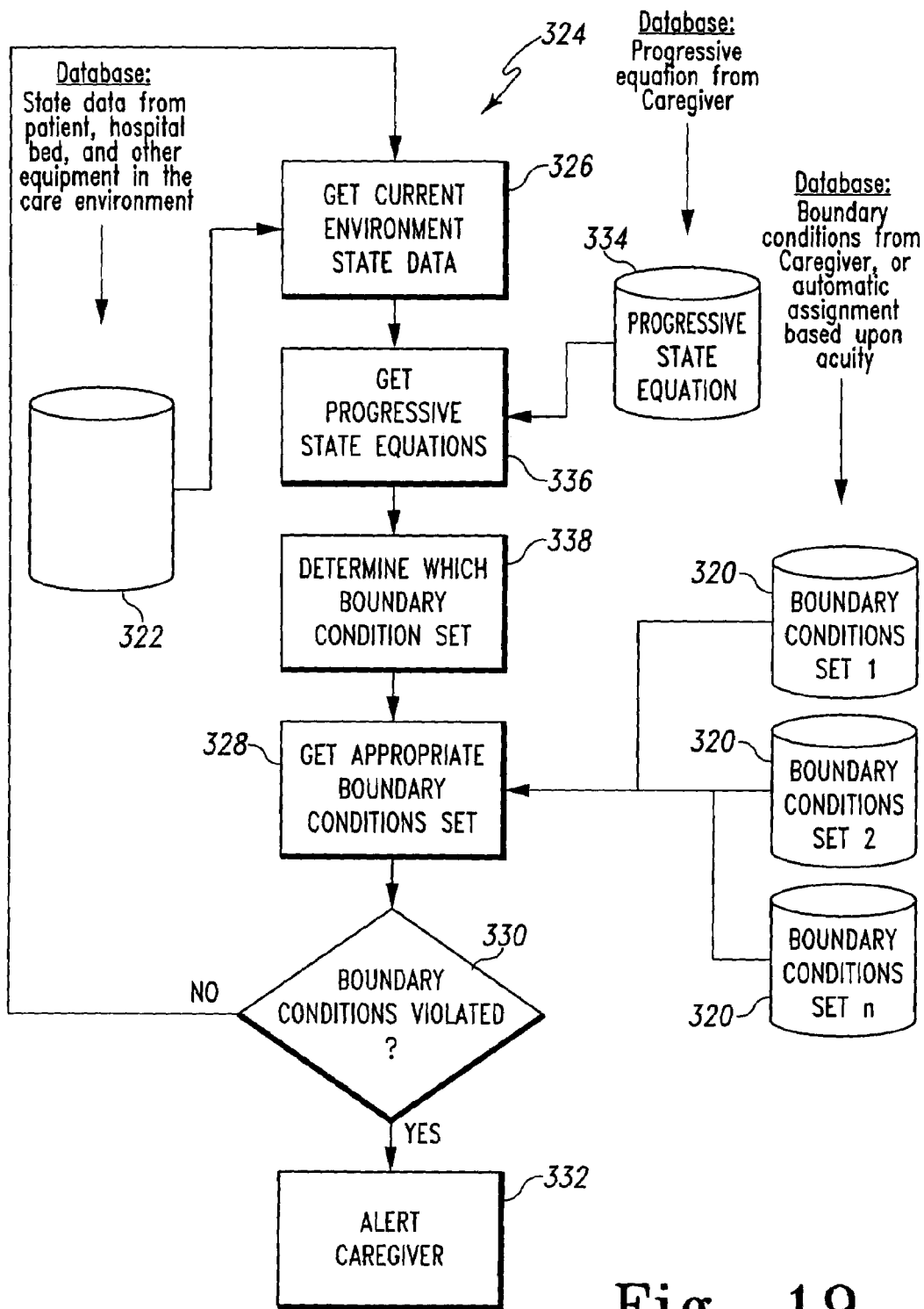
FIG. 19 is a flow chart showing an algorithm, similar to the algorithm of FIG. 18, but having multiple boundary conditions databases and having a progressive state equation database in which is stored data about Care Alert configurations that are to be applied at different times.

If progressive SOC templates are programmed, then algorithm 324 is modified to include some extra steps as shown in FIG. 19. In FIG. 19, database 320 is shown as three separate databases 320 which include respective boundary conditions sets one, two, and three. If progressive SOC templates are programmed, then data regarding the SOC progression is stored in one or more databases 334. After retrieving state data at block 326, data from database 334 is retrieved as indicated at block 336 and then the device 310 running algorithm 324 proceeds to determine which boundary condition set is applicable as indicated at block 338. Thereafter, the device 310 running algorithm 324 retrieves the appropriate boundary conditions set from the boundary condition sets stored on databases 320 as indicated at block 328 and proceeds as described above to determine whether a boundary conditions is violated at block 330 and, if so, to alert one or more caregivers of the violation at block 332.

As mentioned above, hospital beds in accordance with this disclosure may communicate with a network in a healthcare facility via wired and/or wireless connections. Some prior art hospital beds do not include the appropriate hardware and/or software to communicate with a hospital network using Ethernet protocols such as TCP/IP, for example. Some hospital beds include data output ports that are connectable via cords or cables to interface units of a nurse call system and these hospital beds may transmit bed status data according to a particular interface protocol different than a standard Ethernet protocol. Such a hospital bed that communicates with a nurse call system is shown, for example, in U.S. Pat. No. 6,362,725.

Figure 20:
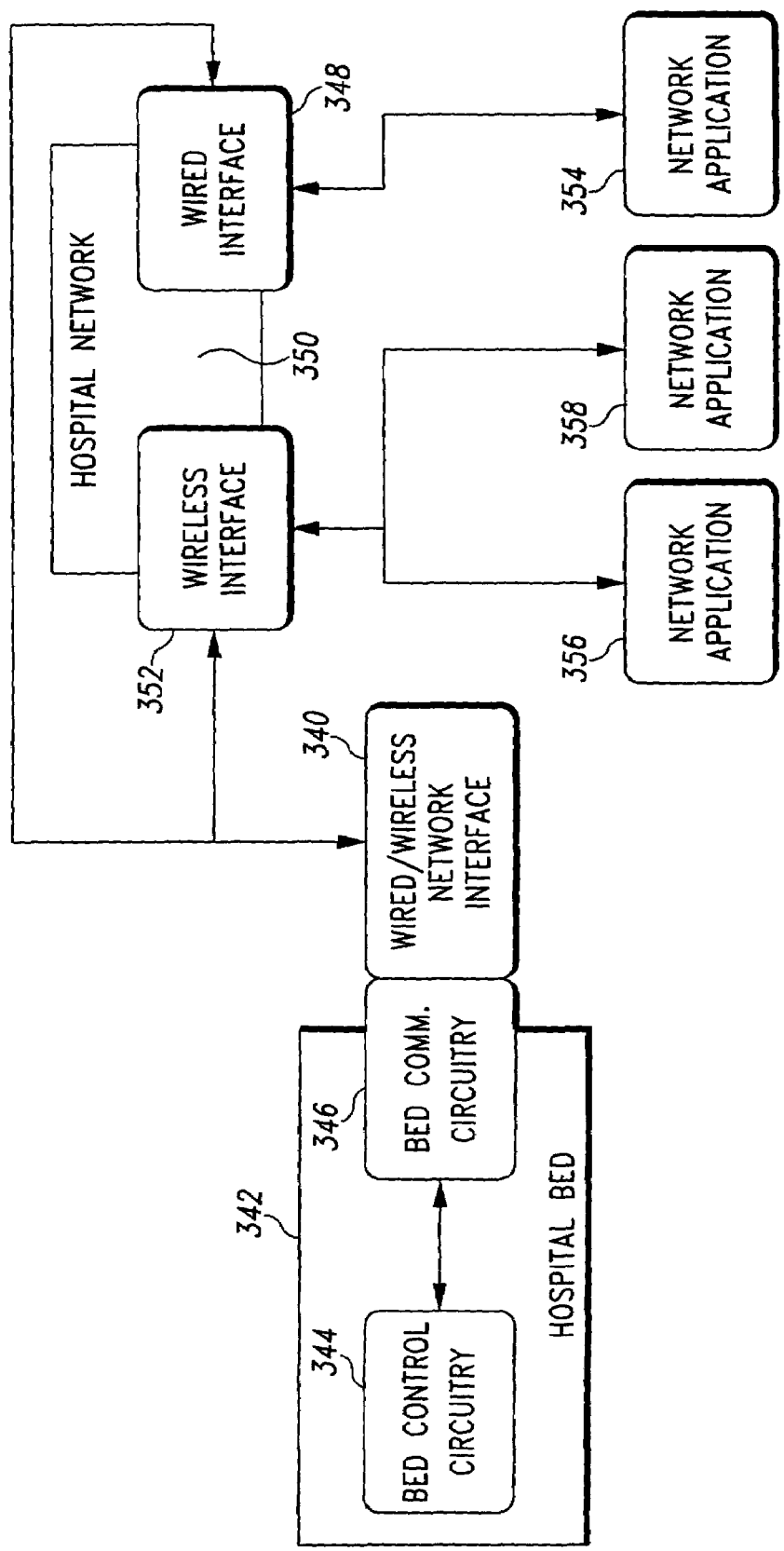
FIG. 20 is a block diagram showing a hospital bed having bed communication circuitry and a wired/wireless network interface unit that is coupled to the bed communication circuitry and that is configured for communication with a hospital network via a wired interface and/or a wireless interface.

According to this disclosure a network interface unit 340 couples to a hospital bed 342 as shown in FIG. 20. Bed 342 includes bed control circuitry 344 which controls the various functions of bed 342 and that monitors the status of the various bed functions. Bed 342 also includes bed communication circuitry 346 through which bed status data is communicated. Bed communications circuitry 346 includes a communications port designed for mating with a connector of a nurse call cable, such as a cable having a 37-pin connector, which, in turn, couples to a nurse call system. Interface unit 340 couples to the connector of circuitry 346, such as via a pigtail connector extending from a housing of unit 340, in lieu of the nurse call cable.

Unit 340 includes protocol conversion circuitry that converts the data which is received from bed 342 and which is formatted according to a first protocol, such as the interface protocol described in U.S. Pat. No. 6,362,725, into a format according to a second protocol, such as a standard Ethernet protocol. Unit 340 includes a communications port, such as an RJ-45 port, which is coupleable via a cable to a wired interface 348 of a hospital network or Ethernet 350. Interface 348 is an RJ-45 in some embodiments. Unit 340 also includes circuitry for communicating wirelessly with a wireless interface 352 of Ethernet 350. In some embodiments, interface 352 comprises a wireless transceiver, such as an 802.11 access point like unit 144 shown in FIG. 10. Thus, data received from bed 342 by unit 340 according to the first protocol is sent to interface 348 and/or interface 352 according to the second protocol. In addition, data received by unit 340 from network 350 according to the second protocol is converted by unit 340 into the format associated with the first protocol and then forwarded on to circuitry 344 of bed 342 through circuitry 346. In some embodiments, unit 340 is configured to couple only to one or the other of interfaces 348, 352. In some embodiments, the protocol conversion circuitry is omitted from unit 340 such that data is transmitted by unit 340 according to the same protocol in which the data was received from bed 340 and network 350 transmits data to unit 340 according to this same protocol.

In the illustrative example, data communicated from unit 340 to wired interface 348 is provided to a first network application 354 and data communicated from unit 340 to wireless interface 352 is provided to a second network application 356 and to a third network application 358.

Network applications include, for example, nurse call system software, admission-discharge-tracking (ADT) system software, electronic medical records (EMR) system software, workflow system software, medical records archiving system software, and the like. It is contemplated by this disclosure that a first subset of bed data is communicated to interface 348, but not to interface 352, and that a second subset of bed data is communicated to interface 352, but not to interface 348. It is also contemplated by this disclosure that the same bed data is communicated to both interfaces 348, 352.

In some embodiments, unit 340 includes circuitry that determines whether or not unit 340 is coupled to interface 348. In such embodiments, if unit 340 is coupled to interface 348, then bed data will be communicated via the wired data link to interface 348 and no attempts will be made by unit 340 to communicate with interface 352. If, on the other hand, unit 340 is not coupled to interface 348, then bed data will be communicated via the wireless data link to interface 352. Unit 340 may be coupled to interface 348, for example, when bed 342 is stationary in a hospital room and unit 340 may be uncoupled from interface 348, for example, when bed 342 is being transported through a healthcare facility from one location to another. Thus, unit 340 permits wireless communication with network 350 during transport of bed 342.

Figure 21:
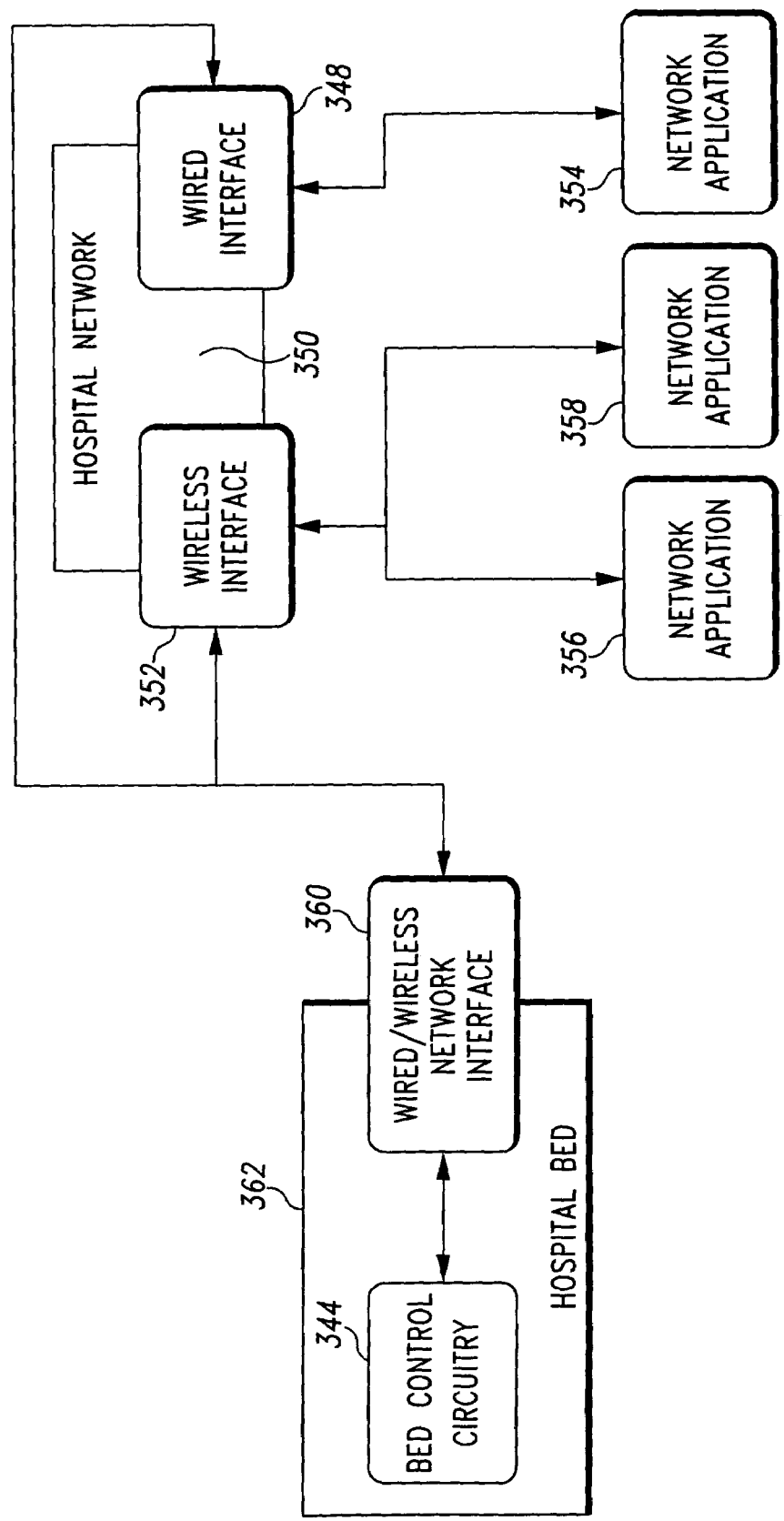
FIG. 21 is a block diagram, similar to FIG. 20, showing a wired/wireless network interface unit integrated into the circuitry of the bed.

Based on the foregoing description, it will be appreciated that units 340 may be used to retrofit existing hospital beds with the ability to communicate with a hospital Ethernet either wirelessly and/or via a wired connection according to an Ethernet protocol. However, hospital beds manufactured with the circuitry and functionality of units 340 included therein are within the scope of this disclosure as depicted in FIG. 21 in which a network interface unit 360 is included as part of a hospital bed 362. Portions of FIG. 21 that are the same as, or substantially similar to, like portions of FIG. 20 are denoted with like reference numerals. In some embodiments, network interface units 340, 360 may include connection ports for nurse call cables to provide feed through of bed data to legacy (i.e., existing) nurse call systems which are not otherwise able to communicate via the hospital Ethernet.

Figure 22:
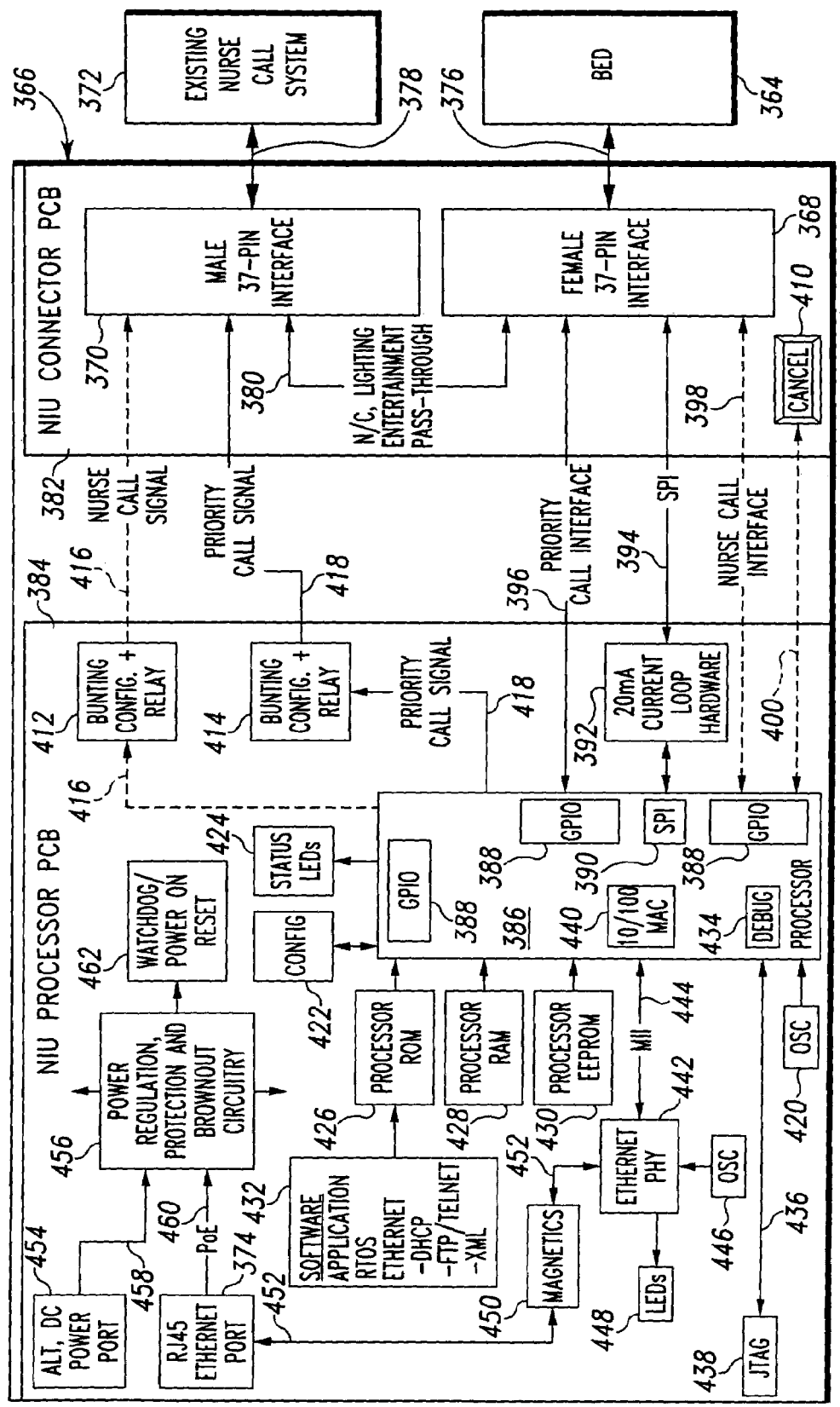
FIG. 22 is a block diagram of a network interface unit which has couplers for coupling to a bed, a nurse call system, and a hospital Ethernet.

A network interface unit 366 which is used with a bed 364, but which is not mounted to or integrated into the bed like units 340, 360 discussed above, includes a first coupler or connector 368 which is coupleable to bed 364, a second coupler or connector 370 which is coupleable to a nurse call system 372, and a third coupler or connector 374 which is coupleable to a hospital Ethernet as shown in FIG. 22. Unit 366 may be mounted, for example, to a room wall or to a head wall unit in a hospital room. In the illustrative example, coupler 368 comprises a female 37-pin interface that mates with a male 37-pin connector provided at the end of a cable extending from bed 364. Also in the illustrative example, coupler 370 comprises a male 37-pin interface that mates with a female 37-pin connector provided at the end of a cable that couples to nurse call system 372. Illustrative connector 374 comprises an RJ-45 Ethernet port which allows unit 366 to be coupled to the hospital Ethernet via an appropriate cable. Thus, connector 374 is sometimes referred to herein as "port 374."

When bed 364 is coupled to connector 368 and nurse call system 372 is coupled to connector 370, communications between bed 364 and nurse call system 372 take place over a first data link 376, a second data link 378, and a feed through data link 380. Data link 376 is established between bed 364 and connector 368. Data link 378 is established between connector 370 and nurse call system 372. Data link 380 is established between connector 368 and connector 370. While data links 376, 378, 380 are typically wired data links, it is within in the scope of this disclosure for one or more of data links 376, 378, 380 to be wireless data links, such as infrared (IR) or radio frequency (RF) data links. In the illustrative example, connectors 368, 370 are mounted to a connector printed circuit board (PCB) 382.

As mentioned above, connector 374 permits unit 366 to be coupled to a hospital Ethernet. Thus, data received from bed 364 and nurse call system 372 via data links 376, 378 may be transmitted to other devices included in the hospital Ethernet through port 374. Port 374 is coupled to a processor PCB 384 to which is also coupled a processor 386 which operates under software control to convert data received from bed 364 and system 372 from the received format into an appropriate format according to an Ethernet protocol, such as the TCP/IP protocol. Processor 386 has a set of general purpose input/output (GPIO) connectors 388 and a serial peripheral interface (SPI) connector 390. Connector 390 is coupled to 20 milliamp (mA) current loop hardware 392 which, in turn, is coupled to connector 368 for communication of a SPI signal 394. Connector 368 is also coupled to connectors 388 of processor 386 for communication of a priority call interface signal 396, a nurse call interface signal 398, and a nurse call cancel signal 400 which is received from a cancel button 410 that is coupled to PCB 382.

Connector 370 is coupled to connectors 388 of processor 386 through a first relay 412 and a second relay 414 for communication of a nurse call signal 416 and a priority call signal 418, respectively. Processor 386 is also coupled to an oscillator 420, a configuration module 422, and a set of status light emitting diodes (LED's) 424. Various memory devices, such as read only memory (ROM) 426, random access memory (RAM) 428, and an Electrically Erasable Programmable Read Only Memory (EEPROM) 430 are also coupled to processor 386. Various software applications 432 are stored in the memory devices for execution by processor 386. In the illustrative example, software applications 432 are stored in ROM 426 and include real time operating system (RTOS) software and Ethernet software such as Dynamic Host Configuration Protocol (DHCP) software, file transfer protocol (FTP)/telnet software, and extensible markup language (XML) software. The given software types are intended to be exemplary, not exhaustive. Therefore, it is within the scope of this disclosure for all types of software allowing communications between unit 466 and a hospital Ethernet to be stored in one or more of devices 426, 428, 430 and executed by processor 386.

Illustratively, processor 386 includes a debug module 434 which is coupled via a data link 436 to a Joint Test Action Group (JTAG) connector 438. A diagnostic device may couple to connector 438 and perform boundary scanning to read and set the value of the pins of processor 386 and optionally, to read and set the value of other devices on PCB 384 and/or the internal registers of processor 386. Illustrative processor further includes a 10/100 media access controller (MAC) module 440 which operates to permit unit 366 to communicate with the hospital Ethernet at a data transmission rate of 10 Megabits per second (Mbps) or 100 Mbps. Module 440 is coupled to an Ethernet physical layer (PHY) module 442 for communication of Media Independent Interface (MII) signals 444. Module 442 is coupled to an oscillator 446 and a set of LED's 448. Module 442 is also coupled to, or optionally includes, an electrical isolation device 450 such as a transformer. Device 450 electrically isolates the data signals communicated on a data link 452 between module 442 and connector 374.

Unit 466 includes an alternative direct current (DC) power port 454 which is coupled to power regulation, protection, and brownout circuitry 456 by one or more power conductors 458. Power from an external source is coupleable to port 454 and is used for operating the various components of unit 366. One or more power over Ethernet (PoE) conductors 460 are also coupled to circuitry 456 so that, if connector 374 is coupled to the hospital Ethernet, power from the Ethernet may be used for operating the components of unit 366. Circuitry 456 is also coupled to a Watchdog/Power On Reset circuit 462.

As mentioned above, unit 366 is coupleable via connectors 368, 370, 374 to bed 364, nurse call system 372, and the hospital Ethernet, respectively. In the illustrative example, nurse call system 372 does not communicate according to an Ethernet protocol, but rather unit 366 provides a connection between nurse call system 372 and the Ethernet and converts data from system 372 into the appropriate format for Ethernet communication. In alternative arrangements, nurse call system 372 is not coupled to connector 370 via data link 378, but rather nurse call system 372 is configured to communicate via an Ethernet protocol and sends data to, and receives data from, unit 366 via port 374. In such alternative arrangements, unit 366 converts the data received via port 374 from the nurse call system into the appropriate format for communication to bed 364 via connector 368 and data link 376.

Figure 23:
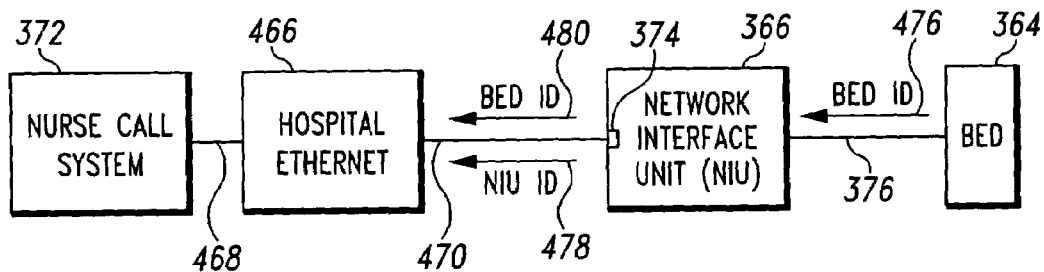
FIG. 23 is a block diagram showing a hospital bed coupled to a nurse call system through the network interface unit and the hospital Ethernet.
Figure 24:
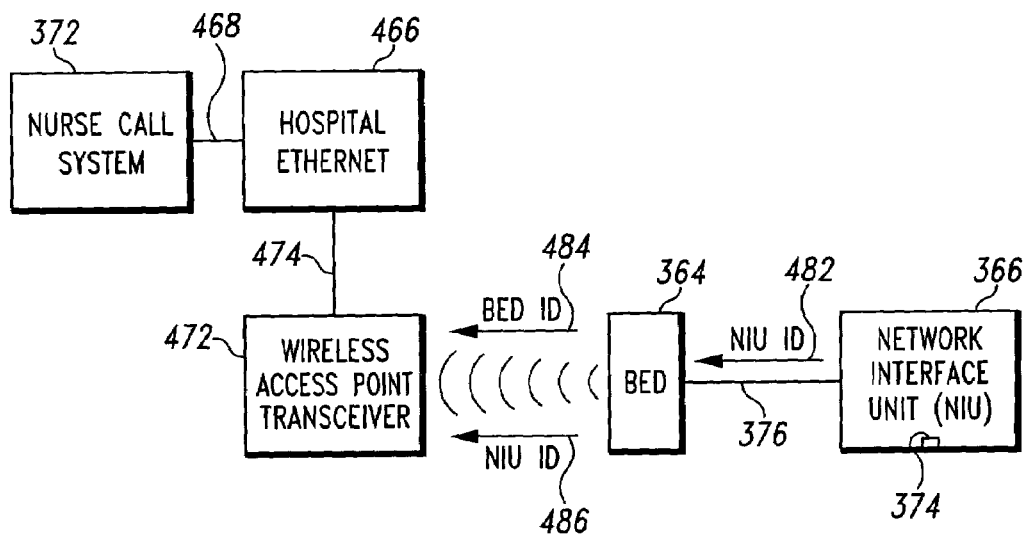
FIG. 24 is a block diagram showing a hospital bed coupled to the network interface unit and communicating wirelessly with the hospital Ethernet.

Referring now to FIG. 23, nurse call system 372 is coupled to a hospital Ethernet 466 via a data link 468 and bed 364 is coupled to network interface unit (NIU) 366 via data link 376. Unit 366 is, in turn, coupled to Ethernet 466 via a data link 470 which is coupled to port 374 of unit 366. Data links 376, 468, 470 are typically wired data links. However, it is within the scope of this disclosure for data links 376, 468, 470 to be wireless. Referring now to FIG. 24, an alternative arrangement is shown in which bed 364 is configured to communicate wirelessly with a wireless access point transceiver 472 that is coupled to Ethernet 466. Bed 364 communicates bidirectionally with transceiver 472 according to an appropriate Ethernet protocol and transceiver 472 communicates bidirectionally with Ethernet 466 via a data link 474.

It will be appreciated that a hospital will have multiple beds, similar to bed 364, and multiple network interface units 366 associated with the various beds. Each unit 366 is mounted at a particular location in a hospital. For example, one or more units 366 will be located in various patient rooms. Each bed 364 and each unit 366 is assigned a unique identification (ID) code, such as a serial number. In some embodiments, one or more of the computer devices of nurse call system 372 have software that operates to associate bed ID data with NIU ID data so that system 372 can keep track of which bed is located in each room of the hospital and convey this information to caregivers using system 372.

Processor 386 of unit 366 operates to determine whether or not port 374 is coupled to Ethernet 466. Depending upon whether or not the unit 366 is connected to Ethernet 466 via port 374, the data path of the bed ID data and the NIU ID data to nurse call system 372 is different. If unit 366 senses that port 374 is coupled to Ethernet 466 as shown in FIG. 23, for example, then the associated bed 364 sends its bed ID data to the unit 366, as indicated by arrow 476, and then unit 366 communicates its NIU ID data and the bed's ID data to Ethernet 46 in packets through port 374 as indicated by arrows 478, 480, respectively. If unit 366 senses that port 374 is not coupled to Ethernet 466, as shown in FIG. 24, for example, then unit 366 sends its NIU ID data to the associated bed 364, as indicated by arrow 482, and then bed 364 wirelessly transmits its bed ID data and the NIU ID data to transceiver 472 in wireless packets as indicated by arrows 484, 486, respectively. The data path for other types of bed status data is the same path as that for bed ID data shown in FIGS. 23 and 24 depending upon whether or not unit 366 is connected to Ethernet via port 374.

Beds 10, 159, 314, 342, 362, 364 each have power cords (not shown) that are plugged into electrical outlets in hospital rooms during normal use of the beds 10, 159, 314, 342, 362, 364, regardless of whether the beds 10, 159, 314, 342, 362, 364 communicate with other devices in the associated network via wired or wireless connections. According to this disclosure, when the power cords of beds 10, 159, 314, 342, 362, 364 are unplugged, which usually happens when the bed is to be moved from one location in a healthcare facility to another, the associated Care Alert templates are automatically disabled, for example, by system 112 in the case of beds 159. Thus, even if the bed 10, 159, 314, 342, 362, 364 is still able to communicate bed data wirelessly during transit from one location to another, the associated nurse call system (e.g., system 112) does not initiate any communications with the wireless communication devices carried by the caregivers. Such alarm notifications are not generally needed because other caregivers should be accompanying the bed 10, 159, 314, 342, 362, 364 during transit. Before the automatic disabling of the Care Alert templates, a slight delay period, such as 10 or 20 seconds, may be required to elapse so that, if the bed's power plug was unplugged inadvertently, there is time to plug the bed back in before the Care Alert templates are disabled.

In the case of beds 10, 159, 314, 342, 362, 364 that communicate wirelessly, data is sent from the bed's wireless transmitter to notify the associated nurse call system that the bed has been unplugged. Such data may be transmitted after the above-mentioned delay period (i.e., the bed determines when the delay period has elapsed) or substantially immediately in response to the bed being unplugged (i.e., the nurse call system determines when the delay period has elapsed). In the latter case, appropriate data is sent from the bed's wireless transmitter if the bed is plugged back in before the delay period elapses so that the nurse call system does not disable the Care Alert template.

Beds having wireless communication circuitry may be powered by battery back-up power or by one or more capacitors for a period of time sufficient to permit the transmission of data indicating that the bed has been unplugged (and, in some embodiments, for a return acknowledgment to be received by the bed). In the case of beds 10, 159, 314, 342, 362, 364 coupled to NIU 366, the NIU 366 sends appropriate signals to the nurse call system indicating either that the power cord of the bed has been unplugged or that the bed has been unplugged from the NIU 366. Additionally or alternatively, the nurse call system may also conclude that the bed 10, 159, 314, 342, 362, 364 has been unplugged and is in transit if a different wireless transceiver or receiver (such as units 140) of an associated locating-and-tracking system (such as system 141) receives signals from the tag (such as tag 142) mounted to the bed 10, 159, 314, 342, 362, 364 and proceed to automatically disable the Care Alert alarm notifications as a result.

In some embodiments, after the bed 10, 159, 314, 342, 362, 364 reaches its new location and the associated power cord is plugged back in, a caregiver signals the nurse call system to re-enable the Care Alert templates for the particular bed. Caregivers may re-enable the Care Alert templates for the particular bed 10, 159, 314, 342, 362, 364 by making appropriate entries on either an audio station in the room, a computer at the master nurse call station, or the wireless communication device carried by the caregiver. The re-enabling of the Care Alert template may be made by voice commands entered into the wireless communication device in some embodiments.

Because the nurse call system receives bed ID data, the particular Care Alert template associated with the bed 10, 159, 314, 342, 362, 364 is known by the nurse call system. Thus, unless overridden by users of the nurse call system, the association between bed, patient, and assigned caregivers is maintained by the nurse call system even if the bed is moved to a new location. If one of the assigned caregivers does not re-enable the Care Alert template within a predetermined period of time after the nurse call system determines that the bed has been plugged back in (such determination being made in any of the ways described above for determining that the bed has been unplugged), then a reminder to re-enable the Care Alert template may be initiated by the nurse call system to the wireless communication devices carried by one or more of the assigned caregivers.

In alternative embodiments, the nurse call system may re-enable the Care Alert templates automatically after bed 10, 159, 314, 342, 362, 364 has been moved and then plugged back in. Alternatively or additionally, the nurse call system may initiate a communication to the wireless communication devices of assigned caregivers advising that the nurse call system will re-enable the Care Alert templates within a predetermined period of time unless receiving instructions not to do so.

The data received from beds 10, 159, 314, 342, 362, 364 by the associated nurse call system (such as system 112) may be provided to other systems of the hospital network. In one example, beds 10, 159, 314, 342, 362, 364 having weigh scale systems transmit patient weight to system 112 which, in turn, transmits the patient weight data to an electronic medical records (EMR) system (such as system 18) which, in turn, stores the weight information in the associated patient's record. The nurse call system 112 may convert the data from one communication protocol into another communication protocol. Thus, patient weight data received by system 112 may be converted by system 112 into the Health Level 7 (HL7) protocol for transmission to the EMR system.

Hospital computer networks are usually coupled to the Internet. Accordingly, because beds 10, 159, 314, 342, 362, 364 are coupled to the hospital network (such as network 110), data from beds 10, 159, 314, 342, 362, 364 may be made available on the Internet. Such data is password protected in some embodiments. In addition, software upgrades may be communicated to beds 10, 159, 314, 342, 362, 364 and to the nurse call system by the bed manufacturer and the nurse call system manufacturer, for example, over the Internet and hospital network. The software upgrades to the bed may be received from the hospital network wirelessly or via a wired connection to the hospital network. Additionally or alternatively, the software of the nurse call system and/or bed may be field upgradable via a computer that a field technician couples to the hospital network while visiting the facility.

Different types of hospital beds have different features and functions. Thus, beds 10, 159, 314, 342, 362, 364 may not have all of the types of functions that may be configured on certain ones of the Care Alert templates. For example, not all beds have bed exit systems or weigh scale systems. As another example, many beds don't have specialized therapy surfaces such as rotation surfaces, low-air-loss surfaces, or alternating pressure surfaces. According to this disclosure, beds 10, 159, 314, 342, 362, 364 transmit data to the associated nurse call system (such as system 112) which indicates the bed configuration (e.g., the types of functions with which the bed is equipped). In some embodiments, the nurse call system "grays out" (e.g., renders unusable) the portions of any Care Alert templates corresponding to feature and functions not present on the associated bed. In other embodiments, the nurse call system removes such features or functions from the Care Alert templates altogether. In still other embodiments, the nurse call system may provide a notification at the master nurse call station and/or via a transmission to an assigned caregiver's wireless communication device to indicate that a particular bed lacks a particular function included on a particular Care Alert template that the user is attempting to configure for the particular bed. Such notifications may also be provided by the nurse call system in those situations where a Care Alert template is first assigned to a patient (such as via the ADT system as described above) and then, subsequently, a bed lacking certain features or functions is assigned to the patient.

It should be understood that features of each of the embodiments described above are applicable to all of the other described embodiments. For example, the description of features and functions of the system of FIGS. 1-9 are applicable to the system of FIGS. 10-16 and vice versa. The features of the system and algorithm of FIGS. 17-19 are applicable to the FIG. 1-9 and FIG. 10-16 systems and vice versa. The manner in which beds 342, 362, 364 connect to other systems via various wired and wireless connectivity schemes is also applicable to beds 10 of the FIG. 1-9 system, to beds 159 of the FIG. 10-16 system, and to beds 314 of the FIG. 17-19 system.

Although certain embodiments have been described in detail above, variations and modifications exist within the scope and spirit of this disclosure as described and as defined in the following claims.

The invention claimed is:

1. A system for alerting caregivers carrying wireless communication devices of alarm conditions associated with pieces of equipment in a healthcare facility, the system comprising at least one computer device that is remote from the pieces of equipment and that receives data from the pieces of equipment, a display screen associated with the computer device, the computer device being operable to display at least one template screen on the display screen, the at least one template screen permitting a user to select types of alarms to which designated caregivers are to be notified, the computer device being operable to initiate a communication to the wireless communication device of at least one of the designated caregivers in response to the data received from at least one of the pieces of equipment being indicative of at least one of the types of alarms selected on the at least one template screen, at least one of the pieces of equipment being a hospital bed, the computer device receiving configuration data from the hospital bed indicative of features with which the hospital bed is equipped, and the computer device rendering portions of at least one of the template screens unusable, the portions of the template screens rendered unusable corresponding to features absent from the hospital bed.

2. The system of claim 1, wherein the at least one template screen is configured to permit entry of one or more numerical quantities representing associated threshold values above which or below which an alarm condition is considered to exist.

3. The system of claim 1, wherein the computer device is operable by the user to create a new template screen in which alarm conditions of the user's choosing are included on the new template screen.

4. The system of claim 1, wherein the at least one template screen is configured to permit users to select which of a plurality of levels of priority is to be assigned to at least one of the alarm conditions.

5. The system of claim 1, wherein the communication initiated by the computer device comprises an alphanumeric message destined for receipt by the wireless communication device of the at least one caregiver.

6. The system of claim 1, wherein the communication initiated by the computer device comprises an audio message destined for receipt by the wireless communication device of the at least one caregiver.

7. The system of claim 1, wherein the computer device is operable to initiate communications with pagers, wireless badges, and wireless handsets.

8. The system of claim 1, wherein the computer device is operable to display on the display screen a floor plan showing each room of at least a portion of the healthcare facility, at least some of the rooms on the floor plan being color coded to indicate room cleanliness status.

9. The system of claim 1, wherein the computer device is operable to display on the display screen an image of a hospital bed with at least a portion of the image of the hospital bed being color coded to indicate an alarm condition associated with the portion of the image.

10. The system of claim 1, wherein the computer device is operable to display information about at least one of the following associated with a hospital bed: a head section angle, a bed exit system, a patient position monitoring system, a height of an upper frame relative to a base frame, a siderail position, a therapy provided by a patient-support surface, a turn assist function of a patient-support surface, an inflatable vest which is inflated via components included on the hospital bed, whether the hospital bed is receiving power from a wall outlet, and whether certain functions of the hospital bed are disabled.

11. The system of claim 1, wherein the computer device is operable to communicate via a network of the healthcare facility with any at least one of the following: an electronic medical records database, a nurse call badge, a nurse location badge, a workflow process system, a personal data assistant (PDA), a voice communication badge, a badge having text message capability, and a pager.

12. The system of claim 1, wherein the computer device is operable to cause at least a portion of an image to flash on the display screen in response to the data received from at least one of the pieces of equipment being indicative of at least one of the types of alarms selected on the at least one template screen.

13. The system of claim 1, wherein the portions of the template screens are rendered unusable by being grayed out on the at least one template screens or by being removed from the at least one template screens.

14. The system of claim 1, wherein at least one of the pieces of equipment is a hospital bed having a weigh scale system operable to determine patient weight, the computer device receives patient weight data from the hospital bed, and the computer device transmits the patient weight data to an electronic medical records system for entry into a patient record.

15. The system of claim 14, wherein the computer device receives the patient weight data in a first format according to a first communications protocol and the computer device transmits the patient weight data to the electronic medical records system in a second format according to a second communications protocol.

16. The system of claim 15, wherein the second communications protocol is an HL7 protocol.

17. The system of claim 1, wherein at least one of the pieces of equipment is a hospital bed and the data comprises status data indicating whether the hospital bed is clean or dirty.

18. The system of claim 17, wherein the status data is based on manipulation of a user input of the hospital bed.

19. The system of claim 17, further comprising an audio station coupled to the computer device and wherein the status data is based on manipulation of a user input of the audio station.

20. The system of claim 1, wherein at least one of the pieces of equipment is a hospital bed having a power plug which plugs into a power outlet to provide power to the hospital bed and the computer device being operable to receive plug-connection data indicative of whether the power plug of the hospital bed is plugged into the power outlet.

21. The system of claim 1, further comprising a network interface unit coupled to an Ethernet, at least one of the pieces of equipment being a hospital bed that communicates bed data to the network interface unit, and the network interface unit being operable to convert bed data formatted according to a first protocol into an Ethernet protocol.

22. The system of claim 1, further comprising a network interface unit coupled to an Ethernet, at least one of the pieces of equipment being a hospital bed having a data cable which plugs into the network interface unit, and the computer device receiving cable-connection data indicative of whether the data cable of the hospital bed is plugged into the network interface unit.

23. A system for alerting caregivers carrying wireless communication devices of alarm conditions associated with pieces of equipment in a healthcare facility, the system comprising at least one computer device that is remote from the pieces of equipment and that receives data from the pieces of equipment, a display screen associated with the computer device, the computer device being operable to display at least one template screen on the display screen, the at least one template screen permitting a user to select types of alarms to which designated caregivers are to be notified, the computer device being operable to initiate a communication to the wireless communication device of at least one of the designated caregivers in response to the data received from at least one of the pieces of equipment being indicative of at least one of the types of alarms selected on the at least one template screen, a plurality of audio stations located remotely from the computer device, and a locating-and-tracking system operable to determine locations of caregivers, the computer device being operable to communicate an audio message to one of the audio stations nearest the designated caregiver as determined by information received by the locating-and-tracking system.

24. The A system for alerting caregivers carrying wireless communication devices of alarm conditions associated with pieces of equipment in a healthcare facility, the system comprising at least one computer device that is remote from the pieces of equipment and that receives data from the pieces of equipment, a display screen associated with the computer device, the computer device being operable to display at least one template screen on the display screen, the at least one template screen permitting a user to select types of alarms to which designated caregivers are to be notified, the computer device being operable to initiate a communication to the wireless communication device of at least one of the designated caregivers in response to the data received from at least one of the pieces of equipment being indicative of at least one of the types of alarms selected on the at least one template screen, wherein, if a first of the designated caregivers does not respond to the communication within a predetermined period of time, then the computer device operates to automatically initiate the communication to a second of the designated caregivers.

25. A system for alerting caregivers carrying wireless communication devices of alarm conditions associated with pieces of equipment in a healthcare facility, the system comprising at least one computer device that is remote from the pieces of equipment and that receives data from the pieces of equipment, a display screen associated with the computer device, the computer device being operable to display at least one template screen on the display screen, the at least one template screen permitting a user to select types of alarms to which designated caregivers are to be notified, the computer device being operable to initiate a communication to the wireless communication device of at least one of the designated caregivers in response to the data received from at least one of the pieces of equipment being indicative of at least one of the types of alarms selected on the at least one template screen, the computer device being operable to cause at least a portion of an image to flash on the display screen in response to the data received from at least one of the pieces of equipment being indicative of at least one of the types of alarms selected on the at least one template screen, and a locating-and-tracking system to monitor the whereabouts of caregivers in the healthcare facility, the computer device being operable to cause the portion of the image to cease flashing when the data from the locating-and-tracking system indicates that at least one of the designated caregivers has entered a room in which the alarm is occurring.

26. A system for alerting caregivers carrying wireless communication devices of alarm conditions associated with pieces of equipment in a healthcare facility, the system comprising at least one computer device that is remote from the pieces of equipment and that receives data from the pieces of equipment, a display screen associated with the computer device, the computer device being operable to display at least one template screen on the display screen, the at least one template screen permitting a user to select types of alarms to which designated caregivers are to be notified, the computer device being operable to initiate a communication to the wireless communication device of at least one of the designated caregivers in response to the data received from at least one of the pieces of equipment being indicative of at least one of the types of alarms selected on the at least one template screen, and a locating-and-tracking system to monitor the whereabouts of caregivers in the healthcare facility, the computer device being operable to detect whether at least one designated caregiver has exited a room without rectifying a cause of an alarm and, if so, the computer device being operable to notify the at least one designated caregiver that the cause of the alarm still exists.

27. A system for alerting caregivers carrying wireless communication devices of alarm conditions associated with pieces of equipment in a healthcare facility, the system comprising at least one computer device that is remote from the pieces of equipment and that receives data from the pieces of equipment, a display screen associated with the computer device, the computer device being operable to display at least one template screen on the display screen, the at least one template screen permitting a user to select types of alarms to which designated caregivers are to be notified, the computer device being operable to initiate a communication to the wireless communication device of at least one of the designated caregivers in response to the data received from at least one of the pieces of equipment being indicative of at least one of the types of alarms selected on the at least one template screen, the at least one computer device is being operable by users to designate a first set of alarm conditions to which at least one designated caregiver is to be alerted during a first period of time and to designate a second set of alarm conditions to which at least one designated caregiver is to be alerted during a second period of time.

28. The system of claim 27, wherein the first period of time and the second period of time partially overlap.

29. The system of claim 27, wherein the second period of time begins upon the expiration of the first time period.

30. The system of claim 27, wherein the first period of time and the second period or time are separated by an interim period of time.

31. The system of claim 27, wherein at least one of the first and second periods of time begin in response to detection by the at least one computer device of a predetermined condition.

32. The system of claim 27, wherein at least one of the first and second periods of time end in response to detection by the at least one computer device of a predetermined condition.

33. The system of claim 27, wherein at least one of the first and second periods of time begin at a predetermined time.

34. The system of claim 27, wherein at least one of the first and second periods of time end at a predetermined time.

35. The system of claim 27, wherein some of the alarm conditions of the first set are also included in the second set.

36. The system of claim 27, wherein the at least one computer device is operable to communicate a reminder to at least one designated caregiver a preset amount of time before the expiration of the first period of time.

37. The system of claim 27, wherein the first set of alarm conditions are based on a first Standard of Care for a patient and the second set of alarm conditions are based on a second Standard of Care for the patient.

38. A system for alerting caregivers carrying wireless communication devices of alarm conditions associated with pieces of equipment in a healthcare facility, the system comprising at least one computer device that is remote from the pieces of equipment and that receives data from the pieces of equipment, a display screen associated with the computer device, the computer device being operable to display at least one template screen on the display screen, the at least one template screen permitting a user to select types of alarms to which designated caregivers are to be notified, the computer device being operable to initiate a communication to the wireless communication device of at least one of the designated caregivers in response to the data received from at least one of the pieces of equipment being indicative of at least one of the types of alarms selected on the at least one template screen, the computer device receiving a patient name and a template name from an admission, discharge, and tracking (ADT) system and the computer device associating one of the template screens with the patient in response to receiving the template name.

39. A system for alerting caregivers carrying wireless communication devices of alarm conditions associated with pieces of equipment in a healthcare facility, the system comprising at least one computer device that is remote from the pieces of equipment and that receives data from the pieces of equipment, a display screen associated with the computer device, the computer device being operable to display at least one template screen on the display screen, the at least one template screen permitting a user to select types of alarms to which designated caregivers are to be notified, the computer device being operable to initiate a communication to the wireless communication device of at least one of the designated caregivers in response to the data received from at least one of the pieces of equipment being indicative of at least one of the types of alarms selected on the at least one template screen, at least one of the pieces of equipment being a hospital bed, the computer device being operable to associate bed identification data with patient identification data and with caregiver identification data so that, if the hospital bed is moved to a new location, the computer device maintains the association between the hospital bed, the patient, and at least one of the designated caregivers.

40. The system of claim 39, wherein the hospital bed has wireless communication circuitry that transmits in-transit data indicating that the hospital bed is in transit.

41. The system of claim 40, wherein the hospital bed transmits the in-transit data in response to a power cord of the hospital bed being unplugged.

42. The system of claim 39, further comprising a network interface unit that is coupled to the computer device by a network and that is coupled to the hospital bed by a data cable, the network interface unit being configured to transmit in-transit data to the computer device in response to the data cable being unplugged from the network interface unit.

43. The system of claim 39, wherein the computer device is operable to associate one of the template screens with the patient, the computer device is operable to disable the alarms of the associated template screen for at least a portion of time that the hospital bed is in transit, and the computer device is operable to re-enable the associated template screen after the hospital bed is moved to the new location.

44. The system of claim 43, wherein the associated template screen is re-enabled in response to commands received from at least one of the designated caregivers.

45. The system of claim 44, wherein the computer device is operable to transmit a reminder to at least one of the designated caregivers if the at least one designated caregiver does not re-enable the template screen within a predetermined period of time.

46. The system of claim 43, wherein the associated template screen is re-enabled automatically by the computer device after the hospital bed is moved to the new location.

* * * * *